(12) United States Patent
Winger et al.

(10) Patent No.: US 10,323,282 B2
(45) Date of Patent: Jun. 18, 2019

(54) METHODS AND COMPOSITIONS FOR ASSESSING PATIENTS WITH PREECLAMPSIA-RELATED CONDITIONS USING MICRORNA

(71) Applicant: Edward E. Winger, M.D., Professional Corporation, San Francisco, CA (US)

(72) Inventors: Edward E. Winger, San Francisco, CA (US); Jane L. Reed, Klamah Falls, OR (US)

(73) Assignee: Edward E. Winger, M.D., Professional Corporation, San Francisco, CA (US)

( * ) Notice: Subject to any disclaimer, the term of this patent is extended or adjusted under 35 U.S.C. 154(b) by 0 days.

(21) Appl. No.: 13/899,555

(22) Filed: May 21, 2013

(65) Prior Publication Data

US 2013/0245135 A1    Sep. 19, 2013
US 2016/0333406 A9    Nov. 17, 2016

Related U.S. Application Data

(63) Continuation-in-part of application No. PCT/US2012/061994, filed on Oct. 25, 2012, which is a continuation-in-part of application No. 13/284,739, filed on Oct. 28, 2011, now abandoned.

(60) Provisional application No. 61/767,669, filed on Feb. 21, 2013, provisional application No. 61/456,063, filed on Nov. 1, 2010.

(51) Int. Cl.
     *C12N 15/11*      (2006.01)
     *C12Q 1/6883*      (2018.01)
     *C12Q 1/6886*      (2018.01)

(52) U.S. Cl.
     CPC ......... *C12Q 1/6883* (2013.01); *C12Q 1/6886* (2013.01); *C12Q 2600/106* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2009/0123933 A1   5/2009   Mishra
2009/0176237 A1   7/2009   Ferguson et al.
2010/0298151 A1*   11/2010   Taylor et al. .......... 506/2

FOREIGN PATENT DOCUMENTS

EP      2336353 A1    6/2011
EP      2354246 A1    8/2011
WO    WO-2009/015357 A1    1/2009
WO    WO-2009/093254 A2    7/2009
WO    WO 2009093254 A2 *    7/2009
WO    WO-2009/134452 A2    11/2009

OTHER PUBLICATIONS

Miura et al, Identification of Pregnancy-Associated MicroRNAs in Maternal Plasma, Aug. 2010, Clinical Chemistry, vol. 56, 11:1767-1771.*
Foekens et al, Four miRNAs associated with aggressiveness of lymph node-negative, estrogen receptor-positive human breast cancer, 2008, PNAS, vol. 105, 35: 13021-13026.*
Chen (2005) "MicroRNA Quantitation by RT-PCR," http://www3.appliedbiosystems.com/cms/groups/mcb_marketing/documents/generaldocuments/cms_040548.pdf (1 page).
"TaqMan MicroRNA Assays Product Overview," (2010) http://www3.appliedbiosystems.com/cms/groups/mcb_marketing/documents/generaldocuments/cms_068884.pdf (2 pages).
Holmstrom et al. (2010) "Identification of a microRNA signature in dendritic cell vaccines for cancer immunotherapy," Human Immunology, 71: 67-73.
Hu et al. (2011) "Two common SNPs in pri-miR-125a alter the mature miRNA expression and associate with recurrent pregnancy loss in a Han-Chinese population," RNA Biology, 8(5): 861-872.
Montenegro et al. (2007) "Differential expression of microRNAs with progression of gestation and inflammation in the human chorioamniotic membranes," Am. J. Obstet. Gynecol., 197: 289.e1-289.e6.
Pineles et al. (2007) "Distinct subsets of microRNAs are expressed differentially in the human placentas of patients with preeclampsia," Am. J. Obstet. Gynecol., 196: 261.e1-261.e6.
Reid et al. (2010) "Circulating microRNAs: Association with disease and potential use as biomarkers," Critical Reviews in Oncology/Hematology, 80: 193-208.
Revel et al. (2011) "MicroRNAs are associated with human embryo implantation defects,"Human Reproduction, 26(10): 2830-2840.
Scagnolari et al. (2009) "Expression of interferon-induced microRNAs in patients with chronic hepatitis C virus treated with pegylated interferon alpha," Clinical Microbiology and Infection, 15(S4): S592-S593.
Christiansen et al. (2002) "A randomized, double-blind, placebo controlled trial of intravenous immunoglobulin in the prevention of recurrent miscarriage: evidence for a therapeutic effect in women with secondary recurrent miscarriage," Human Reproduction, 17(3): 809-816.
Levy et al. (2000) "Intravenous Immunoglobulin Treatment of Lupus Nephritis," Seminars in Arthritis and Rheumatism, 29(5): 321-327.
Otsuka et al. (2008) "Impaired microRNA processing causes corpus luteum insufficiency and infertility in mice," The Journal of Clinical Investigation, 118(5): 1944-1954.

(Continued)

*Primary Examiner* — Ekaterina Poliakova-Georgantas
(74) *Attorney, Agent, or Firm* — Patrick J. Halloran

(57) ABSTRACT

The invention is directed to methods and compositions for collecting a non-placental biological samples of cells and quantifying and comparing levels of expression of microRNAs to characterize a preeclampsia-related condition. The samples may be collected before or after an intervention or may be collected over a period of time. One of the samples may be a control sample. Patients may then be treated according to their response.

12 Claims, 27 Drawing Sheets

Specification includes a Sequence Listing.

(56) References Cited

OTHER PUBLICATIONS

Pan et al. (2008) "MicroRNA Signature and Regulatory Functions in the Endometrium during Normal and Disease States," Semin. Reprod. Med., 26(6): 479-493.
Roman et al. (2008) "MicroRNA Expression in Maternal Blood is Altered in Preeclampsia," American Journal of Obstetrics and Gynecology, 199(6): S175.
U.S. Appl. No. 13/284,738, Methods and Compositions for Assessing Patients With Reproductive Failure Using Immune Cell-Derived Microrna, filed Oct. 28, 2011, Abandoned.

* cited by examiner

| Number | miR |
|---|---|
| 1. | 1 |
| 2. | 1229 |
| 3. | 1244 |
| 4. | 1267 |
| 5. | 132 |
| 6. | 133b |
| 7. | 144-3p |
| 8. | 146a |
| 9. | 148a-3p |
| 10. | 155 |
| 11. | 16 |
| 12. | 181a |
| 13. | 193a-3p |
| 14. | 196a |
| 15. | 199a-5p |
| 16. | 199b-5p |
| 17. | 210 |
| 18. | 219-5p |
| 19. | 221-5p |
| 20. | 223 |
| 21. | 301a-3p |
| 22. | 30e-3p |
| 23. | 33a-5p |
| 24. | 340-5p |
| 25. | 424-5p |
| 26. | 513a-5p |
| 27. | 575 |
| 28. | 582-5p |
| 29. | 671-3p |
| 30. | 7-5p |

FIG. 1

| # | microRNA | Mean Preeclamp preeconception (no IVIG) | SD | Mean healthy preconception (no IVIG) | SD | Diff | Mean SD | Difference/Mean SD | Diff Mean ≥ SD |
|---|---|---|---|---|---|---|---|---|---|
| 1 | miR223 | 5.9353582 | 0.19973 | 5.2375839 | 0.865843 | 0.70077 | 0.5327 | 1.3152302 | x |
| 2 | miR7-5p | 26.751411 | 1.23216 | 25.159305 | 1.550677 | 1.59210 | 1.3914 | 1.14423 | x |
| 3 | miR148a-3p | 23.455389 | 1.67104 | 21.613993 | 1.696852 | 1.84139 | 1.6839 | 1.0934492 | x |
| 4 | miR144-3p | 32.608333 | 4.20317 | 29.256651 | 2.060369 | 3.35168 | 3.1332 | 1.0697067 | x |
| 5 | miR16 | 9.4310483 | 0.58627 | 8.6663557 | 0.885624 | 0.76569 | 0.7359 | 1.040411 | x |
| 6 | miR582-5p | 26.35786 | 1.06288 | 25.287809 | 1.025575 | 1.07005 | 1.0442 | 1.0247246 | x |
| 7 | miR1244 | 23.946469 | 1.62893 | 22.085187 | 2.364680 | 1.86128 | 1.9967 | 0.9321327 | |
| 8 | miR1 | 28.365619 | 3.89668 | 25.387782 | 3.020069 | 2.97783 | 3.4613 | 0.860307 | |
| 9 | miR221-5p | 34.312147 | 2.75545 | 31.877247 | 2.989927 | 3.43490 | 2.8726 | 0.847402 | |
| 10 | miR194b-5p | 28.558513 | 0.85076 | 27.579774 | 1.494593 | 0.97873 | 1.1726 | 0.8344166 | |
| 11 | miR301a-3p | 19.470103 | 1.60884 | 18.136789 | 1.943412 | 1.33331 | 1.7761 | 0.7506855 | |
| 12 | miR30e-3p | 15.791047 | 0.34807 | 15.019474 | 1.718498 | 0.77157 | 1.0332 | 0.746782 | |
| 13 | miR219-5p | 32.488847 | 0.97250 | 31.455452 | 1.994269 | 1.03339 | 1.4833 | 0.6966453 | |
| 14 | miR575 | 29.564538 | 1.95219 | 27.843664 | 3.156216 | 1.72087 | 2.5542 | 0.673417 | |
| 15 | miR340-5p | 18.500961 | 1.06127 | 17.845222 | 1.150327 | 0.65574 | 1.1058 | 0.593009 | |
| 16 | miR181a | 21.680646 | 1.07330 | 20.760433 | 2.593583 | 0.92021 | 1.8334 | 0.5019031 | |
| 17 | miR132 | 21.063171 | 1.06303 | 20.381676 | 1.394265 | 0.70049 | 1.4786 | 0.4737739 | |
| 18 | miR193a-3p | 26.330676 | 1.95248 | 25.696892 | 1.142370 | 0.63378 | 1.5474 | 0.4095719 | |
| 19 | miR199a-5p | 26.147211 | 1.03086 | 25.433075 | 3.004047 | 0.71413 | 2.0174 | 0.3539786 | |
| 20 | miR1267 | 8.213199 | 1.11349 | 7.869795 | 1.052899 | 0.33340 | 1.0981 | 0.3126974 | |
| 21 | miR1229 | 28.735398 | 2.27492 | 28.316486 | 3.543655 | 0.41890 | 2.9092 | 0.1439902 | |
| 22 | miR155 | 13.034953 | 0.56869 | 12.946248 | 1.071482 | 0.08868 | 0.8200 | 0.1081415 | |
| 23 | miR133b | 26.313422 | 3.14179 | 26.071514 | 4.136901 | 0.24190 | 3.6393 | 0.06647 | |
| 24 | miR671-3p | 22.719776 | 0.95274 | 22.66222 | 1.81620 | 0.05755 | 1.3844 | 0.0415717 | |
| 25 | RNU48 | 8.6857737 | 1.899E- | 8.6857739 | 2.236E- | -1.322E- | 1.213E- | -0.108986 | |
| 26 | miR210 | 20.969833 | 0.95201 | 21.245228 | 1.503172 | | 1.2280 | -0.2242461 | |
| 27 | miR146a | 12.962683 | 0.79441 | 13.423444 | 1.136541 | | 0.9634 | -0.4772358 | |
| 28 | miR424-5p | 28.783956 | 15.6333 | 34.070074 | 2.144077 | | 8.8887 | -0.5946995 | |
| 29 | miR33a-5p | 35.399642 | NA | 37.798633 | NA | | NA | NA | |
| 30 | miR513a-5p | NA | NA | 30.309538 | NA | | NA | NA | |

FIG. 2

| | MicroRNA | Most severe outcome | Least severe outcome group | |Difference Mean| | >1.0 absolute value |
|---|---|---|---|---|---|
| 1 | miR144-3p | 32.608333 | 30.127496 | 2.4808377 | xx |
| 2 | miR148a-3p | 23.453389 | 21.741576 | 1.7718123 | xx |
| 3 | miR582-5p | 26.33786 | 25.038048 | 1.2998115 | xx |
| 4 | miR301a-3p | 19.470103 | 18.210029 | 1.260739 | xx |
| 5 | miR221-5p | 34.311147 | 33.361485 | 0.9496626 | |
| 6 | miR7-5p | 26.751111 | 25.846969 | 0.9044421 | |
| 7 | miR1 | 28.365619 | 27.509822 | 0.8557969 | |
| 8 | miR193a-3p | 26.338676 | 25.627125 | 0.7035515 | |
| 9 | miR181a | 21.680646 | 21.058342 | 0.622304 | |
| 10 | miR1229 | 28.735396 | 28.289278 | 0.4461186 | |
| 11 | miR30e-3p | 15.791047 | 15.443666 | 0.3473807 | |
| 12 | miR223 | 5.9385382 | 5.6794295 | 0.2592287 | |
| 13 | miR16 | 9.4310483 | 9.1840572 | 0.2469911 | |
| 14 | miR199b-5p | 28.558513 | 28.34182 | 0.216693 | |
| 15 | miR340-5p | 18.500961 | 18.382126 | 0.1188347 | |
| 16 | miR1267 | 8.2131199 | 8.1375255 | 0.0755736 | |
| 17 | miR1244 | 23.94460 | 23.982041 | -0.0035726 | |
| 18 | miR132 | 21.082171 | 21.147478 | -0.0653067 | |
| 19 | miR219-5p | 32.488847 | 32.634428 | -0.1455817 | |
| 20 | miR210 | 20.969833 | 21.273242 | -0.303409 | |
| 21 | miR155 | 13.031933 | 13.421923 | -0.3869901 | |
| 22 | miR671-3p | 22.719776 | 23.263988 | -0.5442099 | |
| 23 | miR146a | 12.962683 | 14.027169 | -1.0644865 | xx |
| 24 | miR575 | 29.565338 | 30.943086 | -1.3378548 | xx |
| 25 | miR199a-5p | 26.142211 | 27.59243 | -1.4452184 | xx |
| 26 | miR13b | 26.313422 | 28.965483 | -2.6520619 | xx |
| 27 | miR424-5p | 28.785956 | 34.246781 | -5.4648249 | xx |
| 28 | miR33a-5p | NA | NA | NA | |
| 29 | miR513a-5p | 35.399642 | NA | NA | |

FIG. 3

| | No IVIG Preg 30–83 days gestation | Average Preeclampsia | SD | Average Healthy | SD | Diff Preeclamp> Healthy | Top MiRs |
|---|---|---|---|---|---|---|---|
| 1. | miR210 | 19.89703 | 2.487452 | 18.89384 | 1.775958 | 1.003183 | xxx |
| 2. | miR1229 | 29.32381 | 6.004916 | 28.64724 | 7.150626 | 0.676571 | xxx |
| 3. | miR181a | 21.18063 | 1.769684 | 20.69283 | 2.234647 | 0.467796 | |
| 4. | miR199b-5p | 27.87894 | 1.771642 | 27.478 | 1.579001 | 0.400949 | |
| 5. | miR155 | 12.50337 | 0.91561 | 12.2423 | 1.254998 | 0.261071 | |
| 6. | miR199a-5p | 26.14488 | 2.448695 | 25.97349 | 2.015394 | 0.171392 | |
| 7. | miR671-3p | 22.99922 | 1.734981 | 22.97561 | 1.381249 | 0.02361 | |
| 8. | miR1244 | 23.19291 | 1.592954 | 23.2083 | 1.228896 | -0.01539 | |
| 9. | miR1 | 26.60642 | 1.622788 | 26.79596 | 2.179235 | -0.18954 | |
| 10. | miR101a-3p | 19.10586 | 2.130487 | 19.31841 | 1.183039 | -0.21255 | |
| 11. | miR582-5p | 26.20947 | 2.134123 | 26.46293 | 1.753071 | -0.25346 | |
| 12. | miR146a | 12.80174 | 1.930241 | 13.08452 | 1.202815 | -0.28277 | |
| 13. | miR30e-3p | 15.54759 | 1.775011 | 15.91094 | 1.27695 | -0.36335 | |
| 14. | miR193a-3p | 24.41575 | 0.827462 | 24.81575 | 1.203996 | -0.4 | |
| 15. | miR7-5p | 25.62793 | 1.466678 | 26.07605 | 1.231494 | -0.44812 | |
| 16. | miR1267 | 7.837165 | 1.447184 | 8.294535 | 1.233147 | -0.45737 | |
| 17. | miR16 | 8.567367 | 1.39081 | 9.026538 | 0.826337 | -0.45917 | |
| 18. | miR33a-5p | 34.23892 | 3.404979 | 34.74127 | 2.584459 | -0.50236 | |
| 19. | miR133b | 25.99929 | 2.989639 | 26.58985 | 2.90145 | -0.59056 | |
| 20. | miR148a-3p | 22.81615 | 2.233724 | 23.49644 | 1.356509 | -0.68029 | |
| 21. | miR424-5p | 34.58638 | 2.376547 | 35.38121 | 2.213542 | -0.79483 | |
| 22. | miR14-3p | 29.56188 | 2.573335 | 30.40115 | 2.557475 | -0.83926 | |
| 23. | miR132 | 19.79337 | 1.616022 | 20.78744 | 1.523883 | -0.99407 | |
| 24. | miR223 | 5.380289 | 1.315431 | 6.40072 | 0.91837 | -1.02043 | |
| 25. | miR575 | 28.83335 | 4.559468 | 30.95945 | 3.435511 | -2.12611 | |
| 26. | miR340-5p | 17.69365 | 1.427746 | 20.01578 | 4.727012 | -2.32213 | xxx |
| 27. | miR513a-5p | NA | NA | NA | NA | NA | xxx |
| 28. | miR219-5p | NA | NA | NA | NA | NA | xxx |
| 29. | miR221-5p | 32.91273 | | | | NA | |

FIG. 4

| #1-#2 Deltas (Second subtract First draw) | Mean Delta Preeclampsia | SD | Mean Delta Healthy | SD | Diff Mean Deltas Preec-Healthy sorted | *=¦Diff¦>1.5 |
|---|---|---|---|---|---|---|
| 1. miR1229 | 1.664344 | 4.062297 | -1.16459 | 9.153184 | 2.82893221 | * |
| 2. miR582-5p | -0.35041 | 2.178151 | 0.216435 | 1.858936 | -0.56684683 | |
| 3. miR181a | -0.082 | 2.0273 | 0.546734 | 1.802467 | -0.62873374 | |
| 4. miR30e-3p | 0.566736 | 1.578751 | 1.234768 | 1.734048 | -0.66803214 | |
| 5. miR7-5p | 0.333436 | 1.878465 | 1.001485 | 1.838972 | -0.66804893 | |
| 6. miR155 | -0.47566 | 1.472299 | 0.419395 | 1.2846 | -0.89503661 | |
| 7. miR199b-5p | -0.45096 | 2.116822 | 0.561528 | 2.422081 | -1.01248567 | |
| 8. miR671-3p | 0.161612 | 1.242733 | 1.256423 | 1.796729 | -1.09481119 | |
| 9. miR301a-3p | -0.39893 | 1.953974 | 0.702132 | 1.936993 | -1.10106637 | |
| 10. miR16 | -0.5741 | 1.75602 | 0.56382 | 1.304906 | -1.10123454 | |
| 11. miR148a-3p | -0.14829 | 2.10214 | 1.008872 | 2.016051 | -1.15716652 | |
| 12. miR1267 | -0.52022 | 2.052435 | 0.744425 | 2.110527 | -1.26464784 | |
| 13. miR199a-5p | 0.55892 | 4.477745 | 1.825292 | 3.326427 | -1.26940076 | |
| 14. miR340-5p | -0.68798 | 1.975828 | 0.638336 | 1.543474 | -1.32631855 | |
| 15. miR1 | 0.917105 | 3.747041 | 2.251803 | 3.196092 | -1.33469862 | |
| 16. miR223 | -0.60009 | 1.312649 | 0.772999 | 1.37328 | -1.37304509 | |
| 17. miR146a | -0.60367 | 1.960942 | 1.013153 | 1.403613 | -1.61682563 | * |
| 18. miR210 | -1.61545 | 2.356478 | 0.090862 | 1.476382 | -1.70631026 | * |
| 19. miR1244 | -0.11395 | 2.14403 | 1.610984 | 1.400494 | -1.72493602 | * |
| 20. miR132 | -0.92768 | 2.381414 | 1.204482 | 2.108265 | -2.13250297 | * |
| 21. miR133b | 0.13756 | 3.200693 | 3.36184 | 4.511403 | -3.22427921 | * |

FIG. 5

| microRNA | Preclaims delta-Healthy delta Differences sorted (no IVIG used) | **MiRs that also show IVIG response |
|---|---|---|
| miR513a-5p | 9.381814 | ** |
| miR193a-3p | 8.286031 | ** |
| miR1443p | 4.778899 | |
| miR424-5p | 0.442717 | |
| miR362-5p | -0.66146 | |
| miR155 | -0.73623 | |
| miR132 | -0.82132 | |
| miR671-3p | -0.98243 | |
| miR223 | -0.99295 | |
| miR1267 | -1.06693 | |
| miR301a-3p | -1.08634 | |
| miR33a-5p | -1.16262 | |
| miR146a | -1.19385 | |
| miR181a | -1.5257 | |
| miR340-5p | -1.63166 | |
| miR148a-3p | -1.74699 | |
| miR1229 | -1.77302 | |
| miR16 | -1.99937 | |
| miR30e-3p | -2.39347 | |
| miR199a-5p | -2.41515 | |
| miR1244 | -2.45721 | |
| miR210 | -2.50161 | |
| miR7-5p | -2.65788 | ** |
| miR575 | -3.16853 | ** |
| miR221-5p | -3.65277 | ** |
| miR1330 | -4.22726 | ** |
| miR1 | -4.10057 | ** |
| miR199a-3p | -4.6889 | ** |
| miR219-5p | -23.4141 | ** |

FIG. 6

| Difference (No IVIG-Yes IVIG) | Healthy preg#1-preg#2 delta | **Healthy pregnancy miRs increased | Difference (No IVIG-Yes IVIG) | Preeclamp preg#1-preg#2 delta | ***, ** Preeclampsia miRs increased |
|---|---|---|---|---|---|
| 9.581814391 | miR513a-5p | ** | 15.59491 | miR575 | *** |
| 1.067960531 | miR219-3p |  | 14.86579 | miR219-5p | *** |
| 0.972358364 | miR132 |  | 7.697807 | miR33a-5p | *** |
| 0.562826984 | miR193a-3p | ** | 6.263661 | miR199a-5p | *** |
| -0.428060098 | miR13b |  | 3.659407 | miR1 | *** |
| -0.460240073 | miR181a |  | 3.595467 | miR144-3p |  |
| -0.774967574 | miR155 |  | 3.060394 | miR221-5p | *** |
| -0.781495673 | miR223 |  | 2.800139 | miR13b |  |
| -0.878739872 | miR671-3p |  | 2.02342 | miR671-3p | *** |
| -1.231610375 | miR146a |  | 1.886418 | miR7-5p |  |
| -1.244688502 | miR267 |  | 1.811109 | miR30e-3p |  |
| -1.400777245 | miR210 |  | 1.408245 | miR199b-5p |  |
| -1.521781969 | miR30e-3p |  | 1.265473 | miR1229 |  |
| -1.660698113 | miR1229 | *** | 1.223803 | miR181a |  |
| -1.625500866 | miR221-5p |  | 1.095414 | miR148a-3p |  |
| -1.911464433 | miR148a-3p |  | 0.119934 | miR16 | ** |
| -2.019405438 | miR144-3p |  | 0.263107 | miR340-5p |  |
| -2.022212453 | miR16 |  | 0.240938 | miR132 |  |
| -2.061520484 | miR301a-3p |  | 0.21485 | miR301a-3p |  |
| -2.168446081 | miR582-3p | *** | 0 | miR513a-5p |  |
| -2.271792894 | miR340-3p | *** | -0.14451 | miR223 |  |
| -2.330734203 | miR424-5p | *** | -0.55188 | miR582-5p |  |
| -2.422401432 | miR7-5p | *** | -0.53393 | miR146a |  |
| -4.572204071 | miR575 |  | -0.58744 | miR155 |  |
| -5.124776033 | miR1 |  | -0.73681 | miR210 |  |
| -5.829991299 | miR199a-5p |  | -1.066883 | miR267 |  |
| -17.60493693 | miR33a-5p |  | -1.12947 | miR424-5p |  |
| NA | miR199b-5p |  | -3.81769 | miR193a-3p | ** |

FIG. 7

| microRNA | Preclamp delta-Healthy delta Differences sorted (showing most disregulated microRNAs without treatment) | **MiRs that also show good IVIG response |
|---|---|---|
| Column | A | B |
| miR513a-5p | 9.581814 | ** |
| miR193a-3p | 8.286031 | ** |
| miR144-3p | 4.778699 | |
| miR424-5p | 0.442717 | |
| miR582-5p | -0.66146 | |
| miR155 | -0.73623 | |
| miR132 | -0.82132 | |
| miR671-3p | -0.98243 | |
| miR223 | -0.99295 | |
| miR1267 | -1.06668 | |
| miR301a-3p | -1.08634 | |
| miR103a-5p | -1.16262 | |
| miR146a | -1.19385 | |
| miR181a | -1.5257 | |
| miR40-5p | -1.63166 | |
| miR148a-3p | -1.74699 | |
| miR1229 | -1.77802 | |
| miR16 | -1.99057 | |
| miR50e-3p | -2.30347 | |
| miR199b-5p | -2.41515 | |
| miR1244 | -2.45721 | |
| miR210 | -2.50161 | |
| miR7-5p | -2.63788 | ** |
| miR575 | -3.16653 | ** |
| miR221-3p | -3.65277 | ** |
| miR133b | -4.32726 | ** |
| miR1 | -4.40233 | ** |
| miR199a-5p | -5.68587 | |
| miR219-5p | -23.4141 | |

FIG. 8

| MicroRNA | Preconception samples using not using LIT | Preconception samples using LIT | Difference LIT-no LIT sorted | miRs with diff ≥1 and SD<4.0 |
|---|---|---|---|---|
| miR1229 | 30.355701 | 4.31735 | 27.881369 | 3.8284135 | 2.474181355 | |
| miR221-3p | 32.815579 | 3.6157333 | 30.745651 | 9.0115685 | 2.069928683 | |
| miR75 | 29.719137 | 3.2767847 | 28.099928 | 3.6589957 | 1.619799742 | x |
| miR14b-3p | 31.107101 | 3.9271267 | 30.009963 | 2.4258103 | 1.097717778 | x |
| miR148a-3p | 23.206682 | 2.7210344 | 22.237221 | 1.5873061 | 0.969461124 | x |
| miR3a-5p | 36.277355 | 1.6183345 | 35.54978 | 3.7221017 | 0.722575323 | |
| miR30e-3p | 15.68306 | 1.2620781 | 15.176693 | 1.6585476 | 0.506466652 | |
| miR181a | 21.29636 | 1.7252785 | 20.796392 | 2.409404 | 0.499967556 | |
| miR582-5p | 26.181611 | 2.0361028 | 25.78663 | 1.0236022 | 0.39498125 | |
| miR301a-3p | 18.654712 | 1.8554901 | 18.560604 | 1.674495 | 0.094107479 | |
| miR223 | 5.692809 | 1.0730749 | 5.6570721 | 0.9734034 | 0.035728747 | |
| miR340-5p | 18.146104 | 1.5722411 | 18.227342 | 1.0311258 | -0.081238259 | |
| miR7-3p | 25.597456 | 1.6275840 | 25.709332 | 1.6029169 | -0.111876241 | |
| miR16 | 8.6945749 | 0.8957757 | 9.0118084 | 0.877265 | -0.317233524 | |
| miR219-5p | 32.169203 | 1.4366691 | 32.948535 | 3.2621096 | -0.379611874 | |
| miR671-3p | 22.476595 | 0.8484606 | 22.992357 | 1.605778 | -0.515596217 | |
| miR1244 | 22.287983 | 1.8864523 | 22.84199 | 2.2292843 | -0.557706273 | |
| miR132 | 20.120548 | 1.3913617 | 20.749164 | 1.8672274 | -0.628615748 | |
| miR1 | 25.824895 | 1.6963049 | 26.481287 | 3.5833455 | -0.656391368 | |
| miR133b | 25.545662 | 1.3418676 | 26.234755 | 4.2282995 | -0.689093194 | |
| miR146a | 12.582831 | 0.9062271 | 13.359963 | 1.1571931 | -0.777153229 | |
| miR155 | 12.073375 | 0.8099492 | 12.973361 | 1.1424217 | -0.899988684 | |
| miR210 | 19.848559 | 2.5526074 | 20.890372 | 1.5001796 | -1.041813464 | x |
| miR193a-3p | 24.853776 | 1.9833967 | 25.913977 | 1.3140437 | -1.060200743 | x |
| miR199b-5p | 27.393786 | 1.5410353 | 28.481506 | 1.6106237 | -1.087719966 | x |
| miR424-5p | 30.647017 | 11.487206 | 32.073808 | 9.212436 | -1.426791117 | |
| miR192a-5p | 25.068957 | 1.2683657 | 26.67368 | 3.971721 | -1.604723434 | x |
| miR1267 | 8.2877796 | 0.918604 | 9.9983873 | 7.6745536 | -1.730607769 | |
| miR513a-5p | 30.608133 | | 34.222384 | 5.5536007 | -3.614251428 | |

FIG. 9

| 27 samples Cut-off values | miR1229 results sorted <27.8 Pree | miR210 results sorted >20.4 Pree | miR223 results sorted >6.3 Heal | miR30e-3p results sorted >16.3 Heal | miR340-5p results sorted >19.3 Heal | miR575 results sorted >29.0 Heal |
|---|---|---|---|---|---|---|
| 1 | 38.62050081 | 24.07793341* | 8.860663363* | 18.01094133* | 39.39112864 | 39.81596996 |
| 2 | 38.02145501 | 21.52731897* | 8.334410529* | 18.006660363* | 21.45694842* | 38.31117128 |
| 3 | 35.48926544 | 21.40566071* | 8.090890993* | 17.60716767* | 20.99752293* | 36.34061342 |
| 4 | 34.92860193 | 21.15820249** | 7.080011269** | 17.52896625* | 20.30865411* | 34.32245041 |
| 5 | 34.03651111 | 21.00571882* | 7.00091645** | 17.50125361* | 20.17761691* | 33.32542792 |
| 6 | 33.40023016 | 20.82944121* | 6.998101517* | 17.31645469* | 20.02206759* | 32.02687741 |
| 7 | 33.19464436 | 20.73801898* | 6.667267055* | 17.14857212* | 19.96561174* | 31.89977783 |
| 8 | 31.79810219 | 20.72225756* | 6.41264767* | 17.1112964* | 19.73269698* | 31.65582691 |
| 9 | 31.38856415 | 20.66680036* | 6.402981365* | 16.95737784* | 19.35240336* | 31.28312348 |
| 10 | 31.18110833 | 20.59716854* | 6.346202663* | 16.28904283* | 19.32660233* | 31.18062572 |
| 11 | 30.79701224 | 19.73283124 | 6.276672588 | 15.91399412 | 19.30681144 | 30.94742380 |
| 12 | 29.70641873 | 19.39302272 | 6.174176528 | 15.77349266 | 19.16164451 | 30.80509114 |
| 13 | 29.62991189 | 19.16839961 | 6.049106836 | 15.66546601 | 19.15146855 | 30.69879896 |
| 14 | 29.11507633 | 19.00230396 | 5.949620279 | 15.49736507 | 19.00755024 | 30.30301786 |
| 15 | 28.77899934 | 18.96921029 | 5.916144649 | 15.42113149 | 18.66648676 | 30.17556457 |
| 16 | 28.50439241 | 18.85721685 | 5.899104326 | 15.42091807 | 18.36832924 | 29.57328465 |
| 17 | 28.12754467 | 18.85612228 | 5.833222822 | 15.36859564 | 18.03252705 | 28.90537394 |
| 18 | 27.84328622* | 18.71036368 | 5.796981155 | 15.35453221 | 17.99668339 | 28.88559694* |
| 19 | 27.83228653** | 18.54703092 | 5.700099586 | 15.138358 | 17.86651482 | 28.73094957* |
| 20 | 27.52136118** | 18.15280259 | 5.688524342 | 15.09936505 | 17.85903462 | 27.81910123* |
| 21 | 26.29805725* | 17.99984458 | 5.645905767 | 15.07957857 | 17.65569396 | 27.67342355* |
| 22 | 26.10845601* | 17.91003118 | 5.524528875 | 15.07648811 | 17.49262619 | 26.44106603* |
| 23 | 25.48402534* | 17.76201632 | 5.481310842 | 14.94202199 | 17.45198987 | 26.31788321* |
| 24 | 25.38227884* | 17.54752246 | 5.130247918 | 14.92941659 | 17.11122032 | 26.09486339* |
| 25 | 25.15511974* | 16.94444234 | 4.990858497 | 14.77156567 | 17.10154035 | 25.96259878* |
| 26 | 24.46553389** | 16.79825564 | 4.638800894 | 14.49695313 | 16.61462489 | 25.47698011* |
| 27 | 23.32024065* | 15.72007725 | 4.084813309 | 12.73556444 | 16.50485303 | 24.92839872* |

| | 1. Mult drawn mean 60.5±15.5 days pregnant | | | | 2. Individual patient mean 54.5±15 days pregnant | | |
|---|---|---|---|---|---|---|---|
| Score | True outcome | Patient no | Gest age | Score | True outcome | Patient no | Gest age |
| 6 | p | Patient 8 | 52 | 6 | p | Patient 8 | 52 |
| 6 | p | Patient 17 | 71 | 6 | p | Patient 17 | 71 |
| 5 | p | Patient 13 | 67 | 5 | p | Patient 13 | 67 |
| 5 | p | Patient 3 | 80 | 4 | h | Patient 13 | 57 |
| 4 | p | Patient 1 | 37 | 4 | p | Patient 1 | 37 |
| 4 | p | Patient 3 | 38 | 4 | h | Patient 6 | 48 |
| 4 | h | Patient 6 | 48 | 4 | p | Patient 11 | 57 |
| 4 | p | Patient 11 | 57 | 4 | p | Patient 3 | 38 |
| 4 | h | Patient 13 | 57 | 3 | p | Patient 5 | 48 |
| 3 | h | Patient 4 | 43 | 3 | h | Patient 4 | 43 |
| 3 | p | Patient 5 | 48 | 3 | h | Patient 9 | 53 |
| 3 | h | Patient 9 | 53 | 2 | h | Patient 2 | 33 |
| 3 | p | Patient 3 | 57 | 2 | h | Patient 14 | 60 |
| 3 | p | Patient 3 | 69 | 2 | h | Patient 10 | 54 |
| 3 | h | Patient 8 | 69 | 1 | h | Patient 7 | 38 |
| 3 | h | Patient 6 | 85 | 1 | h | Patient 12 | 57 |
| 2 | h | Patient 2 | 33 | 0 | h | Patient 4 | 68 |
| 2 | h | Patient 10 | 54 | 0 | h | Patient 15 | 82 |
| 2 | h | Patient 14 | 60 | 0 | h | Patient 16 | 89 |
| 2 | p | Patient 1 | 63 | | | | |
| 2 | h | Patient 14 | 81 | | | | |
| 1 | h | Patient 7 | 38 | | | | |
| 1 | h | Patient 12 | 57 | | | | |
| 0 | h | Patient 4 | 68 | | | | |
| 0 | h | Patient 16 | 69 | | | | |
| 0 | h | Patient 9 | 72 | | | | |
| 0 | h | Patient 15 | 82 | | | | |
| 0 | h | Patient 10 | 83 | | | | |

| | Top bidirectional (A&B) movers | | Unidirectional mover (A or B) | A↑ alone | A↓ alone | B↑ alone | B↓ alone | Before IWG A or B predictor | After IWG A or B predictor | A group high (+) | B group high (-) |
|---|---|---|---|---|---|---|---|---|---|---|---|
| | A↑ B↓ | A↓ B↑ | | | | | | | | | |
| miR-513a-5p | x | | | | | | | | | | |
| miR-545 | x | | | | | | | | | | |
| miR-548a-5p | | x | | | | | | x | | x | x |
| miR-574-5p | x | | | | | | | x | | x | |
| miR-582-3p | | x | | | | | | x | | x | |
| miR-590-5p | x | | | | | | | | | | x |
| miR-1 | | | | x | | | | x | | | |
| miR-1229 | | | | | | | | | | | |
| miR-1244 | | | | | | | | | | | |
| miR-1267 | | | | | | | | | | | |
| miR-133b | | | | | | | | | | | |
| miR-199b | | | | | | | | | | | |
| miR-210 | | | | | | | | | | | |
| miR-221-5p | | | | | | | | | | | |
| miR-370 | | | | | | | | | | | |
| miR-410 | | | | x | | | | | | | |
| miR-424-5p | | | | | x | | | | x | | |
| miR-575 | | | | | | | | | | | |
| miR-671-5p | | | | | | | | | | | |
| miR-7-1-3p | | | | | | | | | | | |
| miR-99b-5p | | | | | | | x | | | | |
| 1470 | | | | | | | | | | | |
| miR-155 | | | | | | | | | | | |
| miR-181a-3p | | | | | | | | | | | |
| miR-223-5p | | | | | | | | | | | |
| miR-129Sa | | | | | x | | | | | | |
| miR-630 | | | | | | | | | | | |
| miR-671-5p | | | | | | | | | | | |

| | A | B | C | D | E |
|---|---|---|---|---|---|
| Key: ↑ MM increased, ↓ MM decreased, H=Healthy, P=Preeclampsia, M=Miscarriage | | (XX) H↓P↑ from top 25s / (X) H↓P↑ from top 100s | (XX) H↑M↓ from top 25s / (X) H↑M↓ from top 100s | (XX) H↓M↑ from top 25s / (X) H↓M↑ from top 100s | Reference from Table 22: miR/Group A → response to WGS category / (XX) from top 25s / (X) from top 100s |
| 1. | miR-144-3p | xx | | | xx |
| 2. | miR-582-5p | xx | | | xx |
| 3. | miR-30e-3p | xx | | | x |
| 4. | miR-340-5p | xx | | x | x |
| 5. | miR-424-5p | xx | | | x |
| 6. | miR-199a-5p | xx | | | |
| 7. | miR-199b-5p | xx | | | |
| 8. | miR-210 | xx | | | |
| 9. | miR-221-3p | xx | | | |
| 10. | miR-33a-5p | xx | | | |
| 11. | miR-575 | xx | | | |
| 12. | miR-7-5p | | | | |
| 13. | miR-1229 | | xx | | |
| 14. | miR-1267 | | xx | | |
| 15. | miR-671-3p | | xx | | |

| | Diff "Before IVIG" Mean Healthy-Mean Preec | Mean Before Healthy | Mean Before Preec | Diff | Diff "Before IVIG" Mean Healthy-Mean Miscarriage | Mean Before Healthy | Mean Before Miscarriage | Diff |
|---|---|---|---|---|---|---|---|---|
| 1. | hsa-miR-609 | 3.556648 | 0.091103 | 3.465546 | NC1_0000215 | 5.534493024 | -0.03373 | 5.568228 |
| 2. | hsa-miR-520d-3p | 2.807154 | 0.091103 | 2.716051 | hsa-miR-557 | 1.531374545 | -2.91744 | 4.448815 |
| 3. | hsa-miR-877-3p | 2.482689 | -0.16059 | 2.643281 | hsa-miR-1244 | 3.748555627 | -0.20282 | 3.951379 |
| 4. | hsa-miR-658 | 2.668746 | 0.147621 | 2.521125 | hsa-miR-876-3p | 2.580118356 | -1.34163 | 3.921746 |
| 5. | hsa-miR-671-3p | 2.494625 | 0.081406 | 2.413219 | hsa-miR-609 | 3.556648318 | -0.09025 | 3.646901 |
| 6. | hsa-miR-196a-5p | 1.511198 | -0.85327 | 2.36447 | hsa-miR-1825 | 1.125520995 | -2.20438 | 3.329593 |
| 7. | NC1_0000215 | 5.534492 | 3.321342 | 2.233151 | hsa-miR-760 | 2.115653943 | -1.16751 | 3.283147 |
| 8. | hsa-miR-588 | 1.783329 | -0.24944 | 2.03277 | hsa-let-7b-5p | 1.180341993 | -2.08466 | 3.265001 |
| 9. | hsa-miR-548d-5p | 1.287321 | -0.62095 | 1.908269 | hsa-miR-149-5p | 1.227844976 | -2.00968 | 3.237529 |
| 10. | hsa-miR-1244 | 3.748556 | 1.861274 | 1.887282 | hsa-let-7f-1-3p | 1.110498317 | -2.11879 | 3.229286 |
| 11. | hsa-miR-550a-3p | 0.9307 | -0.89444 | 1.825137 | hsa-miR-933 | 1.196517413 | -2.01289 | 3.209403 |
| 12. | hsa-miR-191a-5p | 0.665019 | -1.04804 | 1.713055 | hsa-miR-1539 | 1.350064004 | -1.8546 | 3.204667 |
| 13. | hsa-miR-1470 | 1.733619 | 0.04273 | 1.690868 | hsa-miR-563 | 0.983771638 | -2.20872 | 3.192094 |
| 14. | hsa-miR-129-2-3p | 1.999632 | 0.326515 | 1.673117 | hsa-miR-129-2-3p | 1.999632068 | -1.17664 | 3.176268 |
| 15. | ebv-miR-BART15 | 1.618116 | -0.00996 | 1.628074 | hsv1-miR-H6-3p | 1.229159283 | -1.87237 | 3.101533 |
| 16. | kshv-miR-K12-12* | 1.682717 | 0.091103 | 1.591615 | hsa-miR-1281 | 1.401101813 | -1.69442 | 3.095523 |
| 17. | hsa-miR-1257 | 1.659302 | 0.147621 | 1.511682 | hsa-miR-190b | 3.083119458 | 0.025053 | 3.058066 |
| 18. | hsa-miR-129-5p | 1.539384 | 0.051742 | 1.487641 | hsa-miR-432-3p | 1.686464728 | -1.35532 | 3.039464 |
| 19. | hsa-miR-557 | 1.531373 | 0.11115 | 1.420225 | hsa-miR-591 | 2.980426041 | -0.03373 | 3.014161 |
| 20. | hsa-miR-602 | 1.124326 | -0.28154 | 1.405862 | hsa-miR-548m | 2.820033742 | -0.18162 | 3.001951 |
| 21. | hsa-miR-34b-3p | 1.495525 | 0.091103 | 1.404422 | hsa-miR-92b-3p | 0.701754683 | -2.23093 | 2.932681 |
| 22. | hsa-miR-563 | 0.983372 | -0.39492 | 1.378291 | hsa-miR-520d-3p | 2.807154102 | -0.09025 | 2.897402 |
| 23. | hsa-miR-654-3p | -0.98238 | -2.34452 | 1.361945 | hsa-miR-33b-3p | 1.275329512 | -1.5972 | 2.872527 |
| 24. | hsa-miR-99a-3p | 1.48656 | 0.147621 | 1.333894 | hsa-miR-425-3p | 1.264991165 | -1.60025 | 2.86524 |
| 25. | kshv-miR-K12-1 | 1.474166 | 0.147621 | 1.326645 | hsa-miR-593-3p | 2.807139874 | -0.03373 | 2.840875 |

FIG. 21

| | Diff "Before IVIG" Mean Healthy-Mean Preec | Mean Before Healthy | Mean Before Preec | Diff | Diff "Before IVIG" Mean Healthy-Mean Miscarriage | Mean Before Healthy | Mean Before Miscarriage | Diff |
|---|---|---|---|---|---|---|---|---|
| 1 | hsa-miR-128 | -2.92329 | -0.13201 | -2.79128 | hsa-miR-629-5p | -2.28113012 | 1.430793 | -3.71193 |
| 2 | hsa-miR-365a-3p | -3.46924 | -0.65862 | -2.81062 | hsa-miR-99b-5p | -1.379151954 | 2.33087 | -3.73002 |
| 3 | hsa-miR-181c-5p | -2.67784 | 0.218005 | -2.89585 | hsa-miR-7-1-3p | -3.66722573 | 0.062864 | -3.73314 |
| 4 | hsa-miR-99a-3p | -3.11797 | -0.12451 | -2.99346 | hsa-miR-125a-5p | -2.591287473 | 1.146591 | -3.73788 |
| 5 | hsa-miR-221-5p | -3.1991 | -0.2049 | -2.9942 | hsa-miR-7-5p | -3.199718366 | 0.599649 | -3.79937 |
| 6 | hsa-miR-152 | -2.61774 | 0.41265 | -3.03039 | hsa-miR-362a-3p | -3.469238471 | 0.344892 | -3.81413 |
| 7 | hsa-miR-665 | -0.56973 | 2.471473 | -3.04121 | hsa-miR-424-5p | -3.46197997 | 0.363093 | -3.82507 |
| 8 | hsa-miR-338-3p | -3.63586 | -0.54126 | -3.0946 | hsa-miR-340-3p | -3.577283913 | 0.28484 | -3.86212 |
| 9 | hsa-miR-210 | -3.42117 | -0.3216 | -3.09957 | hsa-miR-423-5p | -3.714991637 | 0.207289 | -3.92228 |
| 10 | hsa-miR-532-5p | -3.65228 | -0.51087 | -3.14142 | hsa-miR-483-5p | -3.209448978 | 0.731046 | -3.9405 |
| 11 | hsa-miR-340-3p | -3.57728 | -0.42253 | -3.15475 | hsa-miR-96-5p | -3.157413155 | 0.796971 | -3.9438 |
| 12 | hsa-miR-199b-5p | -3.9291 | -0.72521 | -3.21389 | hsa-miR-338-3p | -3.635855737 | 0.370369 | -4.00642 |
| 13 | hsa-miR-362-3p | -3.03915 | 0.18562 | -3.22477 | hsa-miR-32-3p | -1.998712583 | 2.02635 | -4.02206 |
| 14 | hsa-miR-136-5p | -1.68987 | 1.560481 | -3.25035 | hsa-miR-133b | 0.347828087 | 4.461789 | -4.11396 |
| 15 | hsa-miR-582-5p | -3.92764 | -0.67487 | -3.25278 | hsa-miR-144-3p | -3.4324734 | 0.689897 | -4.12237 |
| 16 | hsa-miR-18a-5p | -3.26451 | -0.00607 | -3.25844 | hsa-miR-450a-5p | -2.56363075 | 1.637885 | -4.20352 |
| 17 | hiv1-miR-H1 | -1.19427 | 2.113461 | -3.30783 | hsa-miR-1249 | -3.648934932 | 0.584227 | -4.23316 |
| 18 | hsa-miR-575 | -3.49217 | -0.14572 | -3.34645 | hsa-miR-340-5p | -4.155538283 | 0.184575 | -4.34011 |
| 19 | hsa-miR-95 | -2.67179 | 0.696189 | -3.36798 | hsa-miR-199b-5p | -3.93910499 | 0.451091 | -4.3902 |
| 20 | hsa-miR-30e-3p | -4.19223 | -0.80857 | -3.38365 | hsa-miR-148a-3p | -3.79779434 | 0.664992 | -4.46229 |
| 21 | hsa-miR-340-5p | -4.15534 | -0.66089 | -3.49464 | hsa-miR-301a-3p | -4.54215253 | -0.05789 | -4.48426 |
| 22 | hsa-miR-17-3p | -3.21421 | 0.29928 | -3.51344 | hsa-miR-30e-3p | -4.192225473 | 0.303459 | -4.49568 |
| 23 | hsa-miR-148a-3p | -3.79979 | -0.14621 | -3.65159 | hsa-miR-582-5p | -3.927643047 | 0.706488 | -4.6413 |
| 24 | hsa-miR-144-3p | -3.43247 | 0.242774 | -3.67325 | hsa-miR-1 | -0.804063357 | 3.989321 | -4.79338 |
| 25 | hsa-miR-301a-3p | -4.54215 | -0.22431 | -4.31784 | hsa-miR-144-5p | -3.795031715 | 1.449947 | -5.24498 |

FIG. 22

SEQUENCE LISTING

<160> NUMBER OF SEQ ID NOS: 191

<210> SEQ ID NO 1
<211> LENGTH: 22
<212> TYPE: RNA
<213> ORGANISM: homo sapiens
<223> OTHER INFORMATION: hsa-miR-582-3p MIMAT0004797

<400> SEQUENCE: 1
uaacugguug aacaacugaa cc                                              22

<210> SEQ ID NO 2
<211> LENGTH: 22
<212> TYPE: RNA
<213> ORGANISM: homo sapiens
<223> OTHER INFORMATION: hsa-miR-7-1-3p MIMAT0004553

<400> SEQUENCE: 2
caacaaauca cagucugcca ua                                              22

<210> SEQ ID NO 3
<211> LENGTH: 22
<212> TYPE: RNA
<213> ORGANISM: homo sapiens
<223> OTHER INFORMATION: hsa-miR-340-5p MIMAT0004692

<400> SEQUENCE: 3
uuauaaagca augagacuga uu                                              22

<210> SEQ ID NO 4
<211> LENGTH: 22
<212> TYPE: RNA
<213> ORGANISM: homo sapiens
<223> OTHER INFORMATION: hsa-miR-199b-3p MIMAT0004563

<400> SEQUENCE: 4
acaguagucu gcacauuggu ua                                              22

<210> SEQ ID NO 5
<211> LENGTH: 22
<212> TYPE: RNA
<213> ORGANISM: homo sapiens
<223> OTHER INFORMATION: hsa-miR-199a-3p MIMAT0000232

<400> SEQUENCE: 5
acaguagucu gcacauuggu ua                                              22

<210> SEQ ID NO 6
<211> LENGTH: 22
<212> TYPE: RNA
<213> ORGANISM: homo sapiens
<223> OTHER INFORMATION: hsa-miR-30e-5p MIMAT0000692

<400> SEQUENCE: 6
uguaaacauc cuugacugga ag                                              22

<210> SEQ ID NO 7
<211> LENGTH: 19
<212> TYPE: RNA
<213> ORGANISM: homo sapiens
<223> OTHER INFORMATION: hsa-miR-575 MIMAT0003240

<400> SEQUENCE: 7
gagccaguug gacaggagc                                                  19

```
<210> SEQ ID NO 8
<211> LENGTH: 23
<212> TYPE: RNA
<213> ORGANISM: homo sapiens
<223> OTHER INFORMATION: hsa-miR-7-5p MIMAT0000252

<400> SEQUENCE: 8
uggaagacua gugauuuugu ugu                                              23

<210> SEQ ID NO 9
<211> LENGTH: 22
<212> TYPE: RNA
<213> ORGANISM: homo sapiens
<223> OTHER INFORMATION: hsa-miR-33a-3p MIMAT0004506

<400> SEQUENCE: 9
caauguuucc acagugcauc ac                                               22

<210> SEQ ID NO 10
<211> LENGTH: 22
<212> TYPE: RNA
<213> ORGANISM: homo sapiens
<223> OTHER INFORMATION: hsa-miR-7-2-3p MIMAT0004554

<400> SEQUENCE: 10
caacaaaucc cagucuaccu aa                                               22

<210> SEQ ID NO 11
<211> LENGTH: 23
<212> TYPE: RNA
<213> ORGANISM: homo sapiens
<223> OTHER INFORMATION: hsa-miR-199b-5p MIMAT0000263

<400> SEQUENCE: 11
cccaguguuu agacuaucug uuc                                              23

<210> SEQ ID NO 12
<211> LENGTH: 22
<212> TYPE: RNA
<213> ORGANISM: homo sapiens
<223> OTHER INFORMATION: hsa-miR-144-5p MIMAT0004600

<400> SEQUENCE: 12
ggauaucauc auauacugua ag                                               22

<210> SEQ ID NO 13
<211> LENGTH: 22
<212> TYPE: RNA
<213> ORGANISM: homo sapiens
<223> OTHER INFORMATION: hsa-miR-30e-3p MIMAT0000693

<400> SEQUENCE: 13
cuuucagucg gauguuuaca gc                                               22

<210> SEQ ID NO 14
<211> LENGTH: 21
<212> TYPE: RNA
<213> ORGANISM: homo sapiens
<223> OTHER INFORMATION: hsa-miR-424-3p MIMAT0004749

<400> SEQUENCE: 14
caaaacguga ggcgcugcua u                                                21

<210> SEQ ID NO 15
```

```
<211> LENGTH: 21
<212> TYPE: RNA
<213> ORGANISM: homo sapiens
<223> OTHER INFORMATION: hsa-miR-33a-5p MIMAT0000091

<400> SEQUENCE: 15
gugcauugua guugcauugc a                                              21

<210> SEQ ID NO 16
<211> LENGTH: 21
<212> TYPE: RNA
<213> ORGANISM: homo sapiens
<223> OTHER INFORMATION: hsa-miR-671-3p MIMAT0004819

<400> SEQUENCE: 16
uccgguucuc agggcuccac c                                              21

<210> SEQ ID NO 17
<211> LENGTH: 22
<212> TYPE: RNA
<213> ORGANISM: homo sapiens
<223> OTHER INFORMATION: hsa-miR-340-3p MIMAT0000750

<400> SEQUENCE: 17
uccgucucag uuacuuuaua gc                                             22

<210> SEQ ID NO 18
<211> LENGTH: 21
<212> TYPE: RNA
<213> ORGANISM: homo sapiens
<223> OTHER INFORMATION: hsa-miR-1267 MIMAT0005921

<400> SEQUENCE: 18
ccuguugaag uguaaucccc a                                              21

<210> SEQ ID NO 19
<211> LENGTH: 23
<212> TYPE: RNA
<213> ORGANISM: homo sapiens
<223> OTHER INFORMATION: hsa-miR-1229-3p MIMAT0005584

<400> SEQUENCE: 19
cucucaccac ugcccuccca cag                                            23

<210> SEQ ID NO 20
<211> LENGTH: 22
<212> TYPE: RNA
<213> ORGANISM: homo sapiens
<223> OTHER INFORMATION: hsa-miR-424-5p MIMAT0001341

<400> SEQUENCE: 20
cagcagcaau ucauguuuug aa                                             22

<210> SEQ ID NO 21
<211> LENGTH: 23
<212> TYPE: RNA
<213> ORGANISM: homo sapiens
<223> OTHER INFORMATION: hsa-miR-221-3p MIMAT0000278

<400> SEQUENCE: 21
agcuacauug ucugcugggu uuc                                            23

<210> SEQ ID NO 22
<211> LENGTH: 22
<212> TYPE: RNA
```

```
<213> ORGANISM: homo sapiens
<223> OTHER INFORMATION: hsa-miR-1 MIMAT0000416

<400> SEQUENCE: 22
uggaauguaa agaaguaugu au                                            22

<210> SEQ ID NO 23
<211> LENGTH: 22
<212> TYPE: RNA
<213> ORGANISM: homo sapiens
<223> OTHER INFORMATION: hsa-miR-133b MIMAT0000770

<400> SEQUENCE: 23 uuugguccccc uucaaccagc ua                                           22

<210> SEQ ID NO 24
<211> LENGTH: 22
<212> TYPE: RNA
<213> ORGANISM: homo sapiens
<223> OTHER INFORMATION: hsa-miR-221-5p MIMAT0004568

<400> SEQUENCE: 24
accuggcaua caauguagau uu                                            22

<210> SEQ ID NO 25
<211> LENGTH: 22
<212> TYPE: RNA
<213> ORGANISM: homo sapiens
<223> OTHER INFORMATION: hsa-miR-210 MIMAT0000267

<400> SEQUENCE: 25
cugugcgugu gacagcggcu ga                                            22

<210> SEQ ID NO 26
<211> LENGTH: 24
<212> TYPE: RNA
<213> ORGANISM: homo sapiens
<223> OTHER INFORMATION: hsa-miR-1229-5p MIMAT0022942

<400> SEQUENCE: 26
guggguaggg uuuggggggag agcg                                         24

<210> SEQ ID NO 27
<211> LENGTH: 23
<212> TYPE: RNA
<213> ORGANISM: homo sapiens
<223> OTHER INFORMATION: hsa-miR-671-5p MIMAT0003880

<400> SEQUENCE: 27
aggaagcccu ggaggggcug gag                                           23

<210> SEQ ID NO 28
<211> LENGTH: 23
<212> TYPE: RNA
<213> ORGANISM: homo sapiens
<223> OTHER INFORMATION: hsa-miR-582-5p MIMAT0003247

<400> SEQUENCE: 28
uuacaguugu ucaaccaguu acu                                           23

<210> SEQ ID NO 29
<211> LENGTH: 23
<212> TYPE: RNA
<213> ORGANISM: homo sapiens
<223> OTHER INFORMATION: hsa-miR-199a-5p MIMAT0000231
```

```
<400> SEQUENCE: 29
cccaguguuc agacuaccug uuc                                    23

<210> SEQ ID NO 30
<211> LENGTH: 20
<212> TYPE: RNA
<213> ORGANISM: homo sapiens
<223> OTHER INFORMATION: hsa-miR-144-3p MIMAT0000436

<400> SEQUENCE: 30
uacaguauag augauguacu                                        20

<210> SEQ ID NO 31
<211> LENGTH: 22
<212> TYPE: RNA
<213> ORGANISM: homo sapiens
<223> OTHER INFORMATION: hsa-miR-376a-5p MIMAT0003386

<400> SEQUENCE: 31
guagauucuc cuucuaugag ua                                     22

<210> SEQ ID NO 32
<211> LENGTH: 22
<212> TYPE: RNA
<213> ORGANISM: homo sapiens
<223> OTHER INFORMATION: hsa-miR-193a-3p MIMAT0000459

<400> SEQUENCE: 32
aacuggccua caaaguccca gu                                     22

<210> SEQ ID NO 33
<211> LENGTH: 23
<212> TYPE: RNA
<213> ORGANISM: homo sapiens
<223> OTHER INFORMATION: hsa-miR-557 MIMAT0003221

<400> SEQUENCE: 33
guuugcacgg gugggccuug ucu                                    23

<210> SEQ ID NO 34
<211> LENGTH: 22
<212> TYPE: RNA
<213> ORGANISM: homo sapiens
<223> OTHER INFORMATION: hsa-miR-34a-3p MIMAT0004557

<400> SEQUENCE: 34
caaucagcaa guauacugcc cu                                     22

<210> SEQ ID NO 35
<211> LENGTH: 22
<212> TYPE: RNA
<213> ORGANISM: homo sapiens
<223> OTHER INFORMATION: hsa-miR-584-5p MIMAT0003249

<400> SEQUENCE: 35
uuaugguuug ccugggacug ag                                     22

<210> SEQ ID NO 36
<211> LENGTH: 26
<212> TYPE: RNA
<213> ORGANISM: homo sapiens
<223> OTHER INFORMATION: hsa-miR-1244 MIMAT0005896

<400> SEQUENCE: 36
```

-continued

```
aaguaguugg uuuguaugag augguu                                          26

<210> SEQ ID NO 37
<211> LENGTH: 22
<212> TYPE: RNA
<213> ORGANISM: homo sapiens
<223> OTHER INFORMATION: hsa-miR-125b-1-3p MIMAT0004592

<400> SEQUENCE: 37 acgguuagg cucuugggag cu                                               22

<210> SEQ ID NO 38
<211> LENGTH: 22
<212> TYPE: RNA
<213> ORGANISM: homo sapiens
<223> OTHER INFORMATION: hsa-miR-32-3p MIMAT0004505

<400> SEQUENCE: 38
caauuuagug ugugugauau uu                                              22

<210> SEQ ID NO 39
<211> LENGTH: 22
<212> TYPE: RNA
<213> ORGANISM: homo sapiens
<223> OTHER INFORMATION: hsa-miR-933 MIMAT0004976

<400> SEQUENCE: 39
ugugcgcagg gagaccucuc cc                                              22

<210> SEQ ID NO 40
<211> LENGTH: 22
<212> TYPE: RNA
<213> ORGANISM: homo sapiens
<223> OTHER INFORMATION: hsa-miR-373-5p MIMAT0000725

<400> SEQUENCE: 40
acucaaaaug ggggcgcuuu cc                                              22

<210> SEQ ID NO 41
<211> LENGTH: 22
<212> TYPE: RNA
<213> ORGANISM: homo sapiens
<223> OTHER INFORMATION: hsa-let-7b-5p MIMAT0000063

<400> SEQUENCE: 41
ugagguagua gguugugugg uu                                              22

<210> SEQ ID NO 42
<211> LENGTH: 21
<212> TYPE: RNA
<213> ORGANISM: homo sapiens
<223> OTHER INFORMATION: hsa-miR-376a-3p MIMAT0000729

<400> SEQUENCE: 42
aucauagagg aaaauccacg u                                               21

<210> SEQ ID NO 43
<211> LENGTH: 22
<212> TYPE: RNA
<213> ORGANISM: homo sapiens
<223> OTHER INFORMATION: hsa-miR-129-2-3p MIMAT0004605

<400> SEQUENCE: 43
aagcccuuac cccaaaaagc au                                              22
```

```
<210> SEQ ID NO 44
<211> LENGTH: 22
<212> TYPE: RNA
<213> ORGANISM: homo sapiens
<223> OTHER INFORMATION: hsa-miR-548am-3p MIMAT0019076

<400> SEQUENCE: 44
caaaaacugc aguuacuuuu gu                                              22

<210> SEQ ID NO 45
<211> LENGTH: 22
<212> TYPE: RNA
<213> ORGANISM: homo sapiens
<223> OTHER INFORMATION: hsa-let-7f-5p MIMAT0000067

<400> SEQUENCE: 45
ugagguagua gauuguauag uu                                              22

<210> SEQ ID NO 46
<211> LENGTH: 22
<212> TYPE: RNA
<213> ORGANISM: homo sapiens
<223> OTHER INFORMATION: hsa-miR-876-3p MIMAT0004925

<400> SEQUENCE: 46
uggugguuua caaaguaauu ca                                              22

<210> SEQ ID NO 47
<211> LENGTH: 20
<212> TYPE: RNA
<213> ORGANISM: homo sapiens
<223> OTHER INFORMATION: hsa-miR-371a-5p MIMAT0004687

<400> SEQUENCE: 47
acucaaacug uggggggcacu                                                20

<210> SEQ ID NO 48
<211> LENGTH: 23
<212> TYPE: RNA
<213> ORGANISM: homo sapiens
<223> OTHER INFORMATION: hsa-miR-423-5p MIMAT0004748

<400> SEQUENCE: 48
ugaggggcag agagcgagac uuu                                             23

<210> SEQ ID NO 49
<211> LENGTH: 23
<212> TYPE: RNA
<213> ORGANISM: homo sapiens
<223> OTHER INFORMATION: hsa-miR-373-3p MIMAT0000726

<400> SEQUENCE: 49
gaagugcuuc gauuuugggg ugu                                             23

<210> SEQ ID NO 50
<211> LENGTH: 21
<212> TYPE: RNA
<213> ORGANISM: homo sapiens
<223> OTHER INFORMATION: hsa-miR-152 MIMAT0000438

<400> SEQUENCE: 50
ucagugcaug acagaacuug g                                               21
```

```
<210> SEQ ID NO 51
<211> LENGTH: 22
<212> TYPE: RNA
<213> ORGANISM: homo sapiens
<223> OTHER INFORMATION: hsa-miR-34a-5p MIMAT0000255

<400> SEQUENCE: 51
uggcaguguc uuagcugguu gu                                    22

<210> SEQ ID NO 52
<211> LENGTH: 23
<212> TYPE: RNA
<213> ORGANISM: homo sapiens
<223> OTHER INFORMATION: hsa-miR-335-5p MIMAT0000765

<400> SEQUENCE: 52
ucaagagcaa uaacgaaaaa ugu                                   23

<210> SEQ ID NO 53
<211> LENGTH: 22
<212> TYPE: RNA
<213> ORGANISM: homo sapiens
<223> OTHER INFORMATION: hsa-miR-181c-5p MIMAT0000258

<400> SEQUENCE: 53
aacauucaac cugucgguga gu                                    22

<210> SEQ ID NO 54
<211> LENGTH: 22
<212> TYPE: RNA
<213> ORGANISM: homo sapiens
<223> OTHER INFORMATION: hsa-miR-125b-2-3p MIMAT0004603

<400> SEQUENCE: 54
ucacaaguca ggcucuuggg ac                                    22

<210> SEQ ID NO 55
<211> LENGTH: 22
<212> TYPE: RNA
<213> ORGANISM: homo sapiens
<223> OTHER INFORMATION: hsa-miR-548am-5p MIMAT0022740

<400> SEQUENCE: 55
aaaaguaauu gcgguuuuug cc                                    22

<210> SEQ ID NO 56
<211> LENGTH: 22
<212> TYPE: RNA
<213> ORGANISM: homo sapiens
<223> OTHER INFORMATION: hsa-miR-338-3p MIMAT0000763

<400> SEQUENCE: 56
uccagcauca gugauuuugu ug                                    22

<210> SEQ ID NO 57
<211> LENGTH: 22
<212> TYPE: RNA
<213> ORGANISM: homo sapiens
<223> OTHER INFORMATION: hsa-miR-1225-5p MIMAT0005572

<400> SEQUENCE: 57
guggguacgg cccaguggggg gg                                   22

<210> SEQ ID NO 58
<211> LENGTH: 22
```

```
<212> TYPE: RNA
<213> ORGANISM: homo sapiens
<223> OTHER INFORMATION: hsa-miR-362-3p MIMAT0004683

<400> SEQUENCE: 58
aacacaccua uucaaggauu ca                                          22

<210> SEQ ID NO 59
<211> LENGTH: 23
<212> TYPE: RNA
<213> ORGANISM: homo sapiens
<223> OTHER INFORMATION: hsa-miR-767-5p MIMAT0003882

<400> SEQUENCE: 59
ugcaccaugg uugucugagc aug                                         23

<210> SEQ ID NO 60
<211> LENGTH: 22
<212> TYPE: RNA
<213> ORGANISM: homo sapiens
<223> OTHER INFORMATION: hsa-miR-136-3p MIMAT0004606

<400> SEQUENCE: 60
caucaucguc ucaaaugagu cu                                          22

<210> SEQ ID NO 61
<211> LENGTH: 24
<212> TYPE: RNA
<213> ORGANISM: homo sapiens
<223> OTHER INFORMATION: hsa-miR-29b-1-5p MIMAT0004514

<400> SEQUENCE: 61
gcugguuuca uauggugguu uaga                                        24

<210> SEQ ID NO 62
<211> LENGTH: 22
<212> TYPE: RNA
<213> ORGANISM: homo sapiens
<223> OTHER INFORMATION: hsa-miR-29a-3p MIMAT0000086

<400> SEQUENCE: 62
uagcaccauc ugaaaucggu ua                                          22

<210> SEQ ID NO 63
<211> LENGTH: 22
<212> TYPE: RNA
<213> ORGANISM: homo sapiens
<223> OTHER INFORMATION: hsa-miR-92b-3p MIMAT0003218

<400> SEQUENCE: 63
uauugcacuc gucccggccu cc                                          22

<210> SEQ ID NO 64
<211> LENGTH: 24
<212> TYPE: RNA
<213> ORGANISM: homo sapiens
<223> OTHER INFORMATION: hsa-miR-362-5p MIMAT0000705

<400> SEQUENCE: 64
aauccuugga accaggugu gagu                                         24

<210> SEQ ID NO 65
<211> LENGTH: 22
<212> TYPE: RNA
<213> ORGANISM: homo sapiens
```

<223> OTHER INFORMATION: hsa-miR-223-5p MIMAT0004570

<400> SEQUENCE: 65
cguguauuug acaagcugag uu            22

<210> SEQ ID NO 66
<211> LENGTH: 22
<212> TYPE: RNA
<213> ORGANISM: homo sapiens
<223> OTHER INFORMATION: hsa-miR-505-3p MIMAT0002876

<400> SEQUENCE: 66
cgucaacacu ugcugguuuc cu            22

<210> SEQ ID NO 67
<211> LENGTH: 22
<212> TYPE: RNA
<213> ORGANISM: homo sapiens
<223> OTHER INFORMATION: hsa-miR-634 MIMAT0003304

<400> SEQUENCE: 67
aaccagcacc ccaacuuugg ac            22

<210> SEQ ID NO 68
<211> LENGTH: 23
<212> TYPE: RNA
<213> ORGANISM: homo sapiens
<223> OTHER INFORMATION: hsa-miR-371a-3p MIMAT0000723

<400> SEQUENCE: 68
aagugccgcc aucuuugag ugu            23

<210> SEQ ID NO 69
<211> LENGTH: 22
<212> TYPE: RNA
<213> ORGANISM: homo sapiens
<223> OTHER INFORMATION: hsa-miR-129-1-3p MIMAT0004548

<400> SEQUENCE: 69
aagcccuuac cccaaaaagu au            22

<210> SEQ ID NO 70
<211> LENGTH: 23
<212> TYPE: RNA
<213> ORGANISM: homo sapiens
<223> OTHER INFORMATION: hsa-miR-1238-5p MIMAT0022947

<400> SEQUENCE: 70
gugaguggga gccccagugu gug           23

<210> SEQ ID NO 71
<211> LENGTH: 22
<212> TYPE: RNA
<213> ORGANISM: homo sapiens
<223> OTHER INFORMATION: hsa-miR-876-5p MIMAT0004924

<400> SEQUENCE: 71
uggauuucuu ugugaaucac ca            22

<210> SEQ ID NO 72
<211> LENGTH: 22
<212> TYPE: RNA
<213> ORGANISM: homo sapiens
<223> OTHER INFORMATION: hsa-miR-181c-3p MIMAT0004559

-continued

```
<400> SEQUENCE: 72
aaccaucgac cguugagugg ac                                        22

<210> SEQ ID NO 73
<211> LENGTH: 22
<212> TYPE: RNA
<213> ORGANISM: homo sapiens
<223> OTHER INFORMATION: hsa-miR-338-5p MIMAT0004701

<400> SEQUENCE: 73
aacaauaucc uggugcugag ug                                        22

<210> SEQ ID NO 74
<211> LENGTH: 22
<212> TYPE: RNA
<213> ORGANISM: homo sapiens
<223> OTHER INFORMATION: hsa-miR-505-5p MIMAT0004776

<400> SEQUENCE: 74
gggagccagg aaguauugau gu                                        22

<210> SEQ ID NO 75
<211> LENGTH: 22
<212> TYPE: RNA
<213> ORGANISM: homo sapiens
<223> OTHER INFORMATION: hsa-miR-335-3p MIMAT0004703

<400> SEQUENCE: 75
uuuuucauua uugcuccuga cc                                        22

<210> SEQ ID NO 76
<211> LENGTH: 22
<212> TYPE: RNA
<213> ORGANISM: homo sapiens
<223> OTHER INFORMATION: hsa-miR-543 MIMAT0004954

<400> SEQUENCE: 76
aaacauucgc ggugcacuuc uu                                        22

<210> SEQ ID NO 77
<211> LENGTH: 22
<212> TYPE: RNA
<213> ORGANISM: homo sapiens
<223> OTHER INFORMATION: hsa-miR-223-3p MIMAT0000280

<400> SEQUENCE: 77
ugucaguuug ucaaauaccc ca                                        22

<210> SEQ ID NO 78
<211> LENGTH: 22
<212> TYPE: RNA
<213> ORGANISM: homo sapiens
<223> OTHER INFORMATION: hsa-miR-125b-5p MIMAT0000423

<400> SEQUENCE: 78
ucccugagac ccuaacuugu ga                                        22

<210> SEQ ID NO 79
<211> LENGTH: 20
<212> TYPE: RNA
<213> ORGANISM: homo sapiens
<223> OTHER INFORMATION: hsa-miR-1238-3p MIMAT0005593

<400> SEQUENCE: 79
```

```
cuuccucguc ugucugcccc                                              20
```

<210> SEQ ID NO 80
<211> LENGTH: 22
<212> TYPE: RNA
<213> ORGANISM: homo sapiens
<223> OTHER INFORMATION: hsa-miR-377-5p MIMAT0004689

<400> SEQUENCE: 80

```
agagguugcc cuuggugaau uc                                           22
```

<210> SEQ ID NO 81
<211> LENGTH: 22
<212> TYPE: RNA
<213> ORGANISM: homo sapiens
<223> OTHER INFORMATION: hsa-miR-584-3p MIMAT0022708

<400> SEQUENCE: 81

```
ucaguuccag gccaaccagg cu                                           22
```

<210> SEQ ID NO 82
<211> LENGTH: 22
<212> TYPE: RNA
<213> ORGANISM: homo sapiens
<223> OTHER INFORMATION: hsa-miR-22-5p MIMAT0004495

<400> SEQUENCE: 82

```
aguucuucag uggcaagcuu ua                                           22
```

<210> SEQ ID NO 83
<211> LENGTH: 21
<212> TYPE: RNA
<213> ORGANISM: homo sapiens
<223> OTHER INFORMATION: hsa-miR-376a-2-5p MIMAT0022928

<400> SEQUENCE: 83

```
gguagauuuu ccuucuaugg u                                            21
```

<210> SEQ ID NO 84
<211> LENGTH: 22
<212> TYPE: RNA
<213> ORGANISM: homo sapiens
<223> OTHER INFORMATION: hsa-miR-301a-5p MIMAT0022696

<400> SEQUENCE: 84

```
gcucugacuu uauugcacua cu                                           22
```

<210> SEQ ID NO 85
<211> LENGTH: 21
<212> TYPE: RNA
<213> ORGANISM: homo sapiens
<223> OTHER INFORMATION: hsa-miR-548m MIMAT0005917

<400> SEQUENCE: 85

```
caaagguauu ugugguuuuu g                                            21
```

<210> SEQ ID NO 86
<211> LENGTH: 23
<212> TYPE: RNA
<213> ORGANISM: homo sapiens
<223> OTHER INFORMATION: hsa-miR-29b-3p MIMAT0000100

<400> SEQUENCE: 86

```
uagcaccauu ugaaaucagu guu                                          23
```

```
<210> SEQ ID NO 87
<211> LENGTH: 22
<212> TYPE: RNA
<213> ORGANISM: homo sapiens
<223> OTHER INFORMATION: hsa-miR-99a-3p MIMAT0004511

<400> SEQUENCE: 87
caagcucgcu ucuauggguc ug                                              22

<210> SEQ ID NO 88
<211> LENGTH: 22
<212> TYPE: RNA
<213> ORGANISM: homo sapiens
<223> OTHER INFORMATION: hsa-miR-33b-3p MIMAT0004811

<400> SEQUENCE: 88
cagugccucg gcagugcagc cc                                              22

<210> SEQ ID NO 89
<211> LENGTH: 22
<212> TYPE: RNA
<213> ORGANISM: homo sapiens
<223> OTHER INFORMATION: hsa-miR-92b-5p MIMAT0004792

<400> SEQUENCE: 89
agggacggga cgcggugcag ug                                              22

<210> SEQ ID NO 90
<211> LENGTH: 23
<212> TYPE: RNA
<213> ORGANISM: homo sapiens
<223> OTHER INFORMATION: hsa-miR-602 MIMAT0003270

<400> SEQUENCE: 90
gacacgggcg acagcugcgg ccc                                             23

<210> SEQ ID NO 91
<211> LENGTH: 21
<212> TYPE: RNA
<213> ORGANISM: homo sapiens
<223> OTHER INFORMATION: hsa-miR-1237-3p MIMAT0005592

<400> SEQUENCE: 91
uccuucugcu ccgucccca g                                                21

<210> SEQ ID NO 92
<211> LENGTH: 21
<212> TYPE: RNA
<213> ORGANISM: homo sapiens
<223> OTHER INFORMATION: hsa-miR-129-5p MIMAT0000242

<400> SEQUENCE: 92
cuuuuugcgg ucugggcuug c                                               21

<210> SEQ ID NO 93
<211> LENGTH: 22
<212> TYPE: RNA
<213> ORGANISM: homo sapiens
<223> OTHER INFORMATION: hsa-miR-148b-3p MIMAT0000759

<400> SEQUENCE: 93
ucagugcauc acagaacuuu gu                                              22

<210> SEQ ID NO 94
```

```
<211> LENGTH: 22
<212> TYPE: RNA
<213> ORGANISM: homo sapiens
<223> OTHER INFORMATION: hsa-miR-377-3p MIMAT0000730

<400> SEQUENCE: 94
aucacacaaa ggcaacuuuu gu                                              22

<210> SEQ ID NO 95
<211> LENGTH: 22
<212> TYPE: RNA
<213> ORGANISM: homo sapiens
<223> OTHER INFORMATION: hsa-let-7b-3p MIMAT0004482

<400> SEQUENCE: 95
cuauacaacc uacugccuuc cc                                              22

<210> SEQ ID NO 96
<211> LENGTH: 24
<212> TYPE: RNA
<213> ORGANISM: homo sapiens
<223> OTHER INFORMATION: hsa-miR-125a-5p MIMAT0000443

<400> SEQUENCE: 96
ucccugagac ccuuuaaccu guga                                            24

<210> SEQ ID NO 97
<211> LENGTH: 22
<212> TYPE: RNA
<213> ORGANISM: homo sapiens
<223> OTHER INFORMATION: hsa-miR-125a-3p MIMAT0004602

<400> SEQUENCE: 97
acaggugagg uucuugggag cc                                              22

<210> SEQ ID NO 98
<211> LENGTH: 22
<212> TYPE: RNA
<213> ORGANISM: homo sapiens
<223> OTHER INFORMATION: hsa-miR-148b-5p MIMAT0004699

<400> SEQUENCE: 98
aaguucuguu auacacucag gc                                              22

<210> SEQ ID NO 99
<211> LENGTH: 22
<212> TYPE: RNA
<213> ORGANISM: homo sapiens
<223> OTHER INFORMATION: hsa-miR-22-3p MIMAT0000077

<400> SEQUENCE: 99
aagcugccag uugaagaacu gu                                              22

<210> SEQ ID NO 100
<211> LENGTH: 21
<212> TYPE: RNA
<213> ORGANISM: homo sapiens
<223> OTHER INFORMATION: hsa-miR-1237-5p MIMAT0022946

<400> SEQUENCE: 100 cggggggcggg gccgaagcgc g                                              21

<210> SEQ ID NO 101
<211> LENGTH: 22
<212> TYPE: RNA
```

```
<213> ORGANISM: homo sapiens
<223> OTHER INFORMATION: hsa-let-7f-1-3p MIMAT0004486

<400> SEQUENCE: 101
cuauacaauc uauugccuuc cc                                          22

<210> SEQ ID NO 102
<211> LENGTH: 22
<212> TYPE: RNA
<213> ORGANISM: homo sapiens
<223> OTHER INFORMATION: hsa-miR-29a-5p MIMAT0004503

<400> SEQUENCE: 102
acugauuucu uuugguguuc ag                                          22

<210> SEQ ID NO 103
<211> LENGTH: 22
<212> TYPE: RNA
<213> ORGANISM: homo sapiens
<223> OTHER INFORMATION: hsa-miR-193a-5p MIMAT0004614

<400> SEQUENCE: 103
ugggucuuug cgggcgagau ga                                          22

<210> SEQ ID NO 104
<211> LENGTH: 23
<212> TYPE: RNA
<213> ORGANISM: homo sapiens
<223> OTHER INFORMATION: hsa-miR-423-3p MIMAT0001340

<400> SEQUENCE: 104
agcucggucu gaggccccuc agu                                         23

<210> SEQ ID NO 105
<211> LENGTH: 22
<212> TYPE: RNA
<213> ORGANISM: homo sapiens
<223> OTHER INFORMATION: hsa-miR-191-3p MIMAT0001618

<400> SEQUENCE: 105
gcugcgcuug gauuucgucc cc                                          22

<210> SEQ ID NO 106
<211> LENGTH: 23
<212> TYPE: RNA
<213> ORGANISM: homo sapiens
<223> OTHER INFORMATION: hsa-miR-301a-3p MIMAT0000688

<400> SEQUENCE: 106
cagugcaaua guauugucaa agc                                         23

<210> SEQ ID NO 107
<211> LENGTH: 23
<212> TYPE: RNA
<213> ORGANISM: homo sapiens
<223> OTHER INFORMATION: hsa-miR-767-3p MIMAT0003883

<400> SEQUENCE: 107
ucugcucaua ccccaugguu ucu                                         23

<210> SEQ ID NO 108
<211> LENGTH: 19
<212> TYPE: RNA
<213> ORGANISM: homo sapiens
<223> OTHER INFORMATION: hsa-miR-563 MIMAT0003227
```

```
<400> SEQUENCE: 108
agguugacau acguucccc                                              19

<210> SEQ ID NO 109
<211> LENGTH: 22
<212> TYPE: RNA
<213> ORGANISM: homo sapiens
<223> OTHER INFORMATION: hsa-miR-95 MIMAT0000094

<400> SEQUENCE: 109
uucaacgggu auuauugag ca                                           22

<210> SEQ ID NO 110
<211> LENGTH: 22
<212> TYPE: RNA
<213> ORGANISM: homo sapiens
<223> OTHER INFORMATION: hsa-miR-1234-3p MIMAT0005589

<400> SEQUENCE: 110
ucggccugac cacccacccc ac                                          22

<210> SEQ ID NO 111
<211> LENGTH: 22
<212> TYPE: RNA
<213> ORGANISM: homo sapiens
<223> OTHER INFORMATION: hsa-miR-1225-3p MIMAT0005573

<400> SEQUENCE: 111
ugagccccug ugccgccccc ag                                          22

<210> SEQ ID NO 112
<211> LENGTH: 23
<212> TYPE: RNA
<213> ORGANISM: homo sapiens
<223> OTHER INFORMATION: hsa-miR-136-5p MIMAT0000448

<400> SEQUENCE: 112
acuccauuug uuuugaugau gga                                         23

<210> SEQ ID NO 113
<211> LENGTH: 21
<212> TYPE: RNA
<213> ORGANISM: homo sapiens
<223> OTHER INFORMATION: hsa-miR-1234-5p MIMAT0022944

<400> SEQUENCE: 113
gggggggggg ggggggggcc g                                           21

<210> SEQ ID NO 114
<211> LENGTH: 22
<212> TYPE: RNA
<213> ORGANISM: homo sapiens
<223> OTHER INFORMATION: hsa-miR-99a-5p MIMAT0000097

<400> SEQUENCE: 114
aacccguaga uccgaucuug ug                                          22

<210> SEQ ID NO 115
<211> LENGTH: 22
<212> TYPE: RNA
<213> ORGANISM: homo sapiens
<223> OTHER INFORMATION: hsa-miR-32-5p MIMAT0000090

<400> SEQUENCE: 115
```

```
uauugcacau uacuaaguug ca                                              22
```

<210> SEQ ID NO 116
<211> LENGTH: 23
<212> TYPE: RNA
<213> ORGANISM: homo sapiens
<223> OTHER INFORMATION: hsa-miR-191-5p MIMAT0000440

<400> SEQUENCE: 116

```
caacggaauc ccaaaagcag cug                                             23
```

<210> SEQ ID NO 117
<211> LENGTH: 20
<212> TYPE: RNA
<213> ORGANISM: homo sapiens
<223> OTHER INFORMATION: hsa-miR-33b-5p MIMAT0003301

<400> SEQUENCE: 117

```
gugcauugcu guugcauugc                                                 20
```

<210> SEQ ID NO 118
<211> LENGTH: 71
<212> TYPE: RNA
<213> ORGANISM: homo sapiens
<223> OTHER INFORMATION: hsa-mir-1-1 MI0000651

<400> SEQUENCE: 118

```
ugggaaacau acuucuuuau augcccauau ggaccugcua agcuauggaa uguaaagaag      60
uauguaucuc a                                                          71
```

<210> SEQ ID NO 119
<211> LENGTH: 85
<212> TYPE: RNA
<213> ORGANISM: homo sapiens
<223> OTHER INFORMATION: hsa-mir-1-2 MI0000437

<400> SEQUENCE: 119

```
accuacucag aguacauacu ucuuuaugua cccauaugaa cauacaaugc uaggaaugu       60 aaagaaguau guauuuuugg uaggc                                           85
```

<210> SEQ ID NO 120
<211> LENGTH: 110
<212> TYPE: RNA
<213> ORGANISM: homo sapiens
<223> OTHER INFORMATION: hsa-mir-7-1 MI0000263

<400> SEQUENCE: 120

```
uuggauguug gccuaguucu guguggaaga cuagugauuu uguuguuuuu agauaacuaa      60
aucgacaaca aaucacaguc ugccauaugg cacaggccau gccucuacag               110
```

<210> SEQ ID NO 121
<211> LENGTH: 110
<212> TYPE: RNA
<213> ORGANISM: homo sapiens
<223> OTHER INFORMATION: hsa-mir-7-2 MI0000264

<400> SEQUENCE: 121

```
cuggauacag aguggaccgg cuggccccau cuggaagacu agugauuuug uuguugucuu      60
acugcgcuca acaacaaauc ccagucuacc uaauggugcc agccaucgca               110
```

<210> SEQ ID NO 122

```
<211> LENGTH: 110
<212> TYPE: RNA
<213> ORGANISM: homo sapiens
<223> OTHER INFORMATION: hsa-mir-7-3 MI0000265

<400> SEQUENCE: 122
agauuagagu ggcugugguc uagugcugug uggaagacua gugauuuugu uguucgaug      60 uacuacgaca acaagucaca gccggccuca uagcgcagac ucccuucgac               110

<210> SEQ ID NO 123
<211> LENGTH: 92
<212> TYPE: RNA
<213> ORGANISM: homo sapiens
<223> OTHER INFORMATION: hsa-mir-30e MI0000749

<400> SEQUENCE: 123
gggcagucuu ugcuacugua aacauccuug acuggaagcu guaagguguu cagaggagcu    60
uucagucgga uguuuacagc ggcaggcugc ca                                   92

<210> SEQ ID NO 124
<211> LENGTH: 69
<212> TYPE: RNA
<213> ORGANISM: homo sapiens
<223> OTHER INFORMATION: hsa-mir-33a MI0000091

<400> SEQUENCE: 124
cuguggugca uuguaguugc auugcauguu cuggugguac ccaugcaaug uuccacagu     60 gcaucacag                                                             69

<210> SEQ ID NO 125
<211> LENGTH: 119
<212> TYPE: RNA
<213> ORGANISM: homo sapiens
<223> OTHER INFORMATION: hsa-mir-133b MI0000822

<400> SEQUENCE: 125
ccucagaaga aagaugcccc cugcucuggc uggucaaacg gaaccaaguc cgucuuccug    60
agagguuugg uccccuucaa ccagcuacag cagggcuggc aaugcccagu ccuuggaga    119

<210> SEQ ID NO 126
<211> LENGTH: 86
<212> TYPE: RNA
<213> ORGANISM: homo sapiens
<223> OTHER INFORMATION: hsa-mir-144 MI0000460

<400> SEQUENCE: 126
uggggcccug gcugggauau caucauauac uguaaguuug cgaugagaca cuacaguaua    60
gaugauguac uaguccgggc acccc                                          86

<210> SEQ ID NO 127
<211> LENGTH: 71
<212> TYPE: RNA
<213> ORGANISM: homo sapiens
<223> OTHER INFORMATION: hsa-mir-199a-1 MI0000242

<400> SEQUENCE: 127
gccaacccag uguucagacu accuguucag gaggcucuca auguguacag uagucugcac    60
auugguuagg c                                                         71

<210> SEQ ID NO 128
<211> LENGTH: 110
```

```
<212> TYPE: RNA
<213> ORGANISM: homo sapiens
<223> OTHER INFORMATION: hsa-mir-199a-2 MI0000281

<400> SEQUENCE: 128
aggaagcuuc uggagauccu gcuccgucgc cccaguguuc agacuaccug uucaggacaa    60
ugccguugua caguagucug cacauugguu agacugggca agggagagca              110

<210> SEQ ID NO 129
<211> LENGTH: 110
<212> TYPE: RNA
<213> ORGANISM: homo sapiens
<223> OTHER INFORMATION: hsa-mir-199b MI0000282

<400> SEQUENCE: 129
ccagaggaca ccuccacucc gucuacccag uguuuagacu aucguucag gacucccaaa     60 uuguacagua gucugcacau ugguuaggcu gggcugggu agaccucgg                110

<210> SEQ ID NO 130
<211> LENGTH: 110
<212> TYPE: RNA
<213> ORGANISM: homo sapiens
<223> OTHER INFORMATION: hsa-mir-210 MI0000286

<400> SEQUENCE: 130
acccggcagu gccuccaggc gcagggcagc cccugcccac cgcacacugc gcugcccag     60 acccacugug cgugugacag cggcugaucu gugccugggc agcgcgaccc              110

<210> SEQ ID NO 131
<211> LENGTH: 110
<212> TYPE: RNA
<213> ORGANISM: homo sapiens
<223> OTHER INFORMATION: hsa-mir-221 MI0000298

<400> SEQUENCE: 131
ugaacaucca ggucuggggc augaaccugg cauacaaugu agauuucugu guucguuagg    60
caacagcuac auugucugcu ggguuucagg cuaccuggaa acauguucuc               110

<210> SEQ ID NO 132
<211> LENGTH: 95
<212> TYPE: RNA
<213> ORGANISM: homo sapiens
<223> OTHER INFORMATION: hsa-mir-340 MI0000802

<400> SEQUENCE: 132
uuguaccugg ugugauuaua aagcaaugag acgauuguc auaugucguu uguggauccc     60
gucucaguua cuuuauagcc auaccuggua ucuua                              95

<210> SEQ ID NO 133
<211> LENGTH: 98
<212> TYPE: RNA
<213> ORGANISM: homo sapiens
<223> OTHER INFORMATION: hsa-mir-424 MI0001446

<400> SEQUENCE: 133
cgaggggaua cagcagcaau ucauguuuug aaguguucua aaugguucaa aacgugaggc    60
gcugcuauac ccccucgugg ggaagguaga aggugggg                           98

<210> SEQ ID NO 134
<211> LENGTH: 94
<212> TYPE: RNA
```

```
<213> ORGANISM: homo sapiens
<223> OTHER INFORMATION: hsa-mir-575 MI0003582

<400> SEQUENCE: 134
aauucagccc ugccacuggc uuaugucaug accuugggcu acucaggcug ucugcacaau    60
gagccaguug dacaggagca gugccacuca acuc                                94

<210> SEQ ID NO 135
<211> LENGTH: 98
<212> TYPE: RNA
<213> ORGANISM: homo sapiens
<223> OTHER INFORMATION: hsa-mir-582 MI0003589

<400> SEQUENCE: 135
aucugugcuc uuugauuaca guuguucaac caguuacuaa ucuaacuaau uguaacuggu    60
ugaacaacug aacccaaagg gugcaaagua gaaacauu                            98

<210> SEQ ID NO 136
<211> LENGTH: 118
<212> TYPE: RNA
<213> ORGANISM: homo sapiens
<223> OTHER INFORMATION: hsa-mir-671 MI0003760

<400> SEQUENCE: 136
gcaggugaac uggcaggcca ggaagaggag gaagcccugg aggggcugga ggugauggau    60 guuuccucc gguucucagg gcuccaccuc uuucgggccg uagagccagg gcuggugc     118

<210> SEQ ID NO 137
<211> LENGTH: 69
<212> TYPE: RNA
<213> ORGANISM: homo sapiens
<223> OTHER INFORMATION: hsa-mir-1229 MI0006319

<400> SEQUENCE: 137
guggguaggg uuuggggggag agcgugggcu gggguucagg gacacccucu caccacugcc    60
cucccacag                                                            69

<210> SEQ ID NO 138
<211> LENGTH: 78
<212> TYPE: RNA
<213> ORGANISM: homo sapiens
<223> OTHER INFORMATION: hsa-mir-1267 MI0006404

<400> SEQUENCE: 138
cucccaaauc uccuguugaa guguaauccc caccuccagc auuggggauu acauuucaac    60
augagauuug gaugagga                                                  78

<210> SEQ ID NO 139
<211> LENGTH: 74
<212> TYPE: RNA
<213> ORGANISM: homo sapiens
<223> OTHER INFORMATION: hsa-let-7a-3 MI0000062

<400> SEQUENCE: 139
gggugaggua guagguugua uaguuugggg cucugcccug cuaugggaua acuauacaau    60
cuacugucuu uccu                                                      74

<210> SEQ ID NO 140
<211> LENGTH: 79
<212> TYPE: RNA
<213> ORGANISM: homo sapiens
```

<223> OTHER INFORMATION: hsa-let-7e MI0000066

<400> SEQUENCE: 140
cccgggcuga gguaggaggu uguauaguug aggaggacac ccaaggagau cacuauacgg    60
ccuccuagcu uuccccagg    79

<210> SEQ ID NO 141
<211> LENGTH: 85
<212> TYPE: RNA
<213> ORGANISM: homo sapiens
<223> OTHER INFORMATION: hsa-mir-22 MI0000078

<400> SEQUENCE: 141
ggcugagccg caguaguucu ucaguggcaa gcuuuauguc cugacccagc uaaagcugcc    60
aguugaagaa cuguugcccu cugcc    85

<210> SEQ ID NO 142
<211> LENGTH: 64
<212> TYPE: RNA
<213> ORGANISM: homo sapiens
<223> OTHER INFORMATION: hsa-mir-29a MI0000087

<400> SEQUENCE: 142
augacugauu ucuuuuggug uucagaguca auauaauuuu cuagcaccau cugaaaucgg    60
uuau    64

<210> SEQ ID NO 143
<211> LENGTH: 81
<212> TYPE: RNA
<213> ORGANISM: homo sapiens
<223> OTHER INFORMATION: hsa-mir-29b-1 MI0000105

<400> SEQUENCE: 143
cuucaggaag cugguuucau auggugguuu agauuuaaau agugauuguc uagcaccauu    60
ugaaaucagu guucuugggg g    81

<210> SEQ ID NO 144
<211> LENGTH: 70
<212> TYPE: RNA
<213> ORGANISM: homo sapiens
<223> OTHER INFORMATION: hsa-mir-32 MI0000090

<400> SEQUENCE: 144
ggagauauug cacauuacua aguugcaugu ugucacggcc ucaaugcaau uuagugugug    60
ugauauuuuc    70

<210> SEQ ID NO 145
<211> LENGTH: 96
<212> TYPE: RNA
<213> ORGANISM: homo sapiens
<223> OTHER INFORMATION: hsa-mir-33b MI0003646

<400> SEQUENCE: 145
gcgggcggcc ccgcggugca uugcuguugc auugcacgug ugugaggcgg gugcagugcc    60
ucggcagugc agcccggagc cggccccugg caccac    96

<210> SEQ ID NO 146
<211> LENGTH: 110
<212> TYPE: RNA
<213> ORGANISM: homo sapiens
<223> OTHER INFORMATION: hsa-mir-34a MI0000268

<400> SEQUENCE: 146
ggccagcugu gaguguuucu uuggcagugu cuuagcuggu uguugugagc aauaguaagg     60
aagcaaucag caaguauacu gcccuagaag ugcugcacgu uguggggccc               110

<210> SEQ ID NO 147
<211> LENGTH: 96
<212> TYPE: RNA
<213> ORGANISM: homo sapiens
<223> OTHER INFORMATION: hsa-mir-92b MI0003560

<400> SEQUENCE: 147
cgggccccgg gcgggcggga gggacgggac gcggugcagu uuguuuuuu cccccgccaa     60 uauugcacuc gucccggccu ccggccccc cggccc                              96

<210> SEQ ID NO 148
<211> LENGTH: 81
<212> TYPE: RNA
<213> ORGANISM: homo sapiens
<223> OTHER INFORMATION: hsa-mir-95 MI0000097

<400> SEQUENCE: 148
aacacagugg gcacucaaua aaugucuguu gaauugaaau gcguuacauu caacggguau     60
uuauugagca cccacucugu g                                             81

<210> SEQ ID NO 149
<211> LENGTH: 81
<212> TYPE: RNA
<213> ORGANISM: homo sapiens
<223> OTHER INFORMATION: hsa-mir-99a MI0000101

<400> SEQUENCE: 149
cccauuggca uaaacccgua gauccgaucu uguggugaag uggaccgcac aagcucgcuu     60
cuaugggucu gugucagugu g                                             81

<210> SEQ ID NO 150
<211> LENGTH: 86
<212> TYPE: RNA
<213> ORGANISM: homo sapiens
<223> OTHER INFORMATION: hsa-mir-125a MI0000469

<400> SEQUENCE: 150
ugccagucuc uagguccug agaccuuuua accugugagg acauccaggg ucacagguga     60
gguucuuggg agccuggcgu cuggcc                                        86

<210> SEQ ID NO 151
<211> LENGTH: 88
<212> TYPE: RNA
<213> ORGANISM: homo sapiens
<223> OTHER INFORMATION: hsa-mir-125b-1 MI0000446

<400> SEQUENCE: 151
ugcgcuccuc ucaguccug agacccuaac uugugauguu uaccguuuaa auccacgggu     60
uaggcucuug ggagcugcga gucgugcu                                      88

<210> SEQ ID NO 152
<211> LENGTH: 89
<212> TYPE: RNA
<213> ORGANISM: homo sapiens
<223> OTHER INFORMATION: hsa-mir-125b-2 MI0000470

<400> SEQUENCE: 152
accagacuuu uccuagucccc ugagacccua acuugugagg uauuuuagua acaucacaag    60
ucaggcucuu gggaccuagg cggagggga    89

<210> SEQ ID NO 153
<211> LENGTH: 72
<212> TYPE: RNA
<213> ORGANISM: homo sapiens
<223> OTHER INFORMATION: hsa-mir-129-1 MI0000252

<400> SEQUENCE: 153
ggaucuuuuu gcggucuggg cuugcuguuc cucucaacag uagucaggaa gcccuuaccc    60
caaaaaguau cu    72

<210> SEQ ID NO 154
<211> LENGTH: 90
<212> TYPE: RNA
<213> ORGANISM: homo sapiens
<223> OTHER INFORMATION: hsa-mir-129-2 MI0000473

<400> SEQUENCE: 154
ugcccuucgc gaaucuuuuu gcggucuggg cuugcuguac auaacucaau agccggaagc    60
ccuuacccca aaaagcauuu gcggagggcg    90

<210> SEQ ID NO 155
<211> LENGTH: 82
<212> TYPE: RNA
<213> ORGANISM: homo sapiens
<223> OTHER INFORMATION: hsa-mir-136 MI0000475

<400> SEQUENCE: 155
ugagcccucg gaggacucca uuuguuuuga ugauggauuc uuaugcucca ucaucgucuc    60
aaaugagucu ucagaggguu cu    82

<210> SEQ ID NO 156
<211> LENGTH: 99
<212> TYPE: RNA
<213> ORGANISM: homo sapiens
<223> OTHER INFORMATION: hsa-mir-148b MI0000811

<400> SEQUENCE: 156
caagcacgau uagcauuuga ggugaaguuc uguuauacac ucaggcugug gcucucugaa    60
agucagugca ucacagaacu uugucucgaa agcuuucua    99

<210> SEQ ID NO 157
<211> LENGTH: 87
<212> TYPE: RNA
<213> ORGANISM: homo sapiens
<223> OTHER INFORMATION: hsa-mir-152 MI0000462

<400> SEQUENCE: 157 ugucccccccc ggcccagguu cugugauaca cuccgacucg ggcucuggag cagucagugc    60
augacagaac uuggccccgg aaggacc    87

<210> SEQ ID NO 158
<211> LENGTH: 110
<212> TYPE: RNA
<213> ORGANISM: homo sapiens
<223> OTHER INFORMATION: hsa-mir-181c MI0000271

<400> SEQUENCE: 158

```
cggaaaauuu gccaagggu uggggaaca uucaaccugu cggugaguuu gggcagcuca    60
ggcaaaccau cgaccguuga guggacccug aggccuggaa uugccauccu            110
```

<210> SEQ ID NO 159
<211> LENGTH: 92
<212> TYPE: RNA
<213> ORGANISM: homo sapiens
<223> OTHER INFORMATION: hsa-mir-191 MI0000465

<400> SEQUENCE: 159

```
cggcuggaca gcgggcaacg gaaucccaaa agcagcuguu gucuccagag cauuccagcu    60
gcgcuuggau uucgucccu gcucuccugc cu                                   92
```

<210> SEQ ID NO 160
<211> LENGTH: 88
<212> TYPE: RNA
<213> ORGANISM: homo sapiens
<223> OTHER INFORMATION: hsa-mir-193a MI0000487

<400> SEQUENCE: 160

```
cgaggauggg agcugagggc uggucuuug cgggcgagau gagggugucg gaucaacugg    60
ccuacaaagu cccaguucuc ggcccccg                                      88
```

<210> SEQ ID NO 161
<211> LENGTH: 110
<212> TYPE: RNA
<213> ORGANISM: homo sapiens
<223> OTHER INFORMATION: hsa-mir-223 MI0000300

<400> SEQUENCE: 161

```
ccuggccucc ugcagugcca cgcuccgugu auuugacaag cugaguugga cacuccaugu    60
gguagagugu caguuuguca aauaccccaa gugcggcaca ugcuuaccag              110
```

<210> SEQ ID NO 162
<211> LENGTH: 86
<212> TYPE: RNA
<213> ORGANISM: homo sapiens
<223> OTHER INFORMATION: hsa-mir-301a MI0000745

<400> SEQUENCE: 162

```
acugcuaacg aaugcucuga cuuuauugca cuacuguacu uuacagcuag cagugcaaua    60
guauugucaa agcaucugaa agcagg                                        86
```

<210> SEQ ID NO 163
<211> LENGTH: 94
<212> TYPE: RNA
<213> ORGANISM: homo sapiens
<223> OTHER INFORMATION: hsa-mir-335 MI0000816

<400> SEQUENCE: 163

```
uguuuugagc gggggucaag agcaauaacg aaaaauguuu gcauaaaacc guuuucauu    60 auugcuccug accuccucuc auuugcuaua uuca                              94
```

<210> SEQ ID NO 164
<211> LENGTH: 67
<212> TYPE: RNA
<213> ORGANISM: homo sapiens
<223> OTHER INFORMATION: hsa-mir-338 MI0000814

<400> SEQUENCE: 164

```
ucuccaacaa uauccuggug cugagugaug acucaggcga cuccagcauc agugauuuug    60
uugaaga                                                              67
```

<210> SEQ ID NO 165
<211> LENGTH: 65
<212> TYPE: RNA
<213> ORGANISM: homo sapiens
<223> OTHER INFORMATION: hsa-mir-362 MI0000762

<400> SEQUENCE: 165

```
cuugaauccu uggaaccuag gugugagugc uauuucagug caacacaccu auucaaggau    60
ucaaa                                                                65
```

<210> SEQ ID NO 166
<211> LENGTH: 67
<212> TYPE: RNA
<213> ORGANISM: homo sapiens
<223> OTHER INFORMATION: hsa-mir-371a MI0000779

<400> SEQUENCE: 166

```
guggcacuca aacugugggg gcacuuucug cucucuggug aaagugccgc caucuuuga     60 guguuac                                                              67
```

<210> SEQ ID NO 167
<211> LENGTH: 69
<212> TYPE: RNA
<213> ORGANISM: homo sapiens
<223> OTHER INFORMATION: hsa-mir-373 MI0000781

<400> SEQUENCE: 167

```
gggauacuca aaauggggc gcuuuccuuu uugucuguac ugggaagugc uucgauuuug     60
ggguguccc                                                            69
```

<210> SEQ ID NO 168
<211> LENGTH: 68
<212> TYPE: RNA
<213> ORGANISM: homo sapiens
<223> OTHER INFORMATION: hsa-mir-376a-1 MI0000784

<400> SEQUENCE: 168

```
uaaaagguag auucuccuuc uaugaguaca uuauuuauga uuaaucauag aggaaaaucc    60
acguuuuc                                                             68
```

<210> SEQ ID NO 169
<211> LENGTH: 80
<212> TYPE: RNA
<213> ORGANISM: homo sapiens
<223> OTHER INFORMATION: hsa-mir-376a-2 MI0003529

<400> SEQUENCE: 169

```
gguauuuaaa agguagauuu uccuucuaug guuacguguu ugaugguuaa ucauagagga    60
aaauccacgu uuucaguauc                                                80
```

<210> SEQ ID NO 170
<211> LENGTH: 69
<212> TYPE: RNA
<213> ORGANISM: homo sapiens
<223> OTHER INFORMATION: hsa-mir-377 MI0000785

<400> SEQUENCE: 170

```
uugagcagag guugcccuug gugaauucgc uuuauuuaug uugaaucaca caaaggcaac    60
```

```
uuuuguuug                                                         69

<210> SEQ ID NO 171
<211> LENGTH: 94
<212> TYPE: RNA
<213> ORGANISM: homo sapiens
<223> OTHER INFORMATION: hsa-mir-423 MI0001445

<400> SEQUENCE: 171
auaaaggaag uuaggcugag gggcagagag cgagacuuuu cuauuuucca aaagcucggu    60
cugaggcccc ucagucuugc uuccuaaccc gcgc                               94

<210> SEQ ID NO 172
<211> LENGTH: 87
<212> TYPE: RNA
<213> ORGANISM: homo sapiens
<223> OTHER INFORMATION: hsa-mir-425 MI0001448

<400> SEQUENCE: 172
gaaagcgcuu uggaaugaca cgaucacucc cguugagugg gcacccgaga agccaucggg    60
aaugucgugu ccgcccagug cucuuuc                                       87

<210> SEQ ID NO 173
<211> LENGTH: 84
<212> TYPE: RNA
<213> ORGANISM: homo sapiens
<223> OTHER INFORMATION: hsa-mir-505 MI0003190

<400> SEQUENCE: 173
gaugcaccca guggggagc caggaaguau ugauguuucu gccaguuuag cgucaacacu     60
ugcugguuuc cucucuggag cauc                                          84

<210> SEQ ID NO 174
<211> LENGTH: 78
<212> TYPE: RNA
<213> ORGANISM: homo sapiens
<223> OTHER INFORMATION: hsa-mir-543 MI0005565

<400> SEQUENCE: 174
uacuuaauga gaaguugccc guguuuuuuu cgcuuuauuu gugacgaaac auucgcggug    60
cacuucuuuu ucaguauc                                                 78

<210> SEQ ID NO 175
<211> LENGTH: 86
<212> TYPE: RNA
<213> ORGANISM: homo sapiens
<223> OTHER INFORMATION: hsa-mir-548m MI0006400

<400> SEQUENCE: 175
auauuagguu ggugcaaagg uauuuguggu uuuugucauu aaaguaaugc aaaagccaca    60
aauaccuuug caccaaccua auauua                                        86

<210> SEQ ID NO 176
<211> LENGTH: 98
<212> TYPE: RNA
<213> ORGANISM: homo sapiens
<223> OTHER INFORMATION: hsa-mir-557 MI0003563

<400> SEQUENCE: 176
agaaugggca aaugaacagu aaauuuggag gccugggggcc cucccugcug cuggagaagu   60
```

```
guuugcacgg gugggccuug ucuuugaaag gaggugga                                 98
```

<210> SEQ ID NO 177
<211> LENGTH: 79
<212> TYPE: RNA
<213> ORGANISM: homo sapiens
<223> OTHER INFORMATION: hsa-mir-563 MI0003569

<400> SEQUENCE: 177

```
agcaaagaag uguguugccc ucuaggaaau guguguugcu cugauguaau uagguugaca        60
uacguuuccc ugguagcca                                                     79
```

<210> SEQ ID NO 178
<211> LENGTH: 97
<212> TYPE: RNA
<213> ORGANISM: homo sapiens
<223> OTHER INFORMATION: hsa-mir-584 MI0003591

<400> SEQUENCE: 178

```
uagggugacc agccauuaug guuugccugg gacugaggaa uuugcuggga uaugucaguu        60
ccaggccaac caggcugguu ggucucccug aagcaac                                 97
```

<210> SEQ ID NO 179
<211> LENGTH: 98
<212> TYPE: RNA
<213> ORGANISM: homo sapiens
<223> OTHER INFORMATION: hsa-mir-602 MI0003615

<400> SEQUENCE: 179

```
uucucacccc cgccugacac gggcgacagc ugcggcccgc uguguucacu cgggccgagu        60
gcgucuccug ucaggcaagg gagagcagag ccccccug                                98
```

<210> SEQ ID NO 180
<211> LENGTH: 97
<212> TYPE: RNA
<213> ORGANISM: homo sapiens
<223> OTHER INFORMATION: hsa-mir-634 MI0003649

<400> SEQUENCE: 180

```
aaacccacac cacugcauuu uggccaucga ggguuggggc uuggugucau gccccaagau        60
aaccagcacc ccaacuuugg acagcaugga uuagucu                                 97
```

<210> SEQ ID NO 181
<211> LENGTH: 109
<212> TYPE: RNA
<213> ORGANISM: homo sapiens
<223> OTHER INFORMATION: hsa-mir-767 MI0003763

<400> SEQUENCE: 181

```
gcuuuuauau uguagguuuu ugcucaugca ccaugguugu cugagcaugc agcaugcuug        60
ucugcucaua ccccaugguu ucugagcagg aaccuucauu gucuacugc                   109
```

<210> SEQ ID NO 182
<211> LENGTH: 81
<212> TYPE: RNA
<213> ORGANISM: homo sapiens
<223> OTHER INFORMATION: hsa-mir-876 MI0005542

<400> SEQUENCE: 182

```
ugaagugcug uggauuucuu ugugaaucac cauaucuaag cuaauguggu ggugguuuac        60
aaaguaauuc auagugcuuc a                                                  81
```

<210> SEQ ID NO 183
<211> LENGTH: 77
<212> TYPE: RNA
<213> ORGANISM: homo sapiens
<223> OTHER INFORMATION: hsa-mir-933 MI0005755

<400> SEQUENCE: 183
acuuggguca guucagaggu ccucggggcg cgcgucgagu cagccgugug cgcagggaga    60
ccucucccac ccacagu                                                  77

<210> SEQ ID NO 184
<211> LENGTH: 90
<212> TYPE: RNA
<213> ORGANISM: homo sapiens
<223> OTHER INFORMATION: hsa-mir-1225 MI0006311

<400> SEQUENCE: 184
guggguacgg cccagugggg gggagaggga cacgcccugg cucugccca gggugcagcc    60 ggacugacug agcccugugu ccgccccag                                     90

<210> SEQ ID NO 185
<211> LENGTH: 84
<212> TYPE: RNA
<213> ORGANISM: homo sapiens
<223> OTHER INFORMATION: hsa-mir-1234 MI0006324

<400> SEQUENCE: 185
gugagugugg gguggcuggg ggggggggg gggggccggg gacggcuugg gccugccuag    60
ucggccugac cacccacccc acag                                          84

<210> SEQ ID NO 186
<211> LENGTH: 102
<212> TYPE: RNA
<213> ORGANISM: homo sapiens
<223> OTHER INFORMATION: hsa-mir-1237 MI0006327

<400> SEQUENCE: 186
gugggagggc ccaggcgcgg gcaggggugg ggguggcaga gcgcugucccc ggggcgggg    60 ccgaagcgcg gcgaccguaa cuccuucugc uccguccccc ag                      102

<210> SEQ ID NO 187
<211> LENGTH: 83
<212> TYPE: RNA
<213> ORGANISM: homo sapiens
<223> OTHER INFORMATION: hsa-mir-1238 MI0006328

<400> SEQUENCE: 187
gugaguggga gcccagugu gugguugggg ccauggcggg ugggcagccc agccucugag    60
ccuuccucgu cugucugccc cag                                           83

<210> SEQ ID NO 188
<211> LENGTH: 85
<212> TYPE: RNA
<213> ORGANISM: homo sapiens
<223> OTHER INFORMATION: hsa-mir-1244-1 MI0006379

<400> SEQUENCE: 188
aucuuauucc gagcauucca guaacuuuuu uguguaugua cuuagcugua cuauaaguag    60
uuggguugua ugagauggu aaaaa                                          85

```
<210> SEQ ID NO 189
<211> LENGTH: 85
<212> TYPE: RNA
<213> ORGANISM: homo sapiens
<223> OTHER INFORMATION: hsa-mir-1244-2 MI0015974

<400> SEQUENCE: 189
aucuuauucc gagcauucca guaacuuuuu uguguaugua cuuagcugua cuauaaguag        60
uugguuugua ugagaugguu aaaaa                                             85

<210> SEQ ID NO 190
<211> LENGTH: 85
<212> TYPE: RNA
<213> ORGANISM: homo sapiens
<223> OTHER INFORMATION: hsa-mir-1244-3 MI0015975

<400> SEQUENCE: 190
aucuuauucc gagcauucca guaacuuuuu uguguaugua cuuagcugua cuauaaguag        60
uugguuugua ugagaugguu aaaaa                                             85

<210> SEQ ID NO 191
<211> LENGTH: 53
<212> TYPE: RNA
<213> ORGANISM: homo sapiens
<223> OTHER INFORMATION: hsa-mir-1825 MI0008193

<400> SEQUENCE: 191
agagacuggg gugcugggcu ccccuagacu aggacuccag ugcccuccuc ucc              53
```

METHODS AND COMPOSITIONS FOR ASSESSING PATIENTS WITH PREECLAMPSIA-RELATED CONDITIONS USING MICRORNA

RELATED APPLICATIONS

This application claims priority to U.S. Provisional Patent Application Ser. No. 61/767,669, filed Feb. 21, 2013, and is a continuation-in-part of International (PCT) Patent Application Ser. No. PCT/US12/61994, filed Oct. 25, 2012, which is itself a continuation-in-part of U.S. patent application Ser. No. 13/284,739, filed Oct. 28, 2011, which claims priority of U.S. Provisional Patent Application Ser. No. 61/456,063, filed Nov. 1, 2010, all of which are incorporated by reference in their entirety.

FIELD OF THE PRESENT INVENTION

This disclosure generally relates to diagnosis and treatment of reproductive disorders and more specifically to methods and compositions for characterizing individuals or groups of individuals using patterns of expression of one or more microRNA sequences.

BACKGROUND OF THE INVENTION

Preeclampsia and related conditions consume a major part of the management of women who are pregnant or who plan to become pregnant. Loss of pregnancy, both early and late contribute to the total burden of preeclampsia-related disorders on couples desiring children. The economic impact of the disorder when manifested in the later part of pregnancy is particularly severe. At present, management of preeclampsia largely involves control of maternal symptoms and early delivery. Early diagnosis with appropriate treatment offers some hope of prevention.

Clinical symptoms of preeclampsia are largely experienced in the third trimester. It may be subdivided into an early and more severe form manifesting prior to 34 weeks gestation and a more mild form manifesting later. Defined as the appearance of hypertension and proteinuria after 20 weeks gestation, the condition is recognized as a manifestation of endothelial dysfunction in various maternal organs. The most common of these is endothelial dysfunction within the arterioles of the renal glomerulus. Election microscopy demonstrates endothelial swelling and a loss of fenestrations that are requisite to optimal glomerular filtration. The condition, known as endotheliosis, has been regarded as pathognomonic of preeclampsia. The features have more recently been identified in some pregnant women who do not meet the criteria for a clinical diagnosis preeclampsia suggesting that the disorder may affect a larger fraction of pregnant women than is currently recognized.

The pathogenesis of late pregnancy maternal endothelial dysfunction has been the focus of intense study. A growing consensus amongst investigators supports the centrality of endothelial dysfunction as the primary event preceding the development of atherosclerosis. The endothelium is known to be formed and maintained through stimulation by various proangiogenic factors that include vascular endothelial growth factor (VEGF). The glomerular endothelium is maintained by VEGF released by podocytes, specialized epithelial cells juxtaposed to the endothelium separated by a permeable basement membrane. Alterations in placental antiangiogenic factors such as soluble Fms-related tyrosine kinase 1 (sFlt-1) and s-Eng (soluble endoglen, coreceptors of TGF-β1) are known to produce systemic endothelial dysfunction and other manifestations of preeclampsia.

While the clinical disease is generally manifested during the last trimester by the mother, the pathogenesis of the disease evolves during the first trimester. The pathogenesis involves inadequate invasion by extravillous trophoblast into maternal decidual tissues and inadequate transformation of maternal spiral arteries into high capacitance, low resistance vessels that are non-responsive to vasoactive agents. The cause of inadequate invasion has been the focus of research into the etiology of the disease.

Pregnancy in mammals utilizing the hemochorial form of placentation creates an intimate relationship between genetically different beings, one mature (the mother) and one immature (the fetus and placenta). Extravillous trophoblasts break away from the anchoring placental villi and invade the maternal decidual tissues on their journey to the vessels. They must express appropriate adhesion receptors as well as proteolytic enzymes in a directional manner and be responsive to cues within maternal tissues permitting them to attain the appropriate level of invasion.

Research has identified excess release of a soluble form of receptors for angiogenic factors that include sFlt-1 and sEng from the syncytiotrophoblast as useful in diagnosis and assessment of severity of preeclampsia. Increased sFlt-1 identified in maternal peripheral blood, they suggest, corresponds to the degree of third trimester placental ischemia wherein the increased sFlt-1 results in VEGF sequestration and consequent endothelial dysfunction. Oxygen levels within first trimester directly affect trophoblast invasion. Hypoxia inducible factor 1α (HIF-1α), a transcription factor expressed in cytotrophoblast experiencing low oxygen conditions, targets Flt-1, VEGFR-2, Tie-1 and Tie-2. Another HIF-1α target, TGF-β3, has been shown to block cytotrophoblast invasion. Hypoxia has been shown to upregulate sFlt-1 secretion in primary trophoblast cultures. Based in part on such observations, it has be suggested that adequate cytotrophoblast invasion is critical to successful pregnancy. Hypoxic conditions are associated with enhanced trophoblast proliferation while normoxic conditions are associated with enhanced trophoblast invasion. Shortening of the period of physiologic hypoxia, therefore, would be expected to alter the balance between proliferation and migration resulting in profound effects on the process of spiral artery modification. It has further been suggested that alterations in angiogenic pathways in early pregnancy may contribute to inadequate trophoblast invasion of the decidua and transformation of spiral arteries. A continuous cycle involving a deranged balance of angiogenic factors has been postulated to lead to excess production and release of sFlt-1 into the maternal circulation.

Local oxygen tension is pivotal in spiral artery transformation. From three weeks EVT first invade spiral arteries resulting in luminal plugging by endovascular resident trophoblast. During a period lasting from week four to week eleven of pregnancy, only maternal plasma flows through the placental intervillous space. A state of relative hypoxia is thus maintained. Hydroxylation of HIF1α under normoxic conditions permits recognition by the von Hippel-Lindau gene product. In cells exposed to normoxic conditions, HIF-1α is rapidly depleted following ubiquitylation mediated by the von Hippel-Lindau gene product directing its proteasomal degradation. Under hypoxic conditions, HIF-1α is stabilized heterodimerizing with its constitutively expressed partner HIF-1β migrating to the nucleus where they act as a transcriptional regulator of numerous genes responsive to hypoxic conditions. Because hypoxic conditions are associated with enhanced trophoblast proliferation while normoxic conditions are associated with enhanced trophoblast invasion, shortening of the period of physiologic hypoxia, therefore, would be expected to alter the balance between proliferation and migration. This would result in profound effects on the process of spiral artery modification.

Attempts to identify markers of trophoblast derangement during the period of placenta formation have been made. A variety of proteins and nucleic acid markers released from placental tissues have been found useful in diagnosis prior to the development of symptoms as early as the end of the first trimester. However, detection of placenta-derived markers during the first trimester is problematic. Several mechanisms may singly or in aggregate account for poor detection. First, microRNA in plasma or serum is present at low levels requiring their extraction from relatively large quantities of plasma or serum. Second, placental blood flow is blocked during large portions of the first trimester imposing limited distribution of placental microRNAs into plasma. Third, the placenta is quite small during the first trimester limiting the total amount of microRNA produced.

Research has identified a limited repertoire of differentially expressed microRNAs in endometrial stromal and glandular epithelial cells isolated from non-pregnant, secretory phase endometrium suggesting the importance of the endometrial microenvironment on regulation of miRNA expression. Maternal cells are present at the placental site comprising locally-fixed cells comprised of epitheliostromal cells and leukocytes of maternal origin that do not traffic outside of the placental site. The fetus-derived cells and tissues at the placental site constitute a first foreign, non-self, compartment. The decidual component at the placental site comprises a second compartment that is chimeric comprised of both fetal and maternal tissues forming a unique tissue that experiences many of the conditions common to the first compartment. These conditions may include autocrine and paracrine influences and, moreover, involve a signaling dialogue between the first and second compartments. Thus it might be expected that maternal cells within the second compartment might provide significant information upon quantification of microRNAs. However, no suitable and safe methods for collection of material from first trimester decidua are presently available.

Therefore, there is a need for characterizing preeclampsia-related conditions at early stages, such as in the first trimester or even prior to pregnancy. Further, there is a need for obtaining diagnostic information using biological samples that may be collected readily. This invention satisfies these and other needs.

SUMMARY OF THE INVENTION

In accordance with the above needs and those that will be mentioned and will become apparent below, this disclosure is directed to a method for characterizing a preeclampsia-related condition in a subject comprising collecting a first non-placental biological sample, extracting microRNA-comprising RNA from the first non-placental biological sample, quantifying at least one microRNA within the extracted RNA, and comparing the quantification of the at least one microRNA to a quantification of the at least one microRNA from a second, non-placental biological sample. In one aspect, at least one of the first non-placental biological sample and the second non-placental biological sample may be taken during a first trimester of pregnancy. In another aspect, at least one of the first non-placental biological sample and the second non-placental biological sample is taken prior to pregnancy.

The first non-placental biological sample and the second non-placental biological sample may bridge a therapeutic treatment or may bridge a designated period of time. In another aspect, the second non-placental biological sample may be a control sample.

A suitable method may also include identifying existence of the preeclampsia-related condition based, at least in part, on the comparison. A suitable method may also include administering a treatment based, at least in part, on the comparison.

In a further aspect, the at least one microRNA may be selected from the group consisting of hsa-miR-1, hsa-miR-1229, hsa-miR-1244, hsa-miR-1267, hsa-miR-132, hsa-miR-133b, hsa-miR-144-3p, hsa-miR-146a, hsa-miR-148a-3p, hsa-miR-155, hsa-miR-16, hsa-miR-181a, hsa-miR-193a-3p, hsa-miR-196a, hsa-miR-199a-5p, hsa-miR-199b-5p, hsa-miR-210, hsa-miR-219-5p, hsa-miR-221-5p, hsa-miR-223, hsa-miR-301a-3p, hsa-miR-30e-3p, hsa-miR-33a-5p, hsa-miR-340-5p, hsa-miR-424-5p, hsa-miR-513a-5p, hsa-miR-hsa-miR-575, hsa-miR-582-5p, hsa-miR-671-3p and hsa-miR-7-5p. The method may also include quantifying and comparing at least five microRNAs from the first non-placental biological sample and the second non-placental biological sample.

In additional aspects, the at least one microRNA bay be selected from the group consisting of hsa-miR-223, hsa-miR-7-5p, hsa-miR-148a-3p, hsa-miR-144-3p, hsa-miR-16 and hsa-miR-582-5p, may be selected from the group consisting of hsa-miR-144-3p, hsa-miR-148a-3p, hsa-miR-582-5p, hsa-miR-301a-3p, hsa-miR-146a, hsa-miR-575, hsa-miR-199a-5p, hsa-miR-133b and hsa-miR-424-5p, may be selected from the group consisting of hsa-miR-210, hsa-miR-1229, hsa-miR-223, hsa-miR-575 and hsa-miR-340-5p, may be selected from the group consisting of hsa-miR-1229, hsa-miR-146a, hsa-miR-210, hsa-miR-1244, hsa-miR-132 and hsa-miR-133b, may be selected from the group consisting of hsa-miR-513a-5p, hsa-miR-193a-3p, hsa-miR-7-5p, hsa-miR-575, hsa-miR-221-5p, hsa-miR-133b, hsa-miR-1 and hsa-miR-199a-5, may be selected from the group consisting of hsa-miR-513a-5p, hsa-miR-193a-3p, hsa-miR-221-5p, hsa-miR-340-5p, hsa-miR-7-5p, hsa-miR-575, hsa-miR-1, hsa-miR-199a-5p and hsa-miR-33a-5p, may be selected from the group consisting of hsa-miR-513a-5p, hsa-miR-193a-3p, hsa-miR-7-5p, hsa-miR-575, hsa-miR-221-5p, hsa-miR-133b, hsa-miR-1 and hsa-miR-199a-5p, may be selected from the group consisting of hsa-miR-575, hsa-miR-144-3p, hsa-miR-148a-3p, hsa-miR-210, hsa-miR-193a-3p, hsa-miR-199b-5p and hsa-miR-199a-5p, may be selected from the group consisting of miR575, miR144-3p, miR199a-5p, miR210, miR1229, miR133b, miR148a-3p, miR193a-3p, miR7-5p, miR223 and miR340-5p, may be selected from the group consisting of hsa-miR-144-3p, hsa-miR-582-5p, hsa-miR-30e-3p, hsa-miR-340-5p, hsa-miR-424-5p, hsa-miR-199a-5p, hsa-miR-199b-5p, hsa-miR-210, hsa-miR-221-5p, hsa-miR-33a-5p, hsa-miR-575, hsa-miR-7-5p, hsa-miR-1229, hsa-miR-1267 and hsa-miR-671-3p, or may be selected from the group consisting of hsa-miR-1181, hsa-miR-1296, hsa-miR-132, hsa-miR-136, hsa-miR-141, hsa-miR-142-5p, hsa-miR-144, hsa-miR-153, hsa-miR-1537, hsa-miR-193a-3p, hsa-miR-196a, hsa-miR-219-5p, hsa-miR-29b, hsa-miR-301a, hsa-miR-32, hsa-miR-33a, hsa-miR-545, hsa-miR-582-3p and hsa-miR-590-5p.

This disclosure also includes a diagnostic kit for characterizing a preeclampsia-related condition, such as a kit comprising a microarray including at least five microRNAs selected from the group consisting of hsa-miR-1, hsa-miR-1229, hsa-miR-1244, hsa-miR-1267, hsa-miR-132, hsa-miR-133b, hsa-miR-144-3p, hsa-miR-146a, hsa-miR-148a-3p, hsa-miR-155, hsa-miR-16, hsa-miR-181a, hsa-miR-193a-3p, hsa-miR-196a, hsa-miR-199a-5p, hsa-miR-199b-5p, hsa-miR-210, hsa-miR-219-5p, hsa-miR-221-5p, hsa-miR-223, hsa-miR-301a-3p, hsa-miR-30e-3p, hsa-miR-33a-5p, hsa-miR-340-5p, hsa-miR-424-5p, hsa-miR-513a-5p, hsa-miR-hsa-miR-575, hsa-miR-582-5p, hsa-miR-671-3p and hsa-miR-7-5p

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 1 lists 30 microRNAs demonstrating potential for predicting pregnancy outcome based on pregnancy outcome data, according to an embodiment;

FIG. 2 shows differences in preconception microRNA levels between Healthy and Preeclampsia patients of the microRNAs of FIG. 1;

FIG. 3 shows differences in preconception microRNA levels between Most High Risk Outcome Group and Lowest Risk Outcome Group, according to an embodiment;

FIG. 4 shows results associated with first trimester pregnancy testing, according to an embodiment;

FIG. 5 shows differences between sequential microRNA levels in early pregnancy between Preeclampsia and Healthy pregnancies, according to an embodiment;

FIG. 6 shows differences between preeclampsia and healthy microRNA level changes, according to an embodiment;

FIG. 7 shows differences in microRNA response between preeclampsia and healthy pregnancies with and without IVIG, according to an embodiment;

FIG. 8 correlates selected microRNAs associated with poor pregnancy outcomes with IVIG response, according to an embodiment;

FIG. 9 shows the Effect of Lymphocyte Immunotherapy, according to an embodiment;

FIG. 10 shows an exemplary scoring system as applied to selected mircoRNAs, according to an embodiment;

Figure 11:
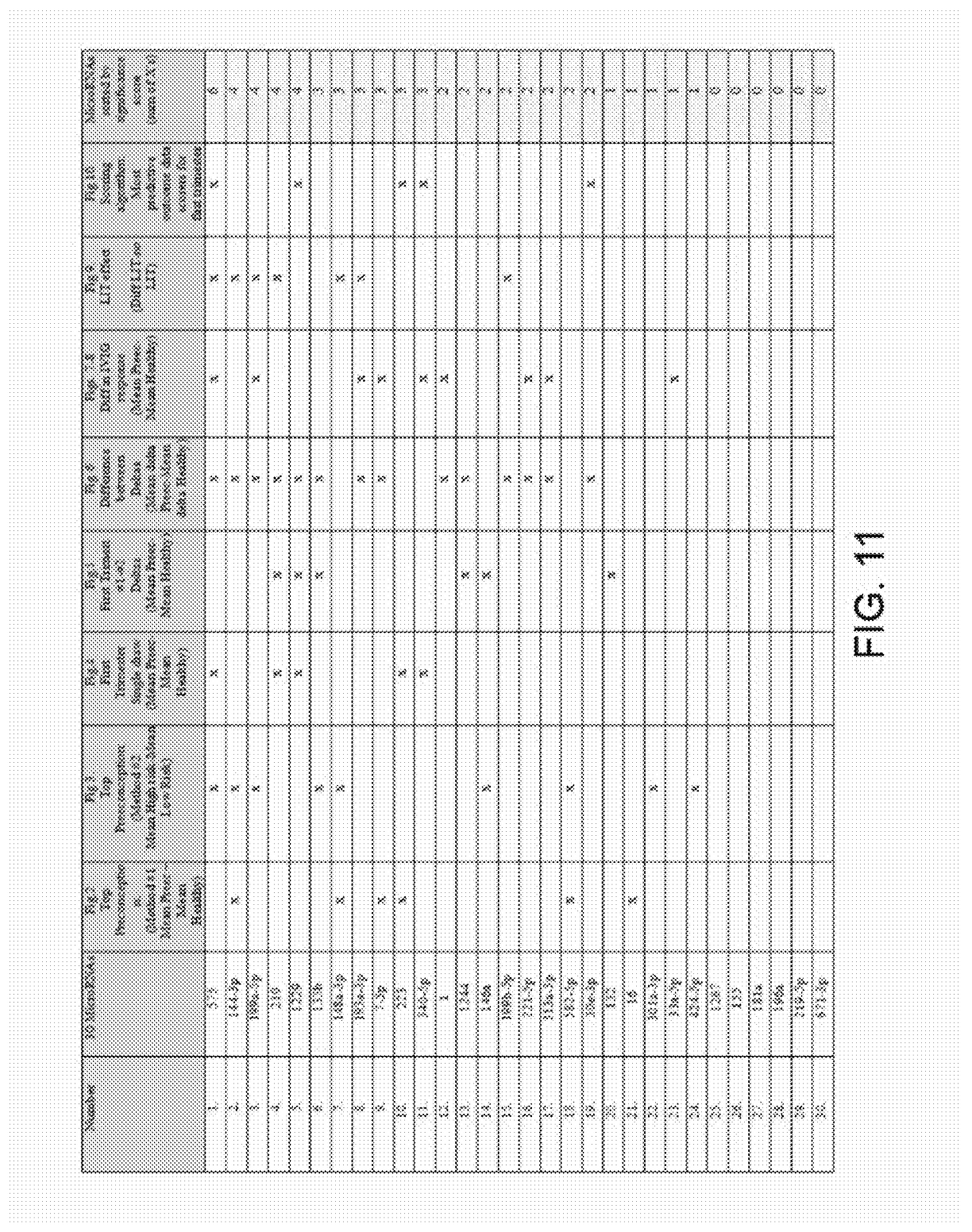

FIG. 11 shows microRNA significance as scored based on the frequency of the presence of the microRNA in the above figures;

FIGS. 12a and 12b show a microRNA pregnancy outcome predictor scoring system, according to an embodiment;

FIG. 13 shows exemplary ROC curve calculations for analysis of the microRNA preeclampsia scoring system, according to an embodiment;

FIGS. 15a and 15b show IVIG response data, according to an embodiment;

FIGS. 16a and 16b show pregnancy outcome data, according to an embodiment;

FIG. 17 shows 15 top microRNA marker candidates obtained from microarray analysis of 962 microRNAs, according to an embodiment;

FIG. 18 shows an exemplary microRNA pregnancy outcome predictor, according to an embodiment;

FIGS. 19a and 19b show microRNA IVIG response data combined with microRNA pregnancy outcome data, according to an embodiment;

FIGS. 20a and 20b show selected microRNAs having significant pregnancy outcome prediction, according to an embodiment;

FIG. 21 shows the top 25 differences between mean Healthy level and mean Preeclampsia and miscarriage levels before IVIG, according to an embodiment; and FIG. 22 shows the bottom 25 differences between mean Healthy level and mean Preeclampsia and miscarriage levels before IVIG, according to an embodiment.

DETAILED DESCRIPTION OF THE INVENTION

Figure 14:
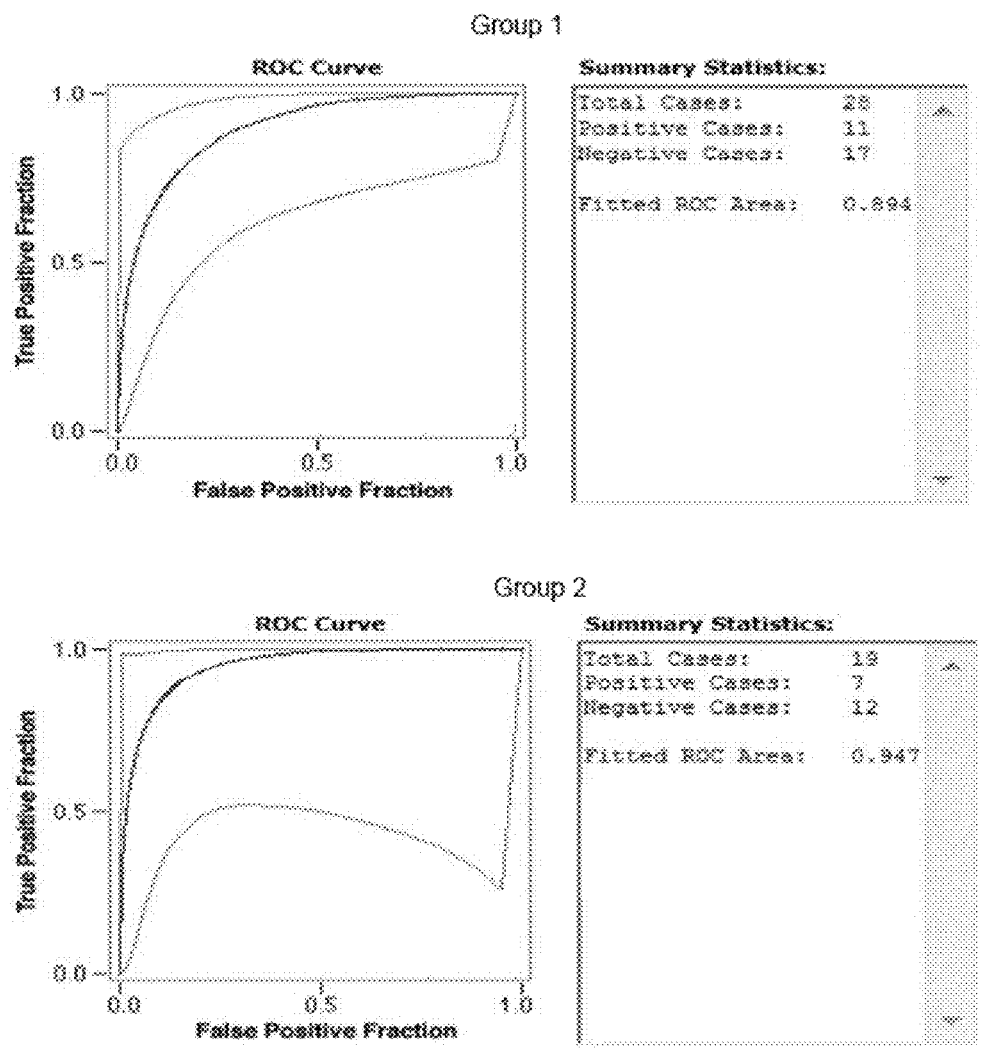
FIG. 14 shows ROC curve analyses of FIG. 13.

At the outset, it is to be understood that this disclosure is not limited to particularly exemplified materials, architectures, routines, methods or structures as such may, of course, vary. Thus, although a number of such option, similar or equivalent to those described herein, can be used in the practice of embodiments of this disclosure, the preferred materials and methods are described herein.

It is also to be understood that the terminology used herein is for the purpose of describing particular embodiments of this disclosure only and is not intended to be limiting.

This summary provides a listing of several embodiments of the presently disclosed subject matter. However, it should be understood that variations and permutations of these embodiments exist. This summary is intended to serve as exemplary of potential embodiments. Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification are approximations that can vary depending upon the desired properties sought to be obtained by the presently disclosed subject matter.

Herein, specific microRNAs may be identified by their prefix mir- and their identifier, such as mir-155. Sequences within an RNA transcript targeted by miRNAs may lie anywhere within the transcript. However, sequences within the 3' untranslated region are most common. MicroRNA nomenclature comprises a three-letter prefix "mir" followed by a number assigned generally in order of the description of the microRNA. In one convention when the "R" is lower case, the sequence refers to the pre-microRNA while when upper case is employed (miR), the mature form is indicated. Variants where the sequences vary by one or two bases may be designated by the letters "a" and "b". Occasionally, pre-microRNAs located within separate regions of the genome result in an identical mature microRNA. These microRNAs are distinguished by a numeric suffix ("miR-123-1" and "miR-123-2"). When two microRNAs originate from opposite arms of the same pre-microRNA they are designated with the suffix -3p or -5p according to whether the 3' or 5' strand is used. As used herein, the numeric code, e.g. "mir-123" shall include its variants such as mir-123-1, mir123-2, and the -3p and -5p variants. As used herein the term "pri-miRNA" shall mean the RNA targeted by the Drosha-Pasha complex. As used herein the term "pre-miRNA" shall mean the product of the cleavage by the Drosha-Pasha complex. As used herein, no distinction shall be made between sequences between the parent nomenclature for example mir-123 and any more selective sequence for example mir-123-5p and other than by description within the text.

As will be discussed below, examples of suitable microRNAs that may be used according to this disclosure include, without limitation, hsa-miR-582-3p MIMAT0004797 (SEQ ID NO: 1); hsa-miR-7-1-3p MIMAT0004553 (SEQ ID NO: 2); hsa-miR-340-5p MIMAT0004692 (SEQ ID NO: 3); hsa-miR-199b-3p MIMAT0004563 (SEQ ID NO: 4); hsa-miR-199a-3p MIMAT0000232 (SEQ ID NO: 5); hsa-miR-30e-5p MIMAT0000692 (SEQ ID NO: 6); hsa-miR-575 MIMAT0003240 (SEQ ID NO: 7); hsa-miR-7-5p MIMAT0000252 (SEQ ID NO: 8); hsa-miR-33a-3p MIMAT0004506 (SEQ ID NO: 9); hsa-miR-7-2-3p MIMAT0004554 (SEQ ID NO: 10); hsa-miR-199b-5p MIMAT0000263 (SEQ ID NO: 11); hsa-miR-144-5p MIMAT0004600 (SEQ ID NO: 12); hsa-miR-30e-3p MIMAT0000693 (SEQ ID NO: 13); hsa-miR-424-3p MIMAT0004749 (SEQ ID NO: 14); hsa-miR-33a-5p MIMAT0000091 (SEQ ID NO: 15); hsa-miR-671-3p MIMAT0004819 (SEQ ID NO: 16); hsa-miR-340-3p MIMAT0000750 (SEQ ID NO: 17); hsa-miR-1267 MIMAT0005921 (SEQ ID NO: 18); hsa-miR-1229-3p MIMAT0005584 (SEQ ID NO: 19); hsa-miR-424-5p MIMAT0001341 (SEQ ID NO: 20); hsa-miR-221-3p MIMAT0000278 (SEQ ID NO: 21); hsa-miR-1 MIMAT0000416 (SEQ ID NO: 22); hsa-miR-133b MIMAT0000770 (SEQ ID NO: 23); hsa-miR-221-5p MIMAT0004568 (SEQ ID NO: 24); hsa-miR-210 MIMAT0000267 (SEQ ID NO: 25); hsa-miR-1229-5p MIMAT0022942 (SEQ ID NO: 26); hsa-miR-671-5p MIMAT0003880 (SEQ ID NO: 27); hsa-miR-582-5p MIMAT0003247 (SEQ ID NO: 28); hsa-miR-199a-5p MIMAT0000231 (SEQ ID NO: 29); hsa-miR-144-3p MIMAT0000436 (SEQ ID NO: 30); hsa-miR-376a-5p MIMAT0003386 (SEQ ID NO: 31); hsa-miR-193a-3p MIMAT0000459 (SEQ ID NO: 32); hsa-miR-557 MIMAT0003221 (SEQ ID NO: 33); hsa-miR-34a-3p MIMAT0004557 (SEQ ID NO: 34); hsa-miR-584-5p MIMAT0003249 (SEQ ID NO: 35); hsa-miR-1244 MIMAT0005896 (SEQ ID NO: 36); hsa-miR-125b-1-3p MIMAT0004592 (SEQ ID NO: 37); hsa-miR-32-3p MIMAT0004505 (SEQ ID NO: 38); hsa-miR-933 MIMAT0004976 (SEQ ID NO: 39); hsa-miR-373-5p MIMAT0000725 (SEQ ID NO: 40); hsa-let-7b-5p MIMAT0000063 (SEQ ID NO: 41); hsa-miR-376a-3p MIMAT0000729 (SEQ ID NO: 42); hsa-miR-129-2-3p MIMAT0004605 (SEQ ID NO: 43); hsa-miR-548am-3p MIMAT0019076 (SEQ ID NO: 44); hsa-let-7f-5p MIMAT0000067 (SEQ ID NO: 45); hsa-miR-876-3p MIMAT0004925 (SEQ ID NO: 46); hsa-miR-371a-5p MIMAT0004687 (SEQ ID NO: 47); hsa-miR-423-5p MIMAT0004748 (SEQ ID NO: 48); hsa-miR-373-3p MIMAT0000726 (SEQ ID NO: 49); hsa-miR-152 MIMAT0000438 (SEQ ID NO: 50); hsa-miR-34a-5p MIMAT0000255 (SEQ ID NO: 51); hsa-miR-335-5p MIMAT0000765 (SEQ ID NO: 52); hsa-miR-181c-5p MIMAT0000258 (SEQ ID NO: 53); hsa-miR-125b-2-3p MIMAT0004603 (SEQ ID NO: 54); hsa-miR-548am-5p MIMAT0022740 (SEQ ID NO: 55); hsa-miR-338-3p MIMAT0000763 (SEQ ID NO: 56); hsa-miR-1225-5p MIMAT0005572 (SEQ ID NO: 57); hsa-miR-362-3p MIMAT0004683 (SEQ ID NO: 58); hsa-miR-767-5p MIMAT0003882 (SEQ ID NO: 59); hsa-miR-136-5p MIMAT0004606 (SEQ ID NO: 60); hsa-miR-29b-1-5p MIMAT0004514 (SEQ ID NO: 61); hsa-miR-29a-3p MIMAT0000086 (SEQ ID NO: 62); hsa-miR-92b-3p MIMAT0003218 (SEQ ID NO: 63); hsa-miR-362-5p MIMAT0000705 (SEQ ID NO: 64); hsa-miR-223-5p MIMAT0004570 (SEQ ID NO: 65); hsa-miR-505-3p MIMAT0002876 (SEQ ID NO: 66); hsa-miR-634 MIMAT0003304 (SEQ ID NO: 67); hsa-miR-371a-3p MIMAT0000723 (SEQ ID NO: 68); hsa-miR-129-1-3p MIMAT0004548 (SEQ ID NO: 69); hsa-miR-1238-5p MIMAT0022947 (SEQ ID NO: 70); hsa-miR-876-5p MIMAT0004924 (SEQ ID NO: 71); hsa-miR-181c-3p MIMAT0004559 (SEQ ID NO: 72); hsa-miR-338-5p MIMAT0004701 (SEQ ID NO: 73); hsa-miR-505-5p MIMAT0004776 (SEQ ID NO: 74); hsa-miR-335-3p MIMAT0004703 (SEQ ID NO: 75); hsa-miR-543 MIMAT0004954 (SEQ ID NO: 76); hsa-miR-223-3p MIMAT0000280 (SEQ ID NO: 77); hsa-miR-125b-5p MIMAT0000423 (SEQ ID NO: 78); hsa-miR-1238-3p MIMAT0005593 (SEQ ID NO: 79); hsa-miR-377-5p MIMAT0004689 (SEQ ID NO: 80); hsa-miR-584-3p MIMAT0022708 (SEQ ID NO: 81); hsa-miR-22-5p MIMAT0004495 (SEQ ID NO: 82); hsa-miR-376a-2-5p MIMAT0022928 (SEQ ID NO: 83); hsa-miR-301a-5p MIMAT0022696 (SEQ ID NO: 84); hsa-miR-548m MIMAT0005917 (SEQ ID NO: 85); hsa-miR-29b-3p MIMAT0000100 (SEQ ID NO: 86); hsa-miR-99a-3p MIMAT0004511 (SEQ ID NO: 87); hsa-miR-33b-3p MIMAT0004811 (SEQ ID NO: 88); hsa-miR-92b-5p MIMAT0004792 (SEQ ID NO: 89); hsa-miR-602 MIMAT0003270 (SEQ ID NO: 90); hsa-miR-1237-3p MIMAT0005592 (SEQ ID NO: 91); hsa-miR-129-5p MIMAT0000242 (SEQ ID NO: 92); hsa-miR-148b-3p MIMAT0000759 (SEQ ID NO: 93); hsa-miR-377-3p MIMAT0000730 (SEQ ID NO: 94); hsa-let-7b-3p MIMAT0004482 (SEQ ID NO: 95); hsa-miR-125a-5p MIMAT0000443 (SEQ ID NO: 96); hsa-miR-125a-3p MIMAT0004602 (SEQ ID NO: 97); hsa-miR-148b-5p MIMAT0004699 (SEQ ID NO: 98); hsa-miR-22-3p MIMAT0000077 (SEQ ID NO: 99); hsa-miR-1237-5p MIMAT0022946 (SEQ ID NO: 100); hsa-let-7f-1-3p MIMAT0004486 (SEQ ID NO: 101); hsa-miR-29a-5p MIMAT0004503 (SEQ ID NO: 102); hsa-miR-193a-5p MIMAT0004614 (SEQ ID NO: 103); hsa-miR-423-3p MIMAT0001340 (SEQ ID NO: 104); hsa-miR-191-3p MIMAT0001618 (SEQ ID NO: 105); hsa-miR-301a-3p MIMAT0000688 (SEQ ID NO: 106); hsa-miR-767-3p MIMAT0003883 (SEQ ID NO: 107); hsa-miR-563 MIMAT0003227 (SEQ ID NO: 108); hsa-miR-95 MIMAT0000094 (SEQ ID NO: 109); hsa-miR-1234-3p MIMAT0005589 (SEQ ID NO: 110); hsa-miR-1225-3p MIMAT0005573 (SEQ ID NO: 111); hsa-miR-136-5p MIMAT0000448 (SEQ ID NO: 112); hsa-miR-1234-5p MIMAT0022944 (SEQ ID NO: 113); hsa-miR-99a-5p MIMAT0000097 (SEQ ID NO: 114); hsa-miR-32-5p MIMAT0000090 (SEQ ID NO: 115); hsa-miR-191-5p MIMAT0000440 (SEQ ID NO: 116); hsa-miR-33b-5p MIMAT0003301 (SEQ ID NO: 117); hsa-mir-1-1 MI0000651 (SEQ ID NO: 118); hsa-mir-1-2 MI0000437 (SEQ ID NO: 119); hsa-mir-7-1 MI0000263 (SEQ ID NO: 120); hsa-mir-7-2 MI0000264 (SEQ ID NO: 121); hsa-mir-7-(SEQ ID NO:3 MI0000265 122); hsa-mir-30e MI0000749 (SEQ ID NO: 123); hsa-mir-33a MI0000091 (SEQ ID NO: 124); hsa-mir-133b MI0000822 (SEQ ID NO: 125); hsa-mir-144 MI0000460 (SEQ ID NO: 126); hsa-mir-199a-1 MI0000242 (SEQ ID NO: 127); hsa-mir-199a-2 MI0000281 (SEQ ID NO: 128); hsa-mir-199b MI0000282 (SEQ ID NO: 129); hsa-mir-210 MI0000286 (SEQ ID NO: 130); hsa-mir-221 MI0000298 (SEQ ID NO: 131); hsa-mir-340 MI0000802 (SEQ ID NO: 132); hsa-mir-424 MI0001446

(SEQ ID NO: 133); hsa-mir-575 MI0003582 (SEQ ID NO: 134); hsa-mir-582 MI0003589 (SEQ ID NO: 135); hsa-mir-671 MI0003760 (SEQ ID NO: 136); hsa-mir-1229 MI0006319 (SEQ ID NO: 137); hsa-mir-1267 MI0006404 (SEQ ID NO: 138); hsa-let-7a-3 MI0000062 (SEQ ID NO: 139); hsa-let-7e MI0000066 (SEQ ID NO: 140); hsa-mir-22 MI0000078 (SEQ ID NO: 141); hsa-mir-29a MI0000087 (SEQ ID NO: 142); hsa-mir-29b-1 MI0000105 (SEQ ID NO: 143); hsa-mir-32 MI0000090 (SEQ ID NO: 144); hsa-mir-33b MI0003646 (SEQ ID NO: 145); hsa-mir-34a MI0000268 (SEQ ID NO: 146); hsa-mir-92b MI0003560 (SEQ ID NO: 147); hsa-mir-95 MI0000097 (SEQ ID NO: 148); hsa-mir-99a MI0000101 (SEQ ID NO: 149); hsa-mir-125a MI0000469 (SEQ ID NO: 150); hsa-mir-125b-1 MI0000446 (SEQ ID NO: 151); hsa-mir-125b-2 MI0000470 (SEQ ID NO: 152); hsa-mir-129-1 MI0000252 (SEQ ID NO: 153); hsa-mir-129-2 MI0000473 (SEQ ID NO: 154); hsa-mir-136 MI0000475 (SEQ ID NO: 155); hsa-mir-148b MI0000811 (SEQ ID NO: 156); hsa-mir-152 MI0000462 (SEQ ID NO: 157); hsa-mir-181c MI0000271 (SEQ ID NO: 158); hsa-mir-191 MI0000465 (SEQ ID NO: 159); hsa-mir-193a MI0000487 (SEQ ID NO: 160); hsa-mir-223 MI0000300 (SEQ ID NO: 161); hsa-mir-301a MI0000745 (SEQ ID NO: 162); hsa-mir-335 MI0000816 (SEQ ID NO: 163); hsa-mir-338 MI0000814 (SEQ ID NO: 164); hsa-mir-362 MI0000762 (SEQ ID NO: 165); hsa-mir-371a MI0000779 (SEQ ID NO: 166); hsa-mir-373 MI0000781 (SEQ ID NO: 167); hsa-mir-376a-1 MI0000784 (SEQ ID NO: 168); hsa-mir-376a-2 MI0003529 (SEQ ID NO: 169); hsa-mir-377 MI0000785 (SEQ ID NO: 170); hsa-mir-423 MI0001445 (SEQ ID NO: 171); hsa-mir-425 MI0001448 (SEQ ID NO: 172); hsa-mir-505 MI0003190 (SEQ ID NO: 173); hsa-mir-543 MI0005565 (SEQ ID NO: 174); hsa-mir-548m MI0006400 (SEQ ID NO: 175); hsa-mir-557 MI0003563 (SEQ ID NO: 176); hsa-mir-563 MI0003569 (SEQ ID NO: 177); hsa-mir-584 MI0003591 (SEQ ID NO: 178); hsa-mir-602 MI0003615 (SEQ ID NO: 179); hsa-mir-634 MI0003649 (SEQ ID NO: 180); hsa-mir-767 MI0003763 (SEQ ID NO: 181); hsa-mir-876 MI0005542 (SEQ ID NO: 182); hsa-mir-933 MI0005755 (SEQ ID NO: 183); hsa-mir-1225 MI0006311 (SEQ ID NO: 184); hsa-mir-1234 MI0006324 (SEQ ID NO: 185); hsa-mir-1237 MI0006327 (SEQ ID NO: 186); hsa-mir-1238 MI0006328 (SEQ ID NO: 187); hsa-mir-1244-1 MI0006379 (SEQ ID NO: 188); hsa-mir-1244-2 MI0015974 (SEQ ID NO: 189); hsa-mir-1244-3 MI0015975 (SEQ ID NO: 190); and hsa-mir-1825 MI0008193 (SEQ ID NO: 191)

As used herein the term "placental site" shall refer to the discrete area of the maternal endometrium in direct contact with the implanting feto-placental unit. It is coextensive with the placenta. During pregnancy the stromal elements undergo decidual transformation wherein the elongated fibroblast like cells of the stroma are transformed into plump secretory-like cells.

Specific microRNA abbreviations may also include an additional prefix identifying the species of origin, such as hsa for homo sapiens. Although the primary embodiments described herein are directed to humans, one of skill in the art will appreciate that the techniques of this disclosure can be applied to other species.

Preeclampsia-related condition: As used herein the term "Preeclampsia-related condition" shall comprise one or more conditions selected from a group exemplified by but is not limited to preeclampsia and conditions associated with preeclampsia or related to preeclampsia by related etiology or symptoms including premature rupture of membranes (PROM), intrauterine growth retardation (IUGR), gestational diabetes, proteinuria, hypertension, edema, HELLP Syndrome, eclampsia, low birth weight, miscarriage, pregnancy-induced hypertension, Metabolic Syndrome associated with heart disease, pregnancy bleeding, placental abruption, placenta accreta, placental hemorrhage, placental infarction, preterm labor, preterm birth, stillbirth, excess or low amniotic fluid, subchorionic hemorrhage, recurrent pregnancy loss and anti-phospholipid antibody syndrome, thrombophilia, fetal thrombotic vasculopathy, villitis of unknown etiology, poor endometrial lining development, infertility and infertility in humans or other mammals. These conditions are correlated with changes preceding and following pregnancy and are understood to be within the scope of the invention.

The applicants have identified metabolic and signaling pathways that appear to be common to the conditions listed within the definition. Moreover, it is well understood in the art that these conditions share in common etiopathologic features and therefore may share common alterations in expression of microRNAs and microRNA profiles.

The term "control individual" as used herein has a special meaning. A "control individual" shall mean individuals of comparable characteristics such as age and sex who do not have preeclampsia and related conditions or pathology leading to said condition and are not at known risk of developing said condition. The term "control sample" as used herein shall mean a non-placental biological sample from the same source, such a peripheral blood, and collected under the same or comparable conditions as a patient sample comprising cells of the non-placental biological sample collected from a control individual that is processed and analyzed in the same manner as a patient sample.

It is further understood that the term "control sample" as used herein may represent the mathematical mean of multiple samples from control individuals wherein a number of samples considered sufficient by an individual of ordinary skill in the art are collected. Additional statistical parameters may be derived from said samples such as standard deviation of the mean. Said additional statistical parameters may be used for purposes of comparison of a patient test result with control samples to estimate the probability that the patient's test result represents an abnormal finding and, thereby suggests that the patient is suffering from preeclampsia and related conditions or risk of said condition. For purposes of simplicity the term may also be used in another way wherein a plurality of comparable, temporally separate, samples are collected and assayed from a single individual and compared with one another such that a first sample or a particular subsequent sample are compared as though the first is a control for the second, permitting assessment of a change in condition potentially as a function of the clinical state, or stage of pregnancy or as a result of therapeutic intervention.

Small non-coding RNA: As used herein the term "small, non-coding RNA" shall mean a polynucleotide ranging from about 18-31 RNA nucleotides not coding for a polypeptide. Small, non-coding RNAs are single-stranded RNA molecules of about 18-31 nucleotides in length, which regulate gene expression. Small non-coding RNAs are encoded by genes from whose DNA they are transcribed in a similar manner to mRNA that encode protein. Small non-coding RNA do not encode protein. Three forms have been described. Piwi-RNA comprise up to 31 nucleotides while si-RNA and miRNA comprise approximately 18-25 nucleotides. The genes are processed from RNA transcripts that are much longer than the mature non-coding RNA. miRNAs are initially transcribed as a transcript known as pri-miRNA comprising a cap and poly-A tail. It is subsequently processed into a much shorter transcript within the nucleus by a protein complex known as the Microprocessor complex. The complex containing an RNase III known as Drosha and an a double stranded RNA recognizing molecule known as Pasha recognize a stem-loop structure and cleave the pri-miRNA into a stem-loop structure of approximately 70 nucleotides known as pre-miRNA. Pre-miRNAs are escorted to the cytoplasm with the aid of Transportin-5. These pre-miRNAs are then processed into the mature miRNA in the cytoplasm by a second RNase III, Dicer initiating formation of a protein complex known as the RNA-induced silencing complex (RISC). Dicer-mediated cleavage generates two separate RNA semi-complementary strands, one of which is selected for integration into the RISC complex. The integrated strand, known as the guide strand, forms a complementary interaction with a target mRNA formed, most commonly, along a short 6-8 base region of the guide strand. The RISC complex generally aligns along a region of the 3' untranslated portion of the mRNA. Argonaute proteins within the RISC complex then act to cleave (degrade) or suppress translation of the mRNA polynucleotide generally depending upon the degree of miRNA complementarity. Nomenclature for miRNAs as used herein may be found in miRBase (www.mirbase.org). The entries represent the predicted hairpin portion of the miRNA transcript.

MicroRNA sequences are most commonly found within the introns of their host genes. They may also be found within exons and across exon-intron boundaries. These sequences are known to target at least 30 percent of all human genes, fine-tuning their expression. The final short sequence is generated through a series of cleavages involving two enzymes, Drosha and Dicer, from relatively long RNA primary RNA sequences.

miRNA Profiles: As used herein the term "miRNA Profile" shall mean a group comprising one or more microRNAs that can be used to distinguish two non-placental biological samples. Expression of miRNAs within any biologic sample is known to be quite variable though each microRNA, individually, might correlate with a clinical finding. To improve clinical correlation a plurality of microRNAs, each correlating with a clinical condition are viewed in aggregate. A comparison of their quantitative expression between any two clinical conditions, preferably where one is a normal or control, may be used to improve distinction between two clinical conditions. A variety of methods may be used to compare the patterns expressed between two clinical conditions such as providing individual numerical scores that can be compared, for example, as a sum.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods.

As used herein the term "heuristic" shall refer to experience-based techniques for problem solving. More specifically, it shall comprise techniques designed for solving problems based on experience such as those comprised in a database. Moreover, the techniques may involve a process of continual refinement wherein a problem-solving model is continually updated based upon accrual of additional data into the database. These techniques may be incorporated into computer algorithms.

Non-Placental Biological Sample: As used herein, the term "non-placental biological sample" shall mean maternal cells and derivatives thereof not collected from the placental site. Suitable techniques include isopycnic density-gradient centrifugation as well as monoclonal antibody paramagnetic bead conjugates for example used in techniques well known in the art. Isolated cells may be interrogated in batch assays assessing the total quantity of a specific microRNA that may be related to the average quantity expressed by cells of the individual cell type or maybe quantified by in situ hybridization. Advantage may be taken of the relative quantity of cell-comprised microRNA versus the quantity of microRNA comprised in the blood liquid phase as in plasma or serum-comprised vesicular structures. The relative quantity of microRNA in the former is very substantially greater than the later permitting assessment of cellular microRNA as a measured by total blood microRNA. The PAXgene blood RNA Tube™ is designed for the collection, storage, stabilization and transport of intracellular RNA. They may be used in conjunction with a nucleic acid purification kit (PAXgene Blood RNA Kit) for isolation of cellular microRNA.

A non-placental biological sample may be derived from a patient with a disease or being investigated for the propensity or likelihood of developing a disease or following pregnancy for a period of about six months. As used herein, the term "subject" refers to any mammal, including both human and other mammals. Preferably, the methods of the present invention are applied to human subjects.

All patents and references whether conventionally cited in the literature or addressed through internet links herein are incorporated in entirety by reference. All technical and scientific terms used within this description shall have the same meaning as commonly understood by those of ordinary skill in the art disclosed herein except where otherwise specifically defined. Following long-standing patent law convention, the terms "a", "an", and "the" refer to "one or more" when used in this application, including the claims. Thus, for example, reference to "a peptide" includes a plurality of such peptides, and so forth.

As referenced above, an unmet need remains to characterize a preeclampsia-related condition using a biological sample that may be readily collected. The techniques of this invention may include maternal cells available for interrogation that constitute a third compartment, the maternal cellular compartment not collected from the placental site. Conventionally, cells of this third compartment may not be expected to experience meaningful exposure to conditions experienced by the first and second compartments. In the mature placenta, maternal blood enters the uterus by arcuate, radial and spiral arteries before entering the intervillous space being drained by uterine veins and thence reentering maternal circulation. The intervillous space acts as a shunt during the later portions of pregnancy with only minimal exposure of maternal blood cells to placental conditions unlike non-migratory cells stationed within the second compartment. Because of trophoblast plugging during the first trimester, maternal blood, at least its cellular components, are redirected through myometrial shunt pathways, thereby avoiding exposure to the microenvironment of the placental site. Because these cells do not experience the local environment of the placental site, the prior art provides no indication that they may be expected to reflect a differentially expressed microRNA profile.

According to the techniques of this disclosure, individual microRNAs and microRNA profiles have been found to demonstrate differential expression patterns between patients with preeclampsia and related conditions or risk of developing said disorder and those with uneventful pregnancies. These differentially expressed microRNAs within maternal cells not collected from the placental site during pregnancy were analyzed using the DIANA-micro-T-CDS (v5.0) (accessed May 12, 2013 at http://diana.cslab.ece.ntua.gr/), providing unexpected results. Signaling and metabolic pathways regulated in aggregate by the differentially-expressed microRNAs included the Glycosaminoglycan biosynthesis (heparan sulfate pathway (hsa00534)), Mucin type O-Glycan biosynthesis pathway (hsa00512), the Wnt signaling pathway (hsa04310), the TGF-beta signaling pathway (hsa04350) and the ECM-receptor interaction (hsa04512) pathway. The prevailing teachings within the literature suggest their differential regulation in trophoblast and possibly maternal cells of the placental site. Conversely, there is no apparent teaching in the prior art of differential expression in maternal cells outside of the placental site.

Clinicians may be presented by patients in whom an immunotherapy is thought to be useful. Appropriate selection of patients for immunotherapy may be central to effective therapeutic intervention. Appropriate patients for such intervention may be selected by the use of various PBMC in vitro markers. According to the present disclosure, quantification of various microRNAs and patterns of microRNA change in PBMCs at various time points prior to and following immunotherapeutic intervention may be performed. These microRNA "signatures" support the clinical diagnosis, through identification of candidates for particular therapeutic intervention(s), and prognosticate outcome in patients with various disorders, for example, pregnancy-related disorders. Moreover, it is contemplated that the diagnostic procedures of the present invention may be applied to different clinical conditions and different immunotherapeutic interventions. Their use simplifies complex diagnostic strategies into a single procedure and provides information heretofore unavailable.

While initial studies and examples described herein substantially relate to pregnancy and disorders of the reproductive system of women, these studies should be regarded as exemplary of the broader application of the present invention to other disease states involving other organ systems. Moreover, while some descriptions relate to changes in the expression of one or more microRNAs before and after a selected intervention, it is understood that the present invention is applicable to measurements made at a single time point whether before or after a contemplated intervention.

A novel aspect of the present invention is the separation of patients into groups distinguishable by characteristic changes in single or multiple microRNAs following the selected intervention. Identification of patients belonging to microRNA response groups is associated with improved efficacy, prognosis and utility of particular immunotherapeutic intervention(s). Moreover, quantitative levels of certain microRNAs and patterns of change within microRNAs may predict patient response group(s) and post-therapy levels may have additional predictive value. Use of microRNA patterns responsive to therapeutic intervention or predictive thereof provides useful insights into management unavailable through identification of markers directly related to the pathologic process.

The presence, absence or level of the DNA-interacting proteins is the primary regulator of the effect of such native DNA interactions. With respect to purification, it is clear that such interactions may occur only in the native, unpurified form of the DNA where additional interactions with auxiliary-interacting proteins effecting of a result of such an interaction. The "state" of a cell e.g. proliferation, stressed, differentiation, is not comprised within such sequences but rather the concerted interaction of DNA and the interacting proteins. Separation of DNA by isolation or disruption in situ by denaturing processes including heat or chemicals or by the interaction of invasive polynucleotide probes (locked-DNA, PNAs etc.) disrupts these interactions. In terms of RNA, the effects are even more clear. It is now well established that RNA molecules form non-canonic interactions resulting in unexpected activities such as found in ribozymes. Here essential interactions with specific divalent cations are required for assumption of a catalytic conformation. MicroRNAs require interaction with proteins that must be available in the appropriate format.

The process of discovery involved is a transformative step. The procedure used to discover the microRNAs of this invention may involve two or more testing points, such as preceding and following an intervention designed to perturb the system or after a given period of time to provide insight into changes in the course of the preeclampsia-related condition. MicroRNAs were identified that demonstrated markedly different behavior following the perturbing intervention. The intervention of this invention was transformative resulting in a distinguishable response amongst selected microRNAs between different clinical subsets. Moreover, a single testing done prior to intervention reveals multiple microRNAs, mainly the same microRNAs showing distinguishable changes between clinical subgroups may be used to predict membership amongst clinical subgroups.

Quantification of microRNAs provides insights into physiologic and pathologic processes wherein their levels are measurably distinguishable from the "steady-state". The interactions between genetic and environmental factors are understood to result in an expressed phenotype not predictable by genetic factors alone. In the last few years, interactions at the level of microRNAs and environmental factors have become apparent.

Thus it is understood profile in the present invention that a miRNA may be used to differentiate between a condition 1 and another condition 2. For example, condition 1 may be found in a patient at a given time point. Condition 2 may be any of a number of conditions to which condition 1 is compared. For example, condition 2 may be derived from the corresponding non-placental biological sample at the same time point during pregnancy or peri-pregnancy period. It is understood that condition 2 may be a composite or average of a plurality of microRNAs. Condition 2 may represent a second time point wherein differences between condition 1 and condition 2 are assessed.

The common miRNA or non-coding RNA signature profile can be calculated "on-the-fly" from a plurality of miRNA-profiles that are stored, e.g. in database. As the database increased in size, the predictive value of the signature profile becomes stronger, with a greater number and accuracy of predictions becoming possible. The common miRNA signature profile which is able to differentiate between a condition 1 and another condition 2 is changing as soon as an new profile is added to the database which is relevant to either to state of health 1 or another condition 2. In this respect it is different from a predetermined set of miRNAs (see above). Furthermore, the basis for generating the common miRNA signature profile—hence the miRNA profiles stored in the database—is generated from capture probes, e.g. on a matrix that is representing as much as possible different capture probes for detecting as much as possible, ideally all known, miRNAs.

It is understood that data may be collected together with clinical information including the conditions, times within pregnancy or peri-pregnancy period, treatment and symptoms in a database that is dynamic and growing with accumulation of data. Analysis of a microRNA signature of a non-placental biological sample may be compared with corresponding microRNA signature derived from the database. Mathematical approaches to analysis of data and methods for comparison are well known to those skilled in the art. These methods include, for example, Signal to Noise ratios, Fold Quotients, correlation and statistical methods as hypothesis tests such as t-test, the Wilcoxon-Mann-Whitney test, the Area under the Receiver operator Characteristics Curve Information. Theory approaches, for example, the Mutual Information, Cross-entropy, Probability theory, for example, joint and conditional probabilities are also appropriate. Combinations and modifications of the previously mentioned examples are understood to be within the scope of the present invention. Heuristic methods may be applied as the database expands.

The information collected from non-placental biological samples may be used to estimate for each biomarker the diagnostic content or value. Usually, however, this diagnostic value of only one biomarker is too small to get a highly accurate diagnosis with accuracy rates, specificities and sensitivities beyond the 90% barrier. It may be noted that the diagnostic content for suitable miRNAs can be found in the tables in FIGS. 2 and 5, described below. These tables includes the miRNAs with the sequences, and the significance value as computed by a t-test and further statistical measures.

In one embodiment, the invention comprises a method for diagnosing a disease or condition, comprising the steps (1) quantifying miRNAs within a predetermined miRNA profile in a non-placental biological sample from an individual (patient or subject); and (2) comparing said miRNA profile to a reference, wherein the reference is the set of quantifications of said miRNA profile of one or the average of many individuals that are without disease or have a second condition to which the first condition is to be distinguished or compared. The comparison permits diagnosis. Wherein the comparison is between two temporally separate non-placental biological samples of the same individual, it may be used to determine clinical progress. Wherein the two non-placental biological samples of the same individual span a therapeutic intervention, the relative efficacy of therapy may be assessed.

In one embodiment, the method comprises providing a non-placental biological sample from a subject with a history of preeclampsia and related conditions or risk of such disorder or related disorder said sample being derived from cells of the biologic sample, for example, derived from peripheral blood or bone marrow, and then isolating mononuclear cells as taught by Boyum (Boyum A 1983. Isolation of human blood monocytes with Nycodenz, a new non-ionic iodinated gradient medium. Scand J Immunol 17: 429-436) and then determining the amount of non-coding RNA such as preferably microRNA (microRNAs) and comparing to the amount of the corresponding RNA in the sample to similarly treated non-placental biological sample from control individuals. In addition, the method can comprise quantification of a plurality of individual microRNAs from the non-placental biological sample and quantifying the individual microRNAs and comparing the amount of microRNAs to corresponding microRNA control levels. The subject is then diagnosed as having preeclampsia and related conditions or risk of developing such a disorder if there is differential expression in the amount of one or more of the RNAs from the sample as compared to corresponding RNA control levels. In some embodiments, the method further comprises selecting a treatment or modifying a treatment based on the amount of the one or more RNAs determined. This determination may be based upon assessment of specific individual or combinations of the individual microRNAs.

Methods for quantifying or semi-quantifying microRNA are well known in the art. These include but are not limited to nucleic acid hybridization techniques well known in the art for example performed using a solid phase support comprising specific, bound polynucleotides complementary to the target microRNA sequence. RNA isolated from a biologic sample may be reversed transcribed into DNA and conjugated with a detectable label and thence contacted with the anchored probes under hybridizing conditions and scanned by a detection system permitting discrete quantification of signals. It is understood that probe sequences may also be complementary to target sequences comprising SNPs. Moreover, it is understood that probe sequences may be complementary to pre-microRNA and pri-microRNA regions of specific microRNAs. Techniques comprising the polymerase chain reaction, preferably those incorporating real time techniques wherein amplification products are detected through labeled probes or utilizing non-specific dye amplicon-binding dyes such as cyber green.

Further, RNA may be extracted from cells isolated cells selected by said means may be prepared by extraction according to instructions from the manufacturer (Qiagen catalogue 763134). microRNA such as for mir-155 may be detected and quantified by PCR (polymerase chain reaction) by the method described by Chen et al. (http://www3.appliedbiosystems.com/cms/groups/mcb_marketing/documents/generaldocuments/cms_040548.pdf downloaded May 11, 2010). Primers and reagents may be selected for individual microRNAs from those described in product overview (http://www3.appliedbiosystems.com/cms/groups/mcb_marketing/documents/generaldocuments/cms_068884.pdf downloaded May 11, 2010). This document provides information teaching the detection and quantification of individual microRNAs.

In one aspect of the invention, an expression profile of a predetermined set of miRNAs is identified. It is understood that expression profiles may consist of the entirety of all known microRNAs incorporated into a microarray chip. Any of several methods may be used for quantification or semi-quantification. Determination of an expression profile may be performed by quantitative or semi-quantitative determination of a panel of microRNAs in patients affected by a condition to be assessed and in individuals without said condition. Alternatively, determination of an expression profile that may be used to determine progress of a condition may be determined in a similar manner wherein comparison is made by quantitative or semi-quantitative differences between the two time points. Separate expression profiles may be determined in a similar manner wherein the two time points are separated by a therapeutic intervention. In a similar manner individual expression profiles may be determined at different time points particularly during the course of pregnancy including time points within 6 months preceding or following pregnancy by a term of approximately six months. Panels of microRNAs to be assessed selected a priori or they may comprise large collections intended to include all currently known microRNAs such as in a microarray. The determination may be carried out by any means for determining nucleic acids.

Selective interrogation of subsets of cells of the non-placental biological sample can impart additional information. In a preferred embodiment, any leukocyte population, for example, monocytes, lymphocytes, or granulocyte or cell fragments such as platelets, may be segregated by means well known in the art permits selective quantification of microRNAs within that cell population. Further, for example, lymphocyte subpopulations, themselves, can be individually interrogated following their selective isolation by such techniques, for example, flow cytometric sorting following interaction with fluorescently labeled monoclonal antibody combinations that are capable of discreetly characterizing the individual subclasses. For example, T regulatory cells may be contacted under selective binding conditions with fluorescently labeled anti-CD3, CD4, CD25 and CD127 and selected by their expression of CD3, CD4, CD25 and absence or low expression of CD127.

A novel aspect of the present invention is the separation of patients into groups distinguishable by characteristic changes in single or multiple microRNAs following the selected therapeutic intervention. Identification of patients belonging to microRNA response groups is associated with improved efficacy, prognosis and utility of particular therapeutic intervention(s). Moreover, quantitative levels of certain microRNAs and patterns of change within microRNAs may predict patient response group(s) and post-therapy levels may have additional predictive value. Use of microRNA patterns responsive to therapeutic intervention or predictive thereof provides useful insights into management unavailable through identification of markers directly related to the pathologic process.

Techniques for assessing microRNA may general include those that quantify or semi-quantify total microRNA in a biologic specimen. Alternatively, techniques such as in situ hybridization using probes specific for individual microRNAs may be used. These techniques permit identification of individual cells comprising the quantified microRNA. In one embodiment these techniques involve the use of multiple probes. A first set comprising one or a plurality of uniquely labeled probes may be used to identify cells. A second set of uniquely labeled probes microRNA-complementary probes may be used to quantify specific microRNAs comprised by said cell. Probes used to identify a cell may be monoclonal antibodies conjugated to fluorescent dyes. Probes used to quantify microRNAs comprised by said cells are conjugated to unique fluorescent dyes. Preferably probes are nucleic acid sequences complementary to selected regions of the microRNA or portions of the precursors of the microRNA. The probes may be comprised of synthetic polynucleotide sequences such as locked-nucleic acids. Detection methods may comprise flow cytometry or image cytometry. These techniques are advantageous. They can, for example, distinguish total microRNA levels in a biologic sample into patterns wherein relatively small quantities of a microRNA are broadly expressed amongst cells within a biologic sample or large quantities expressed within a selected and identifiable small population of cells within a biologic sample. It is understood that in situ hybridization techniques may also be used on suitably prepared tissue samples. Techniques are known and practicable by those of ordinary skill in the art.

Prior to analysis of a non-placental biological sample, nucleic acid such as microRNA generally may be isolated. In embodiments including in situ hybridization, the cellular or tissue structure may be left intact. Steps employed comprise a number of separable operations that include concentration, suspension, extraction of intracellular material wherein these steps are well known to those of ordinary skill in the art. Numerous commercially available kits that comprise reagents and instructions are available and are specifically designed for efficient isolation of RNA of the small size of miRNA.

Two exemplary methods for isolating RNA include phenol-based extraction and silica matrix or glass fiber filter (GFF)-based binding. Phenol-based reagents comprise various components that denaturants sample constituents, possess the capacity to inhibit RNase's that permit cell and tissue disruption that is followed by steps that permit separation of the RNA from other constituents of the sample. Commercial reagents and kits may be configured to recover short RNA polynucleotides of microRNA length. Extraction procedures such as those using Trizol or TriReagent are useful wherein both long and short RNA polynucleotides are desired. Any method is within the scope of this invention.

It is understood herein that detection of miRNA may include detection of the presence or absence of a specific microRNA within a non-placental biological sample, and more preferably its quantification. The methods may produce quantitative or semi-quantitative results. It is understood that relative quantification wherein comparative levels between the sample of the patient is related to the level in a control or other sample particularly wherein sequential samples are assayed. Any detection method well known to those skilled in the art falls within the scope of the invention. Hybridization, preferably where a polynucleotide complimentary to the target polynucleotide is labeled, may be used to detect the target strand. The polymerase chain reaction incorporating labeled probes, electrophoresis or other detection strategy may be employed. Sequencing of target strands may also be used.

It is apparent from the gene structure incorporating a small non-coding RNA that they are affected in similar ways to those gene protein-encoding genes. For example, single nucleotide polymorphisms (SNPs) are well-described variants identified within genes and affect their translation and stability. In a similar manner, SNPs affect translation and functionality of small non-coding RNAs. These variations may be within the small non-coding RNA itself or within the adjacent regions within the gene or nearby regions that affect their transcription as well as corresponding SNPs in the target mRNA. It appears that the number of human microRNAs may exceed 1000. It is understood that interrogation of microRNAs and their precursors including nearby sequences that may affect their transcription with probes and primers specific for SNPs are within the scope of the invention.

Single nucleotide polymorphisms (SNP) within both microRNAs and their flanking regions and target mRNAs may alter target specificity resulting in loss or diminished effect between wild-type species and SNP-comprising counterparts. Further such polymorphisms may generate new mRNA targets interactions. These polymorphisms may be result in altered efficiency of microRNA regulation of target mRNAs. Further, Polymorphisms may potentially affect microRNA-mediated regulation of the cell can be present in the 3'-UTR of a microRNA target gene. Additional polymorphisms may also be present in the genes involved in microRNA biogenesis as well as in pri-, pre- and mature-microRNA sequences. The consequences of such polymorphisms in processed microRNAs may have profound effects on the expression of a multiplicity of target genes and have serious consequences, whereas a polymorphism in microRNA target site, in the 3'-UTR of the target mRNA, may be more target and/or pathway specific.

Nucleic acid characterization and quantification are used to assess the probability of success of a particular therapeutic intervention. It is the goal of personalized medicine to identify patients whom are likely, or conversely unlikely to respond to a candidate therapy. Cost, side-effects and improved therapeutic response are accepted reasons for pursuing nucleic acid testing as a means of selecting therapies and for following the course of therapy. Not only might quantification of microRNAs be helpful in identifying patients suffering from, but such quantifications would be of corresponding assistance in selecting and directing therapeutic choices and monitoring their effects in a virtually unlimited variety of disorders.

In one embodiment, an individual of ordinary skill in the art using a human microRNA array from Agilant Technologies (for example cat. G4471A-029297) and following the directions of the manufacturer) quantifies all known human microRNAs on specimens RNA extracted from cells of the non-placental biological sample according to instructions of the microarray manufacturer. Blood collected is drawn into heparinized tubes and maintained at room temperature preferably for approximately 24 hours prior to isolation of cells. RNA sampling and extraction: cells or sorted cell populations (<1×10^7 viable cells) were collected in 1 ml TRIzol (Invitrogen) and stored at −80 c until use). Total RNA was isolated according to the TRIzol protocol (Invitrogen) or RNeasy Mini Kit (Qiagen). For using the RNeasy Mini Kit, the entire procedure was carried out at room temperature with the QIAcube automated robot (Qiagen). Total RNA yield was assessed using the Thermo Scientific NanoDrop 1000 micro-volume spectrophotometer (absorbance at 260 nm and the ratio of 260/280 and 260/230). RNA integrity was assessed using the Agilent's Bioanalyzer NANO Lab-on-Chip instrument (Agilent). MicroRNA Microarray processing. The microRNA microarray data was normalized by using the Agilent's GeneSpring GX v11.5.1 (see the link) (http://www.chem.agilent.com/en-US/Products-Services/Software-Informatics/GeneSpring-GX/pages/default.aspx) downloaded Oct. 7, 2012.

Accordingly, embodiments of the invention may include the use of at least one microRNA selected from hsa-let-7e, mir-1, hsa-mir-1181, hsa-miR-1183, hsa-miR-1224-5p, hsa-miR-127-3p, hsa-mir-1296, hsa-mir-132, hsa-mir-136, hsa-miR-139-3p, hsa-mir-141, hsa-miR-142-3p, hsa-miR-142-5p, hsa-mir-144, hsa-mir-153, hsa-mir-1537, hsa-miR-154, hsa-miR-191, hsa-mir-193a-3p, hsa-miR-19a, hsa-mir-219-5p, hsa-mir-29b, hsa-mir-301a, hsa-miR-301b, hsa-miR-30e, hsa-mir-32, hsa-mir-33a, hsa-miR-340, hsa-miR-362-3p, hsa-miR-371-5p, hsa-377, hsa-miR-423-3p, hsa-miR-432, hsa-mir-513a-5p, hsa-mir-545, hsa-miR-548a-5p, hsa-miR-574-5p, hsa-mir-582-3p, hsa-mir-590-5p, hsa-mir-15a, hsa-mir-548c-5p, hsa-mir-1225-3p, hsa-mir-29b, hsa-mir-21, hsa-mir-1237, hsa-mir-101, hsa-mir-1539, hsa-mir-557, hsa-mir-125a-3p and hsa-mir-423-5p. In another aspect, the microRNA is selected from hsa-mir-136, hsa-mir-141, hsa-mir-142-5p, hsa-mir-144, hsa-mir-153, hsa-mir-1537, hsa-mir-193a-3p, hsa-mir-219-5p, hsa-mir-29b, hsa-mir-301a, hsa-mir-32, hsa-mir-33a, hsa-mir-545, hsa-mir-582-3p, hsa-mir-590-5p, hsa-mir-1181, hsa-mir-513a-5p, hsa-mir-132 and hsa-mir-1296. In another aspect, the microRNA is selected from hsa-miR-144, hsa-miR-582-5p, hsa-miR-30e-3p, hsa-miR-340-5p, hsa-miR-424-5p, hsa-miR-199a-5p, hsa-miR-199b-5p, hsa-miR-210, hsa-miR-221-5p, hsa-miR-33a-5p, hsa-miR-575, hsa-miR-7-5p, hsa-miR-1229, hsa-miR-1267, hsa-miR-671-3p, hsa-miR-1244, hsa-miR-1 and hsa-miR-133b. In another aspect, the at least one microRNA may be mir-1229 or mir-671-3p. In yet another aspect, quantifying and comparing may include using at least four microRNAs selected from the group consisting of miR-7-5p, miR-1229, miR-1267, miR-671-3p, miR-340-5p, hsa-miR-1, hsa-miR-133b and hsa-miR-33a-5p.

Using the techniques described above, a number of microRNAs may be identified and evaluated based on their relative expression in patients experiencing a preeclampsia-related condition and may be compared to corresponding expression levels of such microRNAs in patient exhibiting a normal pregnancy. Details regarding the identification and expression of exemplary micoRNAs are given in FIGS. 1-22, as described below.

FIG. 1 lists 30 microRNAs selected as demonstrating potential for predicting pregnancy outcome based on pregnancy outcome data as described in PCT/US12/61994 filed Oct. 25, 2012. Accordingly, in one embodiment, at least one microRNA may be selected from the group consisting of hsa-miR-1, hsa-miR-1229, hsa-miR-1244, hsa-miR-1267, hsa-miR-132, hsa-miR-133b, hsa-miR-144-3p, hsa-miR-146a, hsa-miR-148a-3p, hsa-miR-155, hsa-miR-16, hsa-miR-181a, hsa-miR-193a-3p, hsa-miR-196a, hsa-miR-199a-5p, hsa-miR-199b-5p, hsa-miR-210, hsa-miR-219-5p, hsa-miR-221-5p, hsa-miR-223, hsa-miR-301a-3p, hsa-miR-30e-3p, hsa-miR-33a-5p, hsa-miR-340-5p, hsa-miR-424-5p, hsa-miR-513a-5p, hsa-miR-hsa-miR-575, hsa-miR-582-5p, hsa-miR-671-3p and hsa-miR-7-5p.

FIG. 2 shows the differences in preconception microRNA levels between Healthy and Preeclampsia patients of the microRNAs of FIG. 1. The 30 selected microRNAs CT levels (The term "CT" in real time PCR means the cycle threshold number at which the amplified PCR product becomes detectable) were measured at a single preconception blood draw (mean 60.7±53.6 days before the conception cycle LMP (last menstrual period) day) for each of 29 patients (14 preeclampsia patients, 15 healthy patients). Mean preeclampsia and healthy microRNA CT level differences are sorted from highest to lowest. The absolute value of the miR CT differences were divided by average SD (average SD means the sum of the standard deviations (SD) divided by 2). The most predictive microRNAs of pregnancy outcome have a value ≥1 (marked with X). Based on these data, miR-223, miR-7-5p, miR 148a-3p, miR-144-3p, miR7-5p, miR-16 and 582-5p were found to be the most useful preconception microRNAs for predicting pregnancy outcome of the 30 microRNAs tested. Accordingly, in one embodiment, at least one microRNA may be selected from the group consisting of.

FIG. 3 shows differences in preconception microRNA levels between Most High Risk Outcome Group and Lowest Risk Outcome Group. As an additional analysis, the differences between the "Most high risk group" (Preeclampsia despite using IVIG at a positive pregnancy test) and the "Lowest risk group" (Healthy outcome despite no IVIG used at a positive pregnancy test) were calculated. The mean preconception values of these two groups were sorted from highest to lowest. Significant microRNAs had a difference between mean preeclampsia and mean healthy levels with an absolute value difference set at ≥1.0 (marked with XX). It is notable that miR 144-3p, 148a-3p and 582-5p are again on the top list of microRNA preconception predictors, similar to results in FIG. 2. Accordingly, in one embodiment, at least one microRNA may be selected from the group consisting of hsa-miR-144-3p, hsa-miR-148a-3p, hsa-miR-582-5p, hsa-miR-301a-3p, hsa-miR-146a, hsa-miR-575, hsa-miR-199a-5p, hsa-miR-133b and hsa-miR-424-5p.

FIG. 4 shows results associated with first trimester pregnancy testing. The mean differences between first trimester preeclampsia and healthy miR CT single levels at 30-85 days pregnant (mean 60.6±15.0 days) were calculated. No IVIG was used with these samples. The miR CT differences are sorted from largest to smallest. The most significant microRNAs for outcome prediction from early pregnancy were set at an absolute value difference ≥1.0 (marked XXX). The top five microRNAs (highlighted microRNAs) were included in one exemplary scoring system for predicting preeclampsia risk in early pregnancy, as discussed below with regard to FIG. 11. Accordingly, in one embodiment, at least one microRNA may be selected from the group consisting of hsa-miR-210, hsa-miR-1229, hsa-miR-223, hsa-miR-575 and hsa-miR-340-5p.

FIG. 5 shows differences between sequential microRNA levels in early pregnancy between Preeclampsia and Healthy pregnancies (no IVIG). In addition to single pregnancy blood draws, sequential blood draws were investigated to observe patterns of microRNA change in response to pregnancy. Sequential microRNA levels with two blood draws were tracked at approximately 22 days apart. Pregnancy blood draw #1 and draw #2 levels (second blood draw subtract first blood draw) were sorted by preeclampsia and healthy differences in untreated samples. The mean day of first blood draw was 50.2±20.1 days pregnant. The mean day of second blood draw was 72.0±21.7 days pregnant. The microRNA levels are sorted from most increased to most decreased level. The most significant microRNAs were set at an absolute value mean difference ≥1.5 (designated by *). These data may help determine which changes in microRNA levels predict pregnancy outcome without contamination from a therapy effect. Accordingly, in one embodiment, at least one microRNA may be selected from the group consisting of hsa-miR-1229, hsa-miR-146a, hsa-miR-210, hsa-miR-1244, hsa-miR-132 and hsa-miR-133b.

FIG. 6 shows differences between preeclampsia and healthy microRNA level changes, such that "differences in change") were measured. Differences between Preeclampsia and Healthy changes were sorted from most increased change to most decreased change. This data may show how Healthy microRNA "changes" compare to Preeclampsia microRNA "changes". This comparison contributes information about what microRNA movement patterns may need to be treated if a healthy pregnancy outcome is desired. Again, all patients were not exposed to IVIG. All changes were therefore a result of the pregnancy condition itself. With this in mind, it is notable that microRNAs that move as a result of the pregnancy condition are also microRNAs that respond well to IVIG as shown in FIG. 7. These dual purpose microRNAs are marked with **. Accordingly, in one embodiment, at least one microRNA may be selected from the group consisting of hsa-miR-513a-5p, hsa-miR-193a-3p, hsa-miR-7-5p, hsa-miR-575, hsa-miR-221-5p, hsa-miR-133b, hsa-miR-1 and hsa-miR-199a-5.

FIG. 7 shows differences in microRNA response between preeclampsia and healthy pregnancies with and without IVIG to detect group differences in IVIG response. In addition to observing differences in microRNA behavior between preeclampsia and healthy pregnancies, differences in IVIG response between preeclampsia and healthy pregnancies were also reviewed. The deltas of healthy patients using IVIG were compared to those not using IVIG (mean gestational age of first blood draw 62.4±18.8 days; of second blood draw 86.7.0±21.4 days). The deltas of preeclampsia patients using IVIG were then compared to those not using IVIG (mean gestational age of first blood draw 69.0±18.8 days; of second blood draw 97.4±40.2 days). Delta differences of patients in each outcome group using IVIG were compared to those not using IVIG and the results were sorted from largest difference to smallest difference. This demonstrates the "IVIG effect" on specific microRNA CT levels with different pregnancy outcomes. It is notable that the opposite" IVIG effect" (opposite movement of highlighted miRs) in the different outcome groups (marked with * Healthy pregnancy decrease/preeclampsia increase and Healthy pregnancy increase/Preeclampsia decrease). It is significant to note that many of these highlighted "IVIG effect" MicroRNAs are associated with differential pregnancy outcome in untreated pregnancies as discussed with regard to FIG. 6. This implies that IVIG may be useful as a clinical tool for "correcting" or "adjusting" high risk microRNA patterns once they are diagnosed, adding to the value of the microRNA test as treatment monitoring tool as well as a diagnostic tool. Accordingly, in one embodiment, at least one microRNA may be selected from the group consisting of hsa-miR-513a-5p, hsa-miR-193a-3p, hsa-miR-221-5p, hsa-miR-340-5p, hsa-miR-7-5p, hsa-miR-575, hsa-miR-1, hsa-miR-199a-5p and hsa-miR-33a-5p.

FIG. 8 correlates selected microRNAs associated with poor pregnancy outcomes with IVIG response. As shown, column A identifies mircroRNAs exhibiting the most disregulated results of pathologic microRNA patterns associated with poor pregnancy outcome and column B includes the IVIG response data from FIG. 7, that may indicate potential for treatment. Accordingly, in one embodiment, at least one microRNA may be selected from the group consisting of hsa-miR-513a-5p, hsa-miR-193a-3p, hsa-miR-7-5p, hsa-miR-575, hsa-miR-221-5p, hsa-miR-133b, hsa-miR-1 and hsa-miR-199a-5p.

FIG. 9 shows the Effect of Lymphocyte Immunotherapy (LIT) on preconception levels of selected miroRNAs. In addition to the microRNA IVIG response, LIT is a preconception therapy used to increase fertility rates and to decrease miscarriage and preeclampsia rates. Because LIT is a preconception treatment, only preconception samples were compared in this analysis. Mean microRNA CT levels in 15 patients using preconception LIT (mean day of blood draw 81.7±55.6 days before conception LMP) were compared to the mean levels in 10 patients not using LIT (mean day of blood draw 62.9±54.9 days before conception LMP). LIT was performed a mean of 31.5±16.6 days before the sample was taken. Differences between mean microRNA levels of patients using LIT and not using LIT were calculated. These results were sorted from largest difference to smallest difference. Standard deviations were calculated for the mean differences between these groups. If the mean difference was found to be ≥1.0 and the standard deviation was found to be <4.0 (due to large SDs seen with preconception samples), the result was marked as significant (marked with XX). Using these criteria, 3 preconception microRNA CT levels were found to be significantly increased by LIT: miR-575, 148a-3p and 144-3p. Four preconception microRNA CT levels were found to be decreased by LIT: miR-210, 193-3p, 199a-5p and 199b-5p. It may be noted that high miR-148-3p and 144-3p levels are seen to be associated with negative pregnancy outcome (c.f., FIGS. 2 and 3). This implies that LIT may be useful as a clinical tool for "correcting" microRNA patterns before a patient actually becomes pregnant. Accordingly, in one embodiment, at least one microRNA may be selected from the group consisting of hsa-miR-575, hsa-miR-144-3p, hsa-miR-148a-3p, hsa-miR-210, hsa-miR-193a-3p, hsa-miR-199b-5p and hsa-miR-199a-5p.

FIG. 10 shows an exemplary scoring system as applied to selected mircoRNAs. Suitable "cut-off" values for the selected microRNAs may be used for predicting pregnancy outcome. By combining the predictive values of individual microRNAs, a more predictive scoring algorithm may be provided. To create this algorithm, first, 28 samples from early pregnancy (mean 60.6±15.0 days gestational age) were collected, 11, preeclampsia and 17 healthy. The absolute values of the mean differences between outcome groups were calculated, as described above for FIG. 4, identifying five microRNAs were selected as "top scorers" (marked xxx). Each of these microRNAs was assigned a "cut off" value for scoring based on a receiver operating characteristic (ROC) curve analysis whereby frequency of the outcome at the top third or bottom third of the population range determined a cut-off level (in this population, the sample preeclampsia:healthy pregnancy ratio was 1:3). Light font represents a healthy pregnancy microRNA CT value. Bold font represents a preeclampsia pregnancy CT value. Starred cells represent CT values above the designated 1/3 level cut-off value. "Pree" indicates preeclampsia and "Heal" indicates healthy.

FIG. 11 shows microRNA significance as scored based on the frequency of the presence of the microRNA in the above figures. Accordingly, in one embodiment, at least one microRNA may be selected from the group consisting of the 11 most frequently occurring microRNAs and may include miR575, miR144-3p, miR199a-5p, miR210, miR1229, miR133b, miR148a-3p, miR193a-3p, miR7-5p, miR223 and miR340-5p.

Figure 12A:
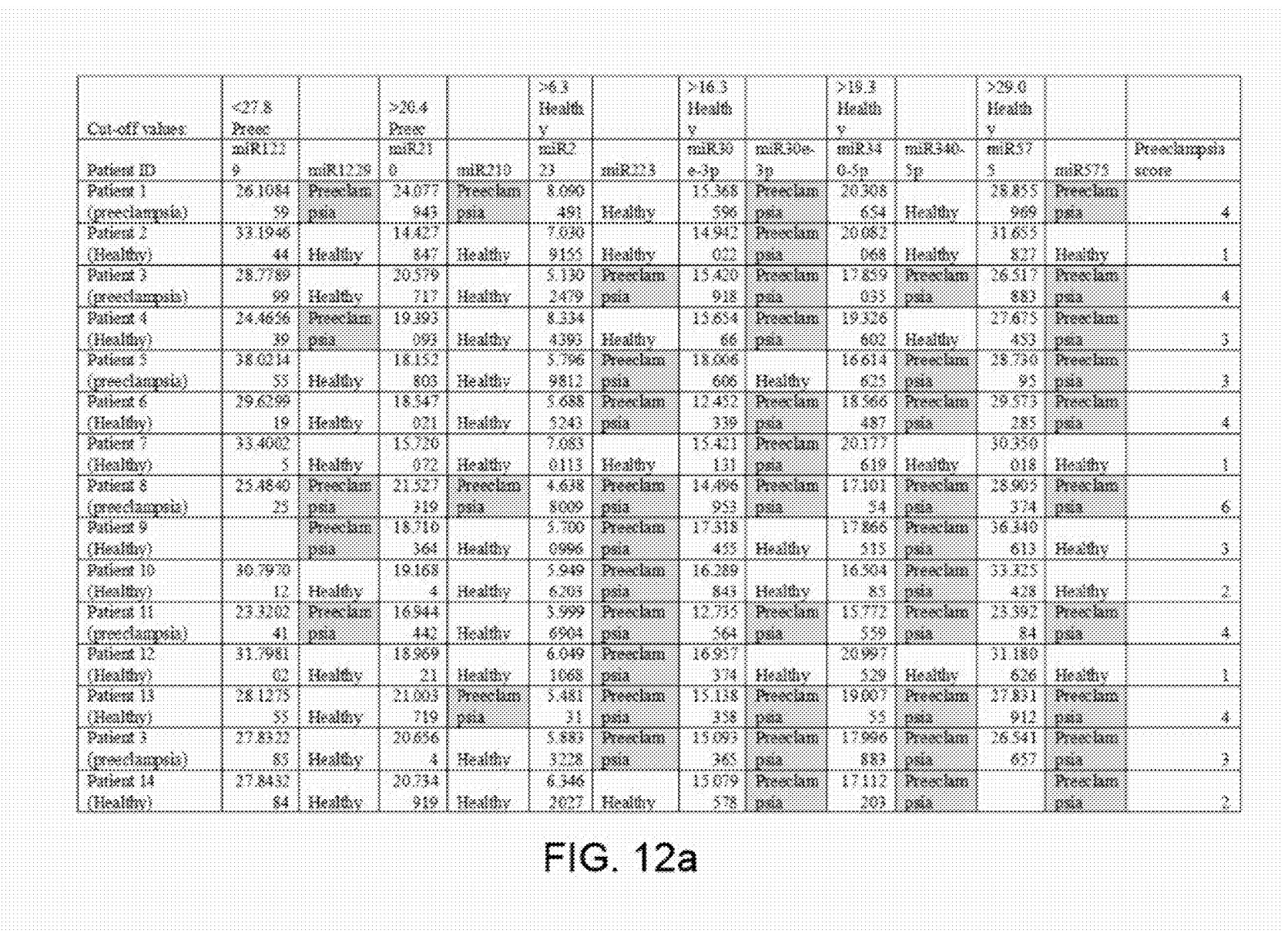
Figure 12B:
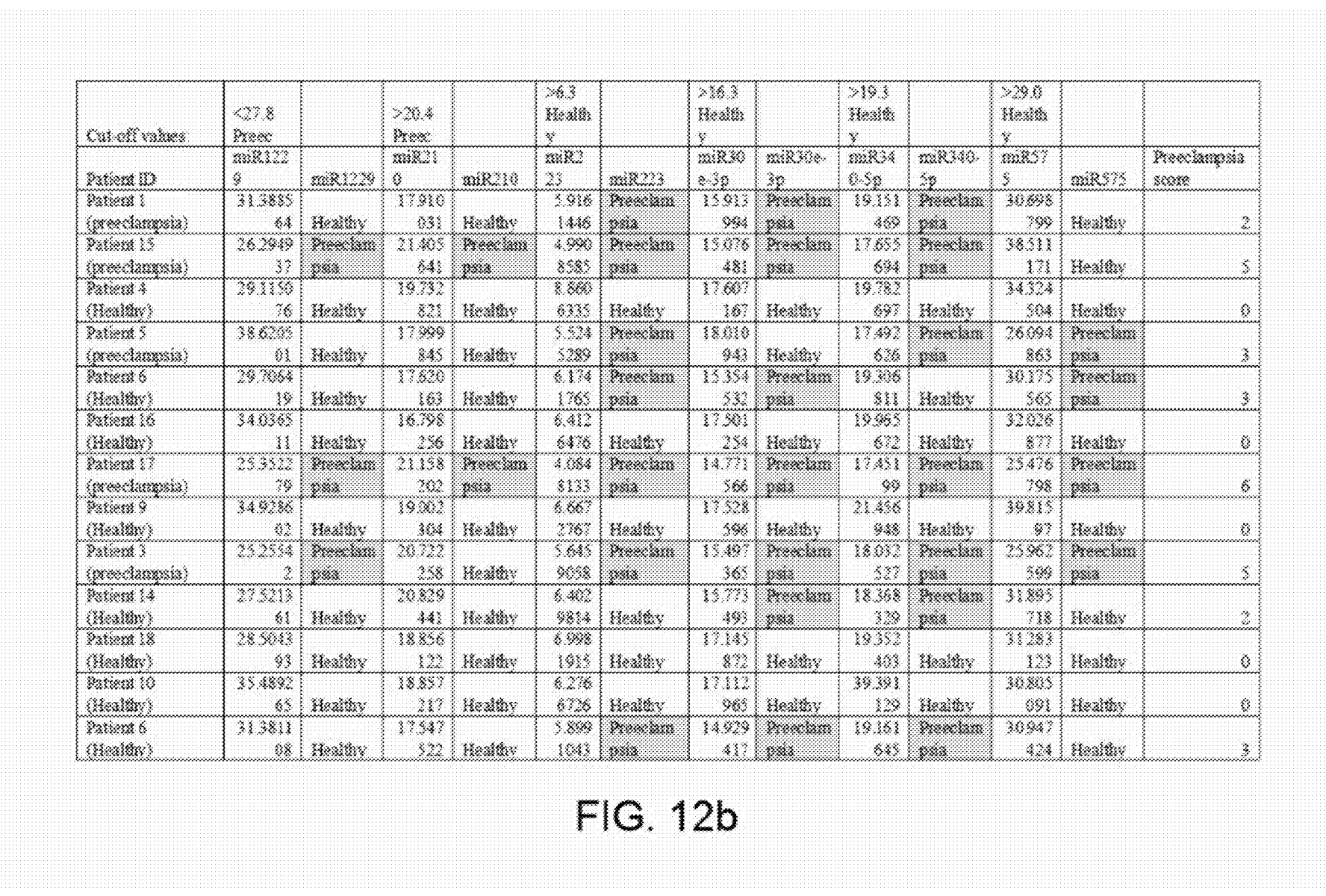

FIGS. 12a and 12b show a microRNA pregnancy outcome predictor scoring system applied to 28 pregnancy microRNA samples drawn in the first trimester (17 Healthy and 11 Preeclampsia). A microRNA CT level falling above or below the "cut-off" value determined whether a patient got a preeclampsia risk factor point (shaded cells). 11 preeclampsia samples and the 17 healthy pregnancy samples were scored. Mean time of blood draw was confined to 30-85 days pregnant (mean 60.5±15.2 days). The total preeclampsia risk factor points were added together for each of the 27 patients tested. Total score ranged from 0 to 6. A higher score correlates with a higher risk of preeclampsia. A lower score correlates with a lower risk of preeclampsia. A risk factor score ≥5 indicated very high preeclampsia risk (5 of 5 samples). A risk factor score ≤2 indicated a very low risk of preeclampsia (1 of 12 samples). ROC curve analysis confirmed that scoring system was predictive and valid (area under the ROC curve: 0.894). Accordingly, in one embodiment, at least one microRNA may be selected from the group consisting of hsa-miR-1229, hsa-miR-210, hsa-miR-223, hsa-miR-30e-3p, hsa-miR-340-5p and hsa-miR-575.

FIG. 13 shows exemplary ROC curve calculations for analysis of the microRNA preeclampsia scoring system. Two sets of patient data were analyzed: 1. Multiple blood draws per patient; 2. Single blood draw per patient. Each table represents one ROC curve analysis, one for each set of data (Group 1, 28 Samples, No IVIG, mean 60.5±15.2 days preg and Group 2, 19 samples, No IVIG, mean 54.5±13 days preg). To calculate the ROC curve scores, two outcomes were used: P (Preeclampsia) and H (Healthy). These two outcomes are arranged by Preeclampsia Risk Factor Score. The ROC curve analyses are shown in FIG. 14.

FIGS. 15-22 show additional data from co-pending PCT/US12/61994 filed Oct. 25, 2012.

Figure 15A:
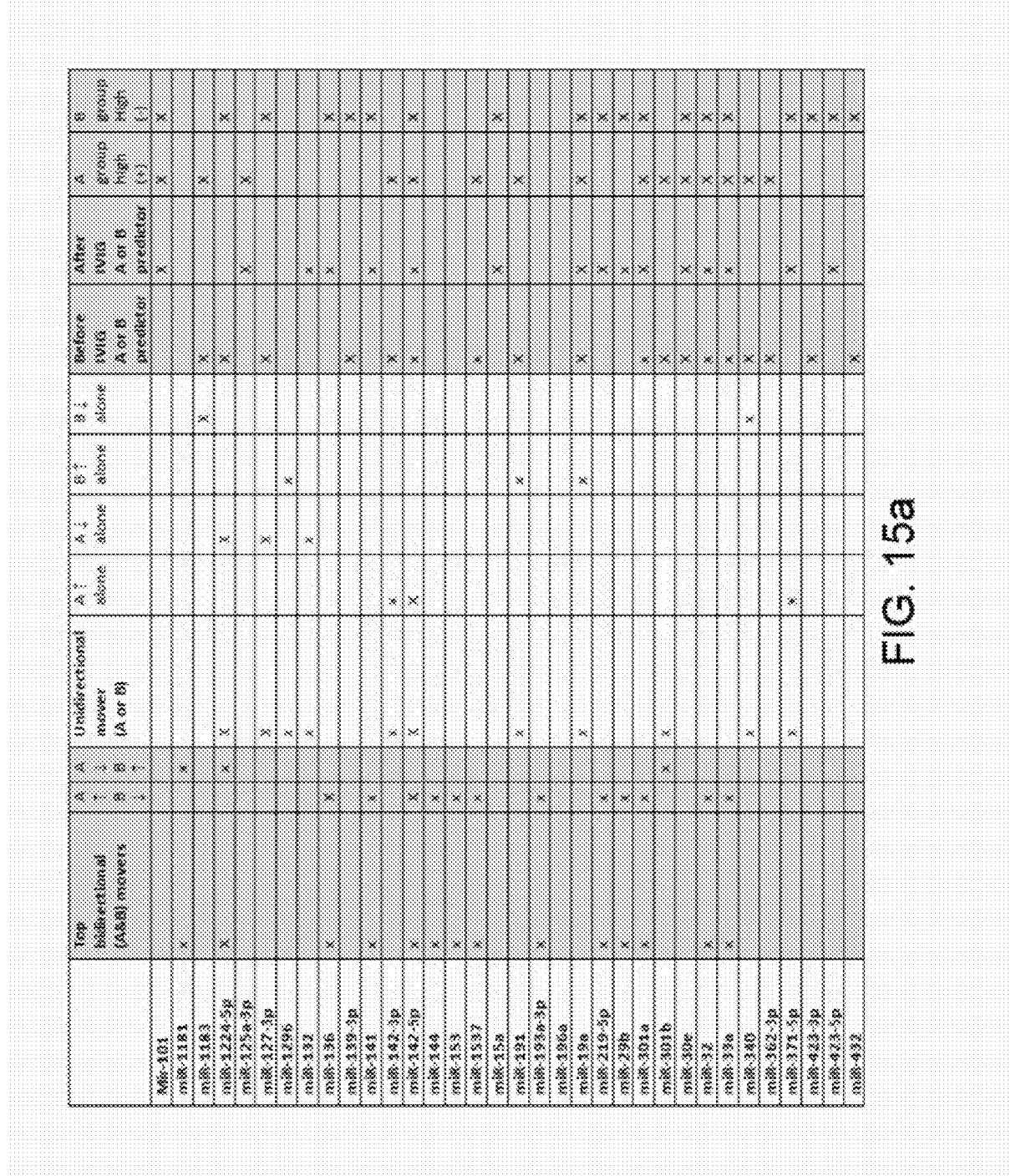
Figure 16A:
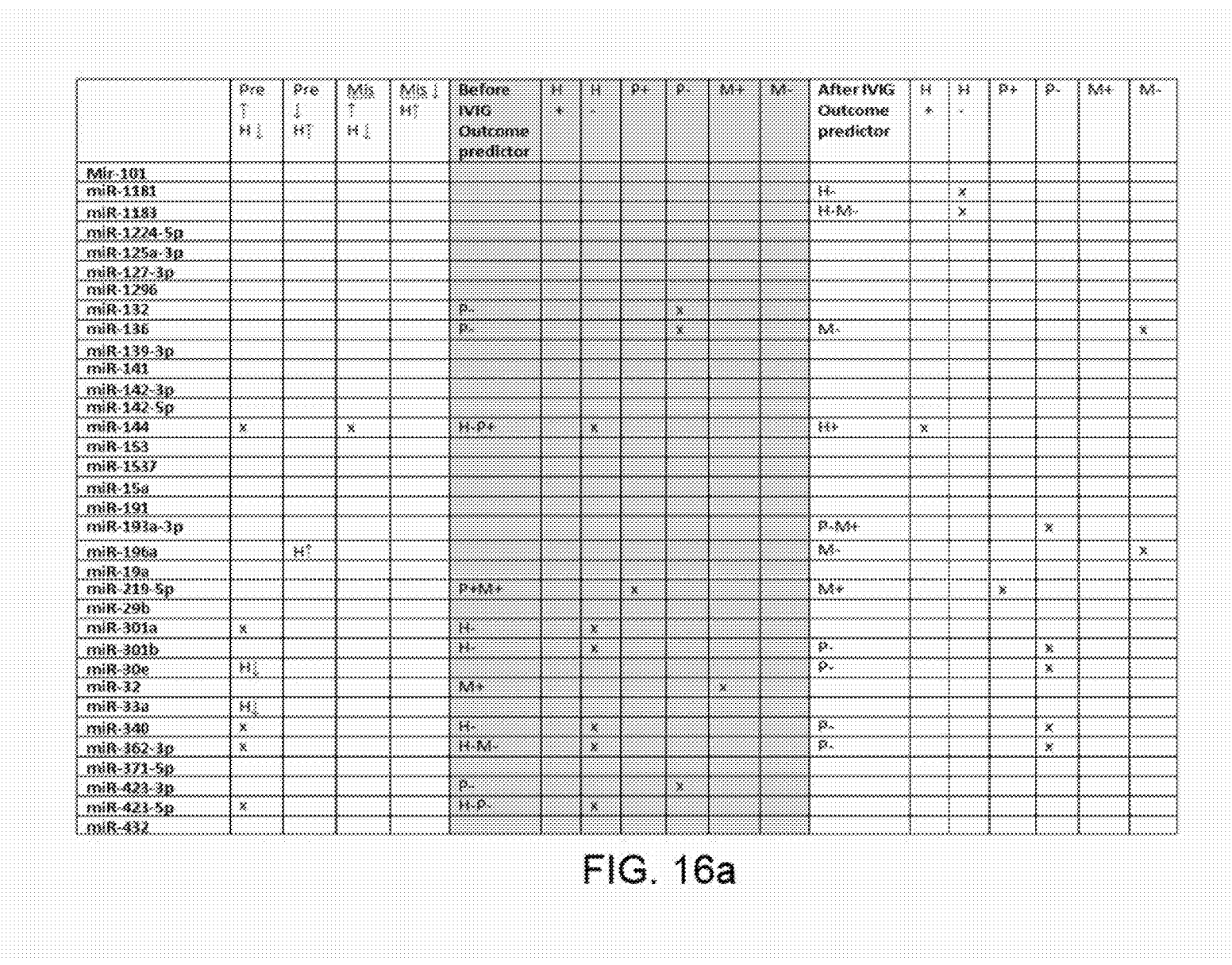
Figure 16B:
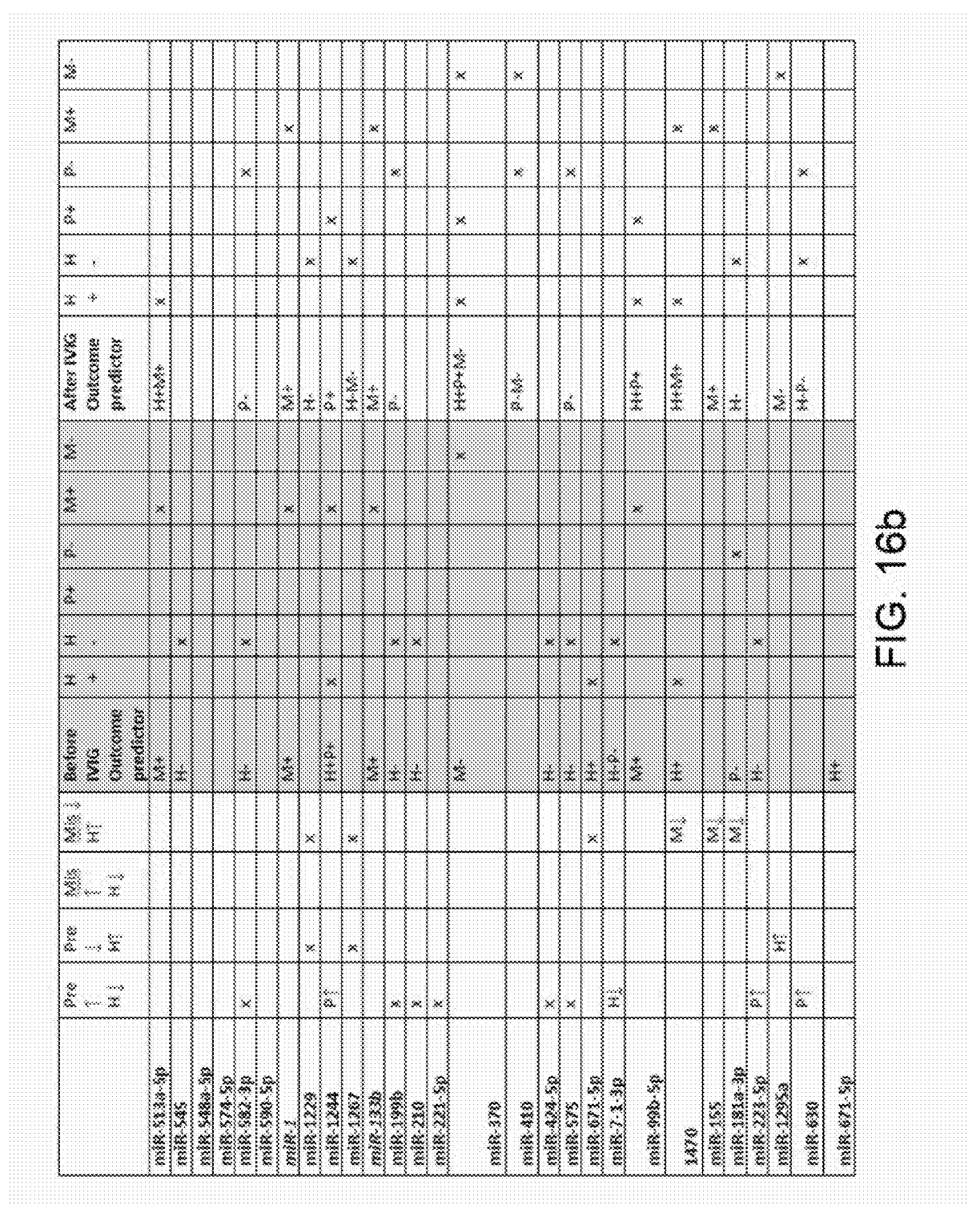

FIGS. 15a and 15b show IVIG response data and FIGS. 16a and 16b shows pregnancy outcome data. As shown, A=IVIG "good responder," B=IVIG "poor responder," H=Healthy pregnancy outcome, P=Preeclampsia outcome, M=Miscarriage outcome, + In Top 25 highest level group out of 962 miRs for designated pregnancy outcome, − In Bottom 25 lowest level group out of 962 miRs for designated pregnancy outcome, ↑ Sequential pregnancy samples show increasing level and ↓ Sequential pregnancy samples show decreasing level.

FIG. 17 shows 15 top microRNA marker candidates obtained from microarray analysis of 962 microRNAs. Accordingly, in one embodiment, at least one microRNA may be selected from the group consisting of hsa-miR-144-3p, hsa-miR-582-5p, hsa-miR-30e-3p, hsa-miR-340-5p, hsa-miR-424-5p, hsa-miR-199a-5p, hsa-miR-199b-5p, hsa-miR-210, hsa-miR-221-5p, hsa-miR-33a-5p, hsa-miR-575, hsa-miR-7-5p, hsa-miR-1229, hsa-miR-1267 and hsa-miR-671-3p.

Figure 18:
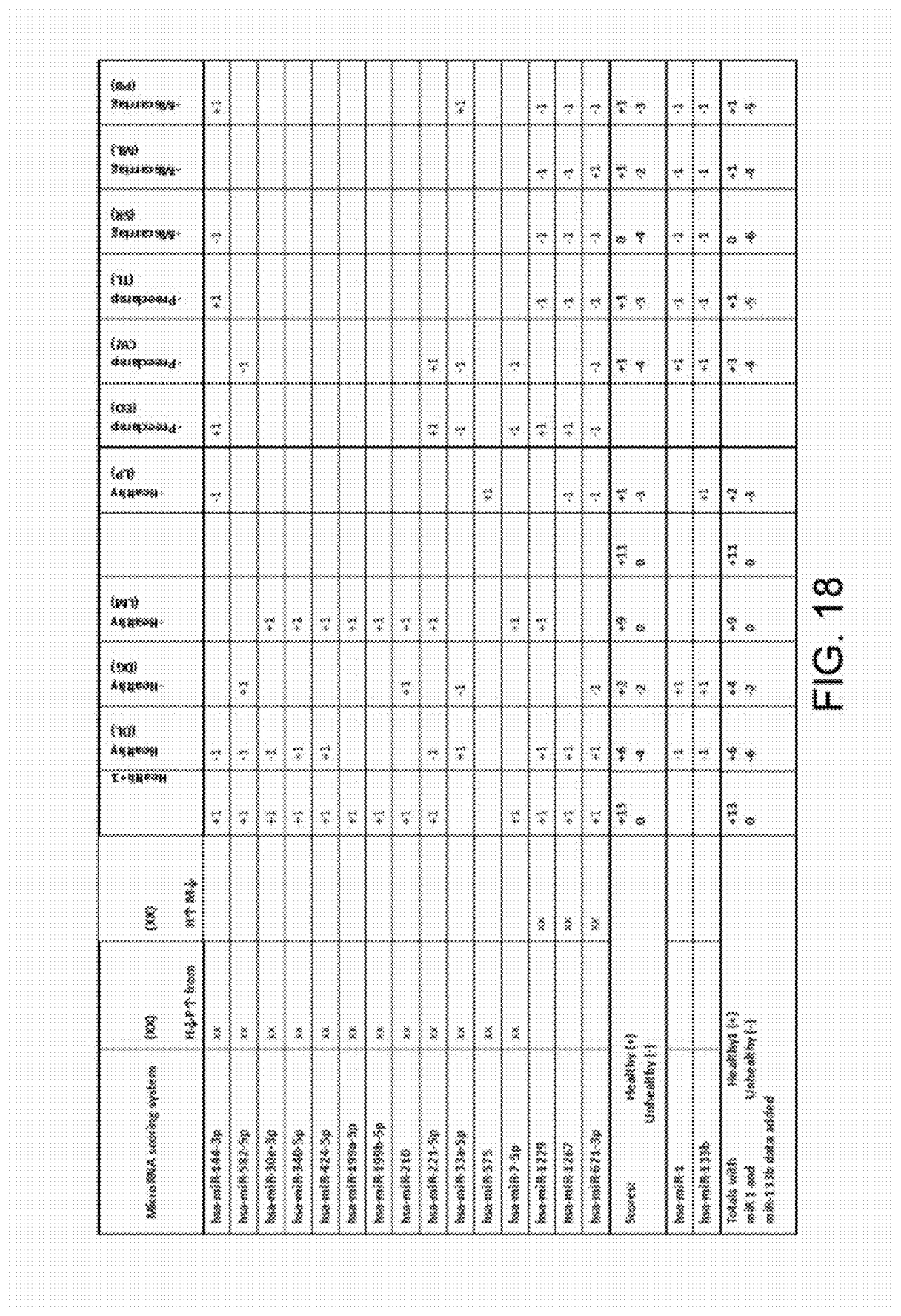

FIG. 18 shows an exemplary microRNA pregnancy outcome predictor.

Figure 19A:
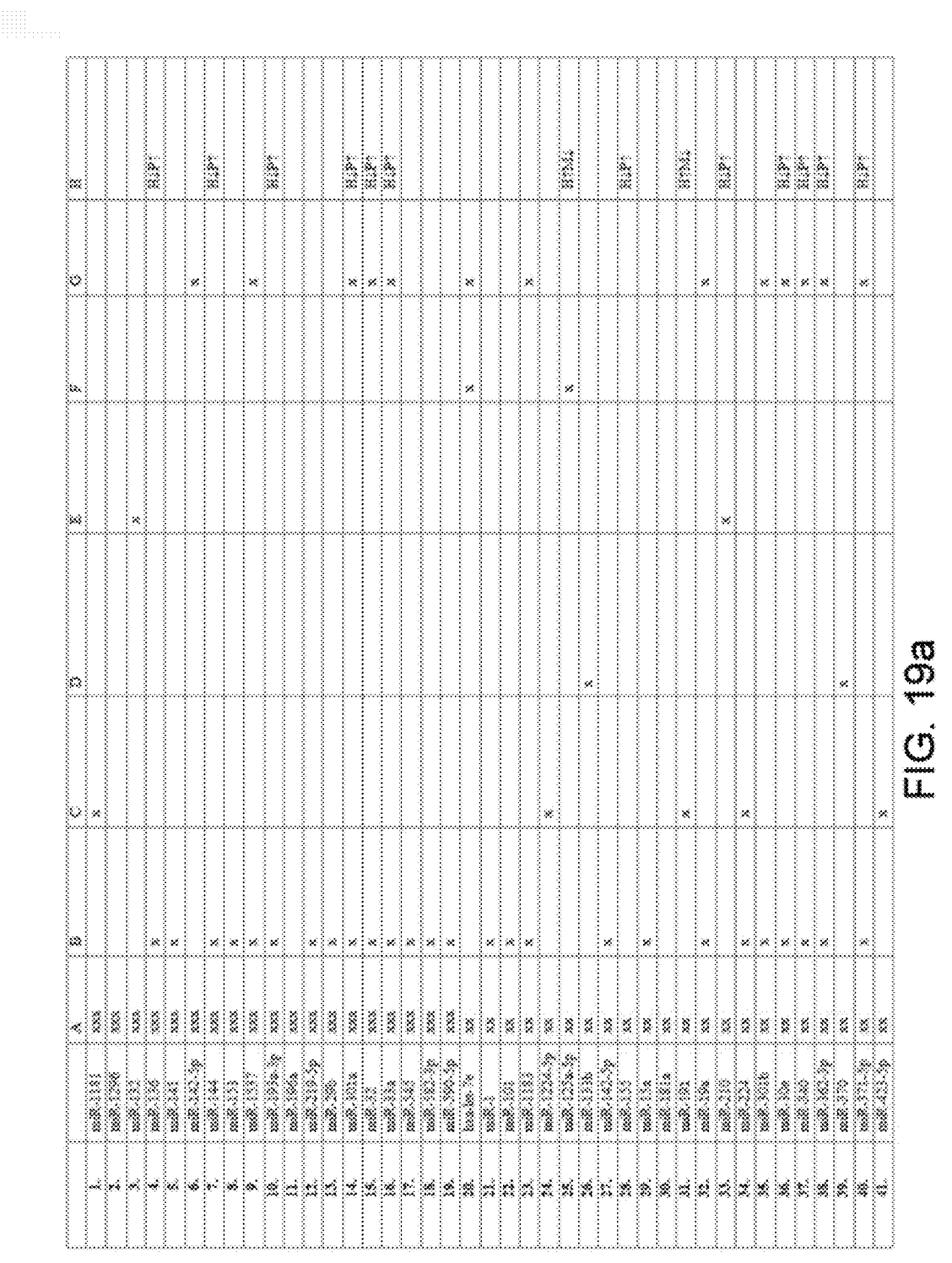
Figure 19B:
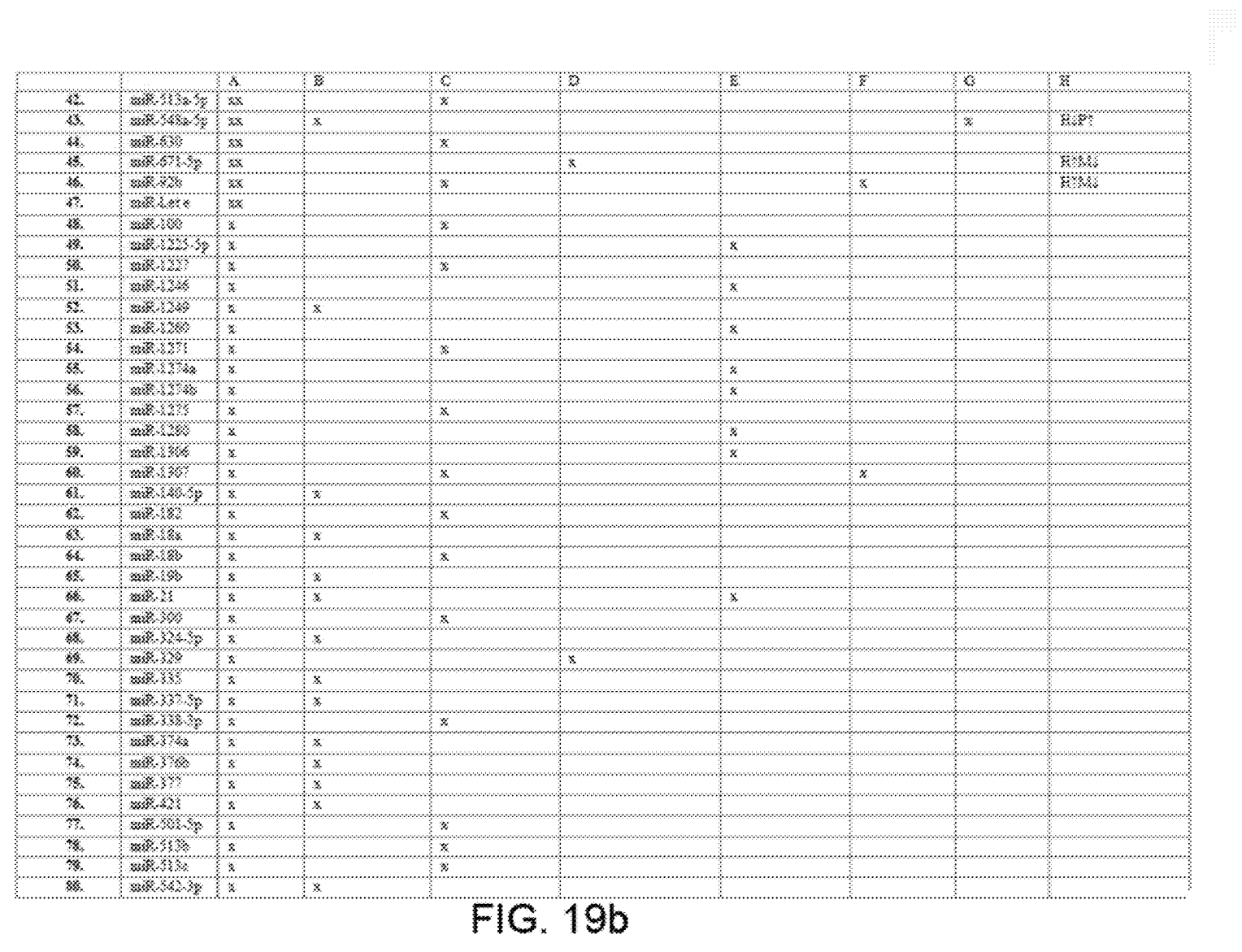

FIGS. 19a and 19b show 19 top microRNA marker candidates obtained from microarray analysis of 893 microRNAs for Group A and B IVIG response data combined with microRNA pregnancy outcome data (column H). Column A shows MicroRNA Group AB IVIG response ranking, Column B shows A most increased and B most decreased divergent movers from most extreme 100 of each group, Column C shows A most decreased and B most increased divergent movers from most extreme 100 of each group, Column D shows Common same direction movers of increasing A and increasing B groups selected from top 100 of each, Column E shows Common same direction movers of decreasing A and decreasing B groups selected from bottom 100 of each, Column F shows Before IVIG samples: high level (>1) miRs that predict group A or B behavior, Column G shows After IVIG samples: high level (>1) miRs that predict group A or B behavior, and Column H shows Pregnancy outcome data with Most increased ↑ and most decreased ↓ common divergent movers from top 25's of both outcome groups, healthy (H), preeclampsia (P) or miscarriage (M). Accordingly, in one embodiment, at least one microRNA may be selected from the group consisting of hsa-miR-1181, hsa-miR-1296, hsa-miR-132, hsa-miR-136, hsa-miR-141, hsa-miR-142-5p, hsa-miR-144, hsa-miR-153, hsa-miR-1537, hsa-miR-193a-3p, hsa-miR-196a, hsa-miR-219-5p, hsa-miR-29b, hsa-miR-301a, hsa-miR-32, hsa-miR-33a, hsa-miR-545, hsa-miR-582-3p and hsa-miR-590-5p.

Figure 20A:
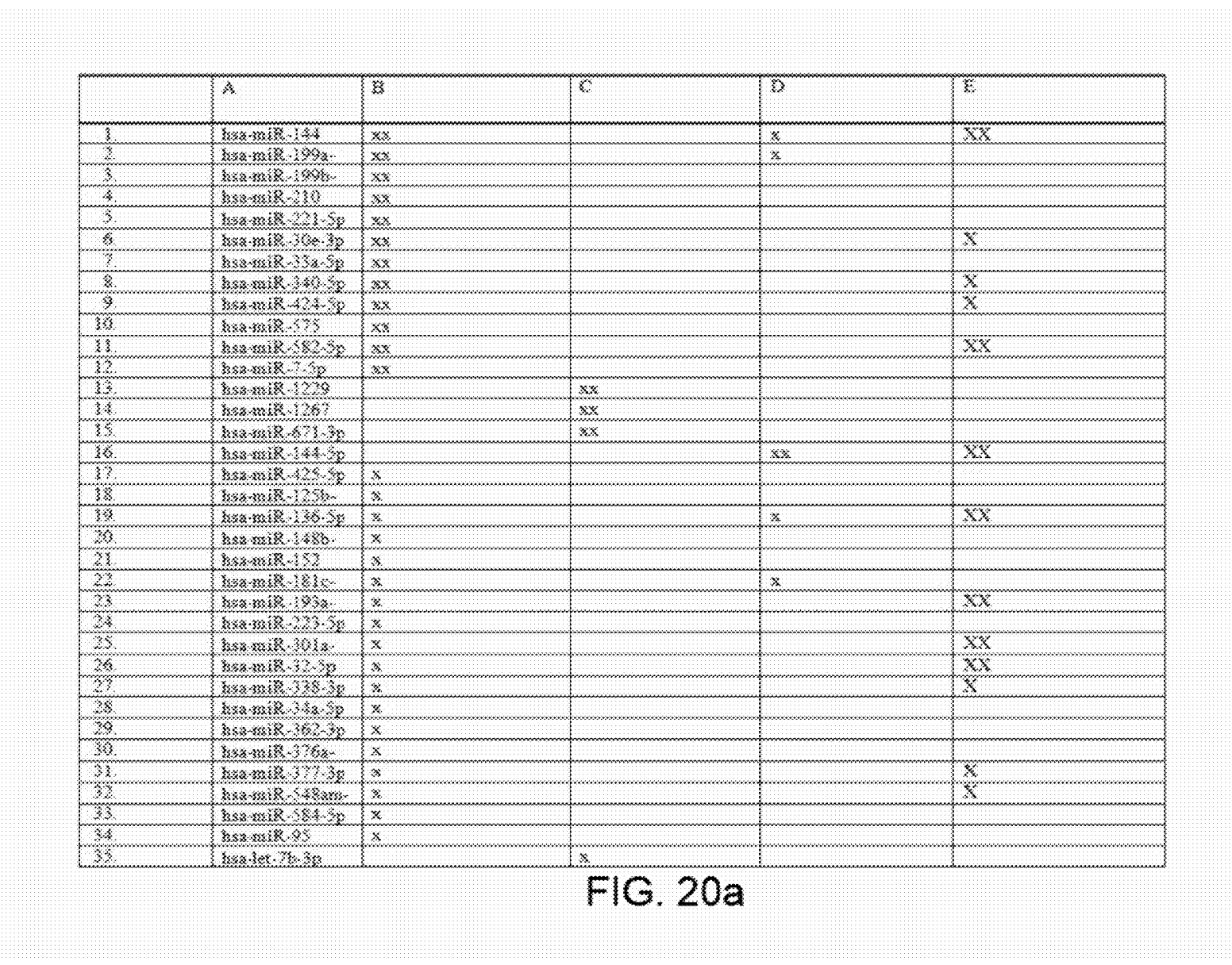
Figure 20B:
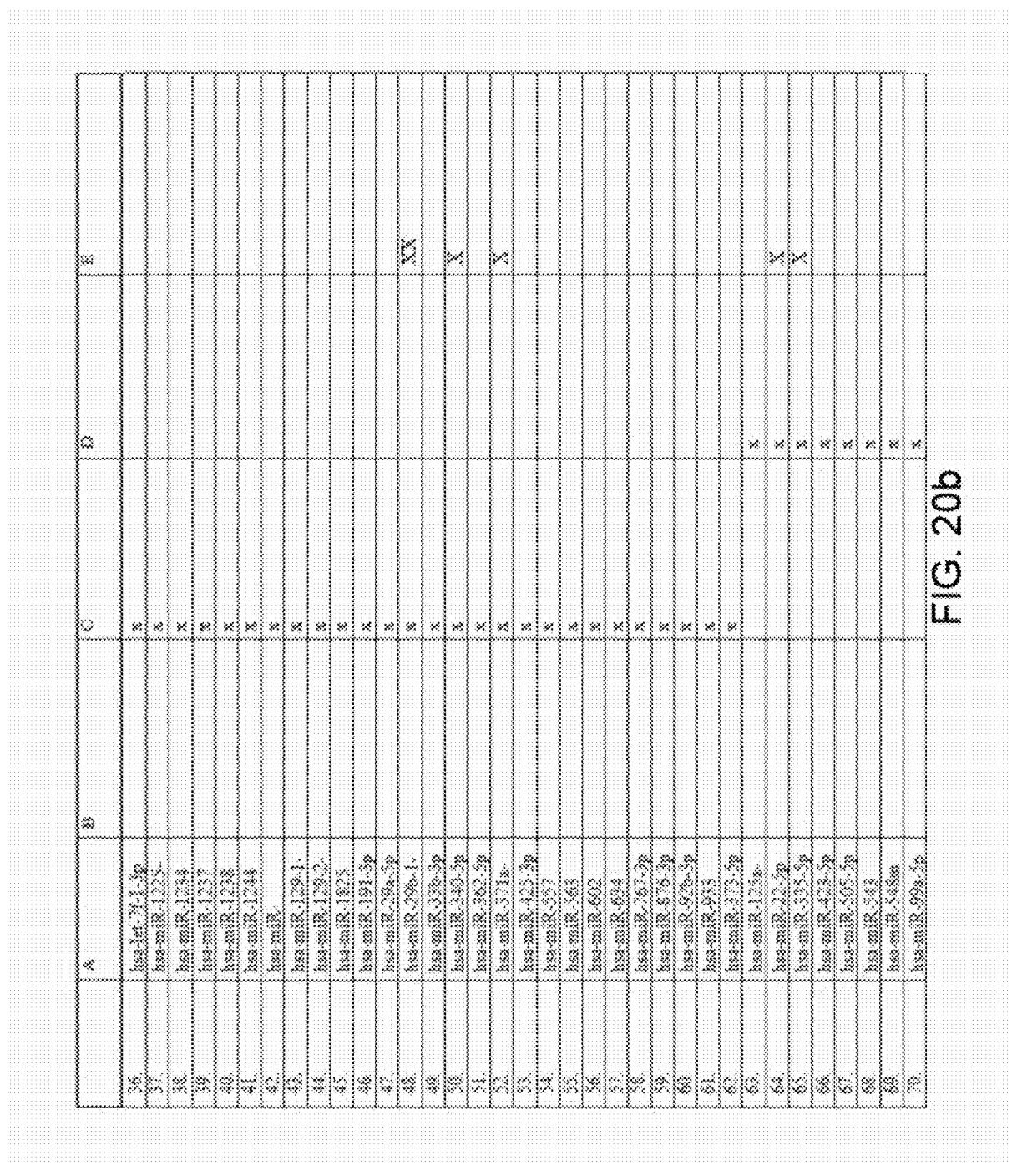

FIGS. 20a and 20b show selected microRNAs having significant pregnancy outcome prediction derived from a 962 microRNA microarray using 12 patient outcomes (6 healthy, 3 preeclampsia, 3 miscarriage). As shown, ↑ indicates Most increased, ↓ Most decreased, H=Healthy, P=Preeclampsia, M=Miscarriage, and Column A identifies the microRNAs, Column B shows (XX) H↓P↑ from top 25s and (X) H↓P↑ from top 100s, Column C shows (XX) H↑ M↓ from top 25s and (X)H↑ M↓ from top 100s, Column D shows (XX) H↓ M↑ from top 25s and (X) H↓ M↑ from top 100s, and Column E shows miR Group A-B behavior category in response to IVIG (XX) from top 25s and (X) from top 100s.

FIG. 21 shows the top 25 differences between mean Healthy level and mean Preeclampsia and miscarriage levels before IVIG, from a 962 microRNAs microarray. FIG. 22 shows the bottom 25 differences between mean Healthy level and mean Preeclampsia and miscarriage levels before IVIG from a 962 microRNAs microarray.

Described herein are presently preferred embodiments. However, one skilled in the art that pertains to the present invention will understand that the principles of this disclosure can be extended easily with appropriate modifications to other applications.

What is claimed is:

1. A method comprising:
   (a) quantifying the expression of four microRNAs (miRNAs) in one or more maternal blood cells of a pregnant human being, the four miRNAs being hsa-miR-148a-3p, hsa-miR-210, hsa-miR-301a-3p, and hsa-miR-223;
   (b) comparing the expression of the four miRNAs determined in step a) to the expression of the same miRNAs in a control sample to determine whether the pregnant human being is at risk of developing preeclampsia, wherein an increase in expression in the pregnant human being relative to the control sample indicates the pregnant human being is at risk of developing preeclampsia; and,
   (c) treating a pregnant human being identified in step b) as being at risk of developing a preeclampsia using immunotherapy.

2. The method of claim 1 further comprising quantifying the expression of at least one miRNA selected from the group consisting of hsa-miR-1, hsa-miR-1229, hsa-miR-1244, hsa-miR-1267, hsa-miR-132, hsa-miR-133b, hsa-miR-144-3p, hsa-miR-146a, hsa-miR-155, hsa-miR-16, hsa-miR-181a, hsa-miR-193a-3p, hsa-miR-196a, hsa-miR-199a-5p, hsa-miR-199b-5p, hsa-miR-219-5p, hsa-miR-221-5p, hsa-miR-30e-3p, hsa-miR-33a-5p, hsa-miR-340-5p, hsa-miR-424-5p, hsa-miR-513a-5p, hsa-miR-575, hsa-miR-582-5p, hsa-miR-671-3p, hsa-miR-7-5p, hsa-miR-132, hsa-miR-136, hsa-miR-141, hsa-miR-144, hsa-miR-153, hsa-miR-193a-3p, hsa-miR-196a, hsa-miR-219-5p, hsa-miR-301a, hsa-miR-32, hsa-miR-33a, hsa-miR-545, hsa-miR-582-3p, and hsa-miR-590-5p.

3. The method of claim 1 wherein the one or more maternal blood cells are obtained during the first trimester of pregnancy.

4. The method of claim 2 wherein the one or more maternal blood cells are obtained during the first trimester of pregnancy.

5. A method comprising:
   (a) quantifying the expression of four microRNAs (miRNAs) in one or more maternal blood cells of a pregnant human being, the four miRNAs being hsa-miR-148a-3p, hsa-miR-210, hsa-miR-301a-3p, and hsa-miR-223;
   (b) comparing the expression of the four miRNAs determined in step a) to the expression of the same miRNAs in a control sample to determine whether the pregnant human being is at risk of having a miscarriage, wherein an increase in expression in the pregnant human being relative to the control sample indicates the pregnant human being is at risk of having a miscarriage; and,
   (c) treating a pregnant human being identified in step b) as being at risk of having a miscarriage using immunotherapy.

6. The method of claim 5 further comprising quantifying the expression of at least one miRNA selected from the group consisting of hsa-miR-1, hsa-miR-1229, hsa-miR-1244, hsa-miR-1267, hsa-miR-132, hsa-miR-133b, hsa-miR-144-3p, hsa-miR-146a, hsa-miR-155, hsa-miR-16, hsa-miR-181a, hsa-miR-193a-3p, hsa-miR-196a, hsa-miR-199a-5p, hsa-miR-199b-5p, hsa-miR-219-5p, hsa-miR-221-5p, hsa-miR-30e-3p, hsa-miR-33a-5p, hsa-miR-340-5p, hsa-miR-424-5p, hsa-miR-513a-5p, hsa-miR-575, hsa-miR-582-5p, hsa-miR-671-3p, hsa-miR-7-5p, hsa-miR-132, hsa-miR-136, hsa-miR-141, hsa-miR-144, hsa-miR-153, hsa-miR-193a-3p, hsa-miR-196a, hsa-miR-219-5p, hsa-miR-301a, hsa-miR-32, hsa-miR-33a, hsa-miR-545, hsa-miR-582-3p, and hsa-miR-590-5p.

7. The method of claim 5 wherein the one or more maternal blood cells are obtained during first trimester of pregnancy.

8. The method of claim 6 wherein the one or more maternal blood cells are obtained during the first trimester of pregnancy.

9. A method comprising:
(a) quantifying the expression of four microRNAs (miRNA) in one or more maternal blood cells of a pregnant human being, the four miRNAs being hsa-miR-148a-3p, hsa-miR-210, hsa-miR-301a-3p, and hsa-miR-223;
(b) comparing the expression of the four miRNAs determined in step a) to the expression of the same miRNAs in a control sample to determine whether the pregnant human being is at risk of having a preterm birth, wherein an increase in expression in the pregnant human being relative to the control sample indicates the pregnant human being is at risk of having a preterm birth; and,
(c) treating a pregnant human being identified in step b) as being at risk of having a preterm birth using immunotherapy.

10. The method of claim 9 further comprising quantifying the expression of at least one miRNA selected from the group consisting of hsa-miR-1, hsa-miR-1229, hsa-miR-1244, hsa-miR-1267, hsa-miR-132, hsa-miR-133b, hsa-miR-144-3p, hsa-miR-146a, hsa-miR-155, hsa-miR-16, hsa-miR-181a, hsa-miR-193a-3p, hsa-miR-196a, hsa-miR-199a-5p, hsa-miR-199b-5p, hsa-miR-219-5p, hsa-miR-221-5p, hsa-miR-30e-3p, hsa-miR-33a-5p, hsa-miR-340-5p, hsa-miR-424-5p, hsa-miR-513a-5p, hsa-miR-575, hsa-miR-582-5p, hsa-miR-671-3p, hsa-miR-7-5p, hsa-miR-132, hsa-miR-136, hsa-miR-141, hsa-miR-144, hsa-miR-153, hsa-miR-193a-3p, hsa-miR-196a, hsa-miR-219-5p, hsa-miR-301a, hsa-miR-32, hsa-miR-33a, hsa-miR-545, hsa-miR-582-3p, and hsa-miR-590-5p.

11. The method of claim 9 wherein the one or more maternal blood cells are obtained during the first trimester of pregnancy.

12. The method of claim 10 wherein the one or more maternal blood cells are obtained during the first trimester of pregnancy.

* * * * *